US010610200B2

(12) United States Patent
Arant et al.

(10) Patent No.: US 10,610,200 B2
(45) Date of Patent: Apr. 7, 2020

(54) GEL APPLICATION SYSTEM

(71) Applicant: Neural Analytics, Inc., Los Angeles, CA (US)

(72) Inventors: John Arant, Los Angeles, CA (US); Sandeep Deol, Los Angeles, CA (US); Trevor Dunlop, Los Angeles, CA (US); Lane Stith, Los Angeles, CA (US); Seth Wilk, Los Angeles, CA (US); Jan Zwierstra, Los Angeles, CA (US)

(73) Assignee: Neural Analytics, Inc., Los Angeles, CA (US)

(*) Notice: Subject to any disclaimer, the term of this patent is extended or adjusted under 35 U.S.C. 154(b) by 0 days.

(21) Appl. No.: 16/198,678

(22) Filed: Nov. 21, 2018

(65) Prior Publication Data
US 2019/0150890 A1 May 23, 2019

Related U.S. Application Data

(60) Provisional application No. 62/589,982, filed on Nov. 22, 2017.

(51) Int. Cl.
*B43K 5/14* (2006.01)
*A61B 8/00* (2006.01)
(Continued)

(52) U.S. Cl.
CPC ............ *A61B 8/4281* (2013.01); *A45D 34/04* (2013.01); *A45D 37/00* (2013.01);
(Continued)

(58) Field of Classification Search
CPC .. A61M 35/003; A61M 35/006; A61B 8/4281
(Continued)

(56) References Cited

U.S. PATENT DOCUMENTS 2,569,073 A 9/1951 Robinson
3,669,323 A 6/1972 Harker et al.
(Continued)

FOREIGN PATENT DOCUMENTS

| CA | 2332430 A1 | 1/2000 |
| DE | 39 34 316 A1 | 4/1991 |
| WO | WO-2007/027278 A1 | 3/2007 |

OTHER PUBLICATIONS

Partial Search Report dated Mar. 28, 2019, for international patent application No. PCT/US2018/062334.
(Continued)

*Primary Examiner* — Jennifer C Chiang
(74) *Attorney, Agent, or Firm* — Foley & Lardner LLP

(57) ABSTRACT

A gel application system includes an applicator body having a first surface, a second surface and at least one opening extending through the applicator body from the first surface to the second surface. At least one gel packet is attached to the first surface of the applicator and defines an interior volume containing gel. The interior volume of the gel packet is in fluid flow communication with the at least one opening. The at least one gel packet is made of a material that has sufficient flexibility to allow a user to squeeze and compress the interior volume and expel gel through the at least one opening, by applying a compression force on the gel packet.

29 Claims, 38 Drawing Sheets

(51) Int. Cl.
*A61F 13/40* (2006.01)
*A61M 35/00* (2006.01)
*A45D 34/04* (2006.01)
*A45D 37/00* (2006.01)
*A45D 40/00* (2006.01)

(52) U.S. Cl.
CPC ....... *A45D 40/0087* (2013.01); *A61M 35/003* (2013.01); *A61M 35/006* (2013.01)

(58) Field of Classification Search
USPC .................................................. 401/132, 133
See application file for complete search history.

(56) References Cited

U.S. PATENT DOCUMENTS

| | | | |
|---|---|---|---|
| 4,140,409 A | 2/1979 | DeVries | |
| 4,430,013 A | 2/1984 | Kaufman | |
| 5,316,400 A | 5/1994 | Hoyt et al. | |
| 5,391,420 A | 2/1995 | Bootman et al. | |
| 5,839,614 A | 11/1998 | Brown | |
| 6,065,642 A | 5/2000 | Brown | |
| 6,079,594 A | 6/2000 | Brown et al. | |
| 6,273,296 B1 | 8/2001 | Brown | |
| 6,530,504 B2 | 3/2003 | Socier | |
| 7,077,296 B2 | 7/2006 | Brown et al. | |
| 7,506,762 B2 | 3/2009 | Nelson et al. | |
| 7,575,384 B2 * | 8/2009 | Bauer | A47K 7/03 401/7 |
| 7,604,623 B2 * | 10/2009 | Brunner | C11D 17/041 604/383 |
| 8,297,866 B2 * | 10/2012 | de Gery | B65D 81/3261 401/132 |
| 8,534,947 B2 * | 9/2013 | Prax | A45D 34/04 401/133 |
| 8,591,130 B2 | 11/2013 | Koptis et al. | |
| 8,651,761 B2 | 2/2014 | Maloney et al. | |
| 8,708,980 B2 | 4/2014 | Welser | |
| 8,709,099 B2 | 4/2014 | Littig et al. | |
| 8,714,855 B2 | 5/2014 | Littig et al. | |
| 9,326,645 B1 | 5/2016 | Bank et al. | |
| 10,159,823 B2 | 12/2018 | Tidwell | |
| 10,179,343 B2 | 1/2019 | Compton et al. | |
| 2010/0264044 A1 | 10/2010 | Beihoffer et al. | |
| 2013/0233886 A1 | 9/2013 | Long et al. | |

OTHER PUBLICATIONS

Non-Final Office Action dated Mar. 19, 2019, from U.S. Appl. No. 16/198,699.
U.S. Non-Final Office Action dated Feb. 7, 2019, from U.S. Appl. No. 16/198,722.
International Search Report and Written Opinion dated May 23, 2019, from application No. PCT/US2018/062334.

* cited by examiner

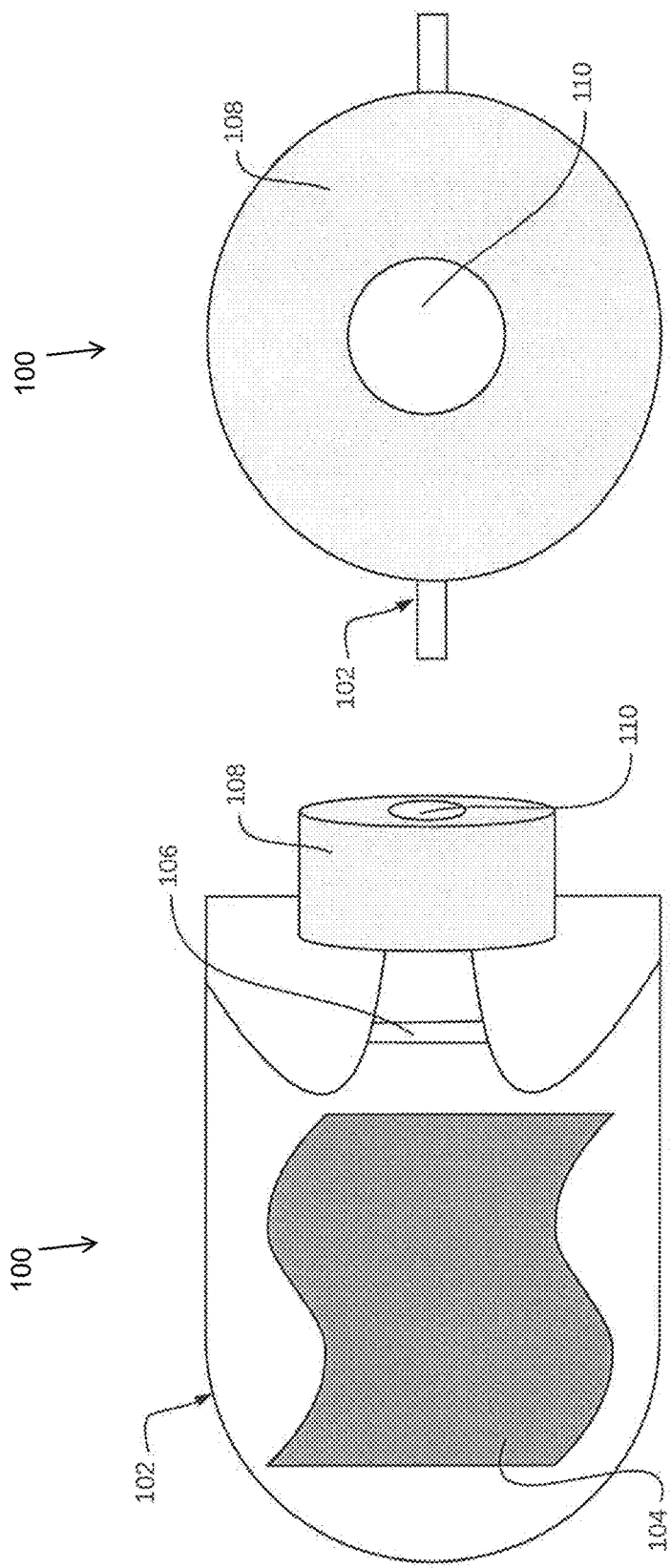

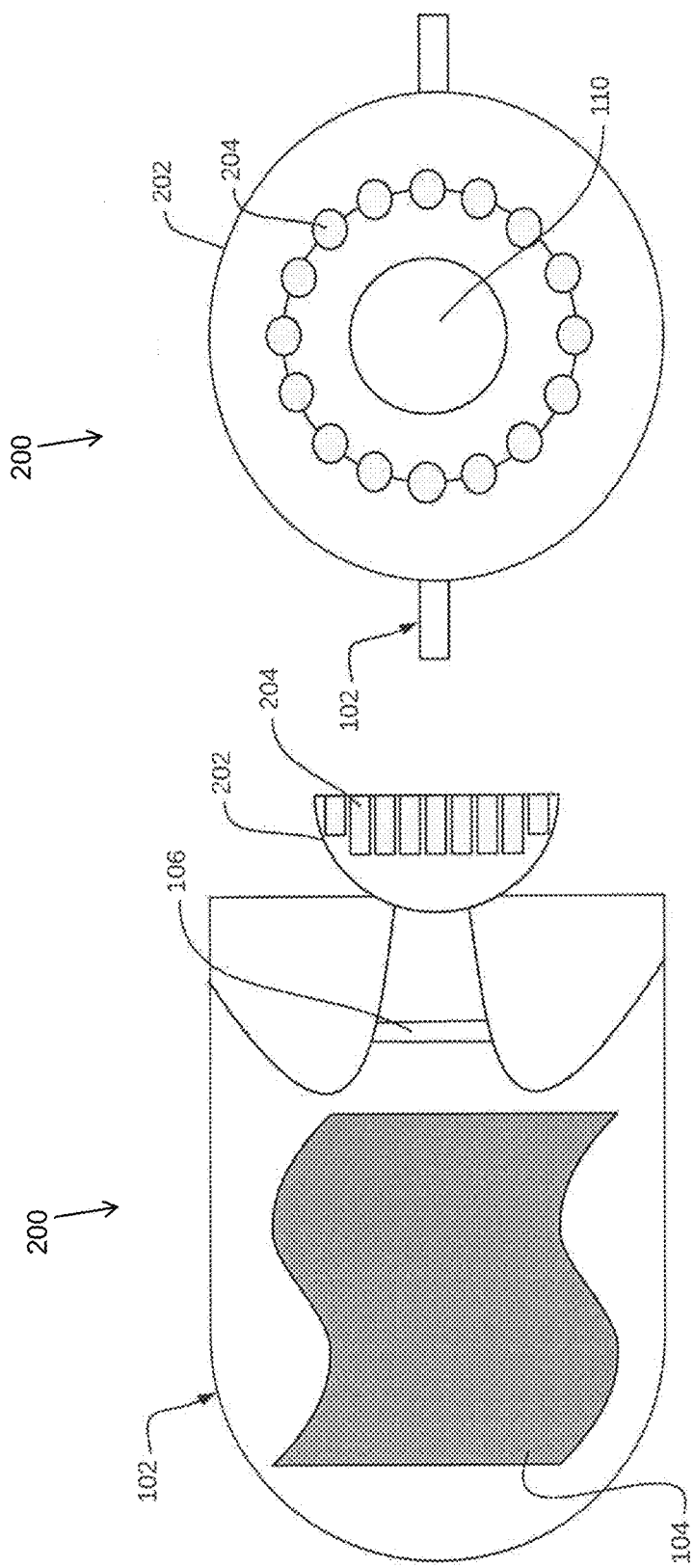

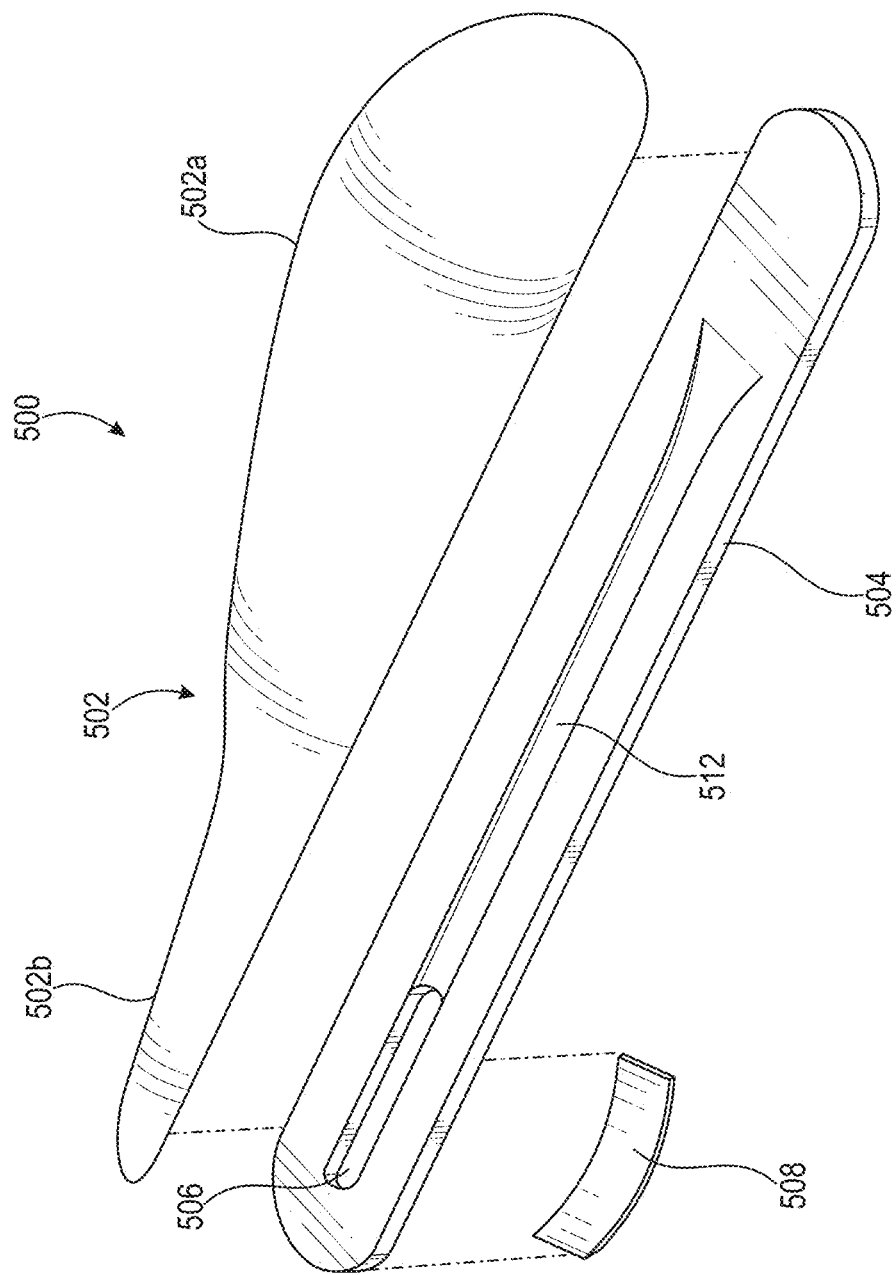

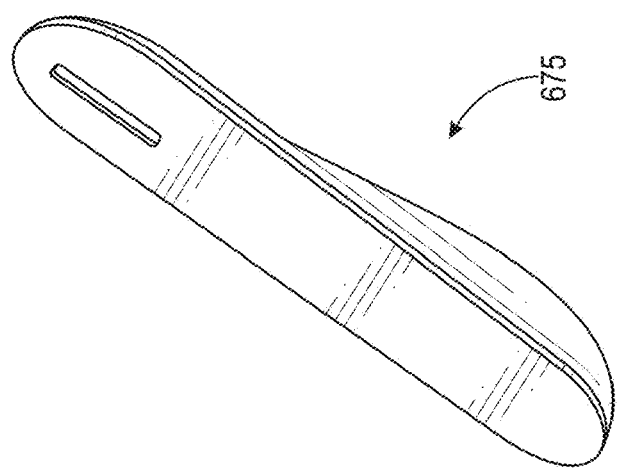
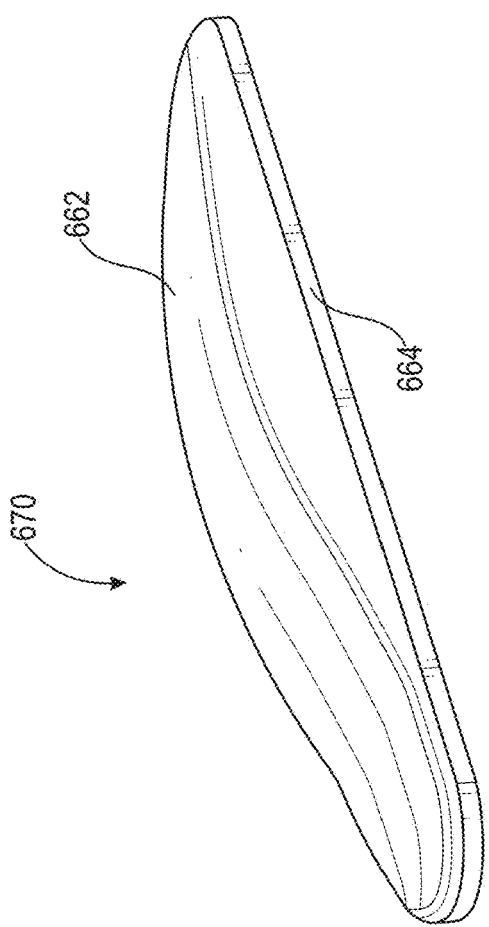

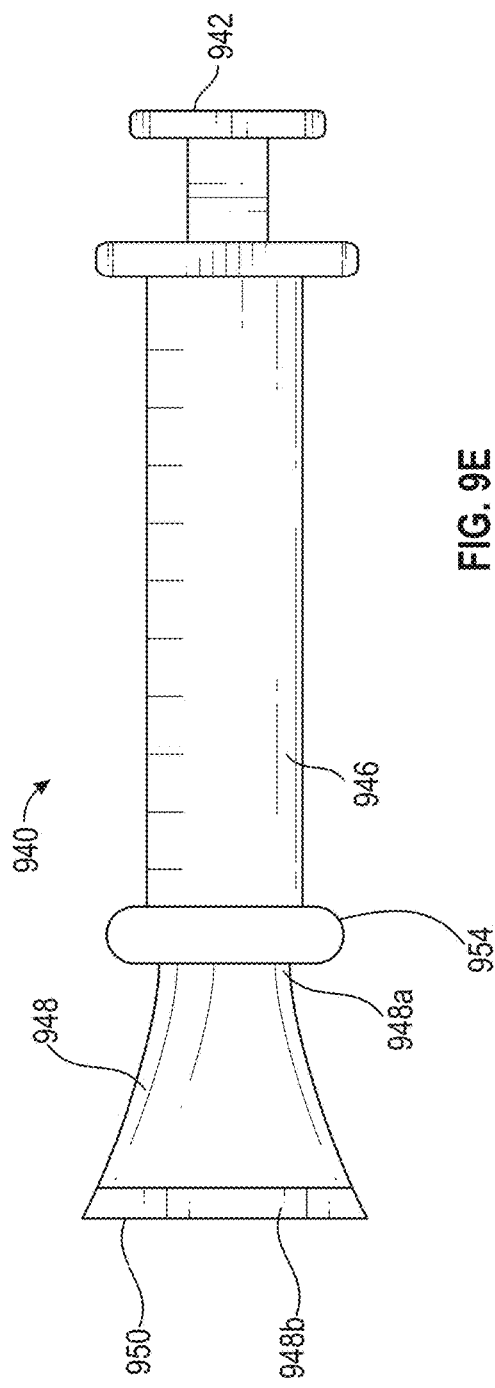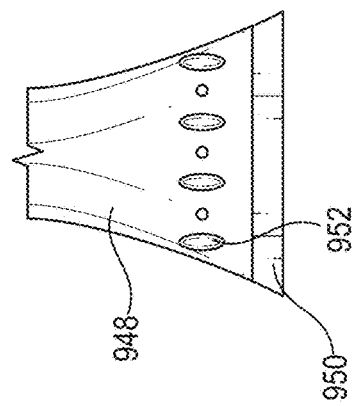

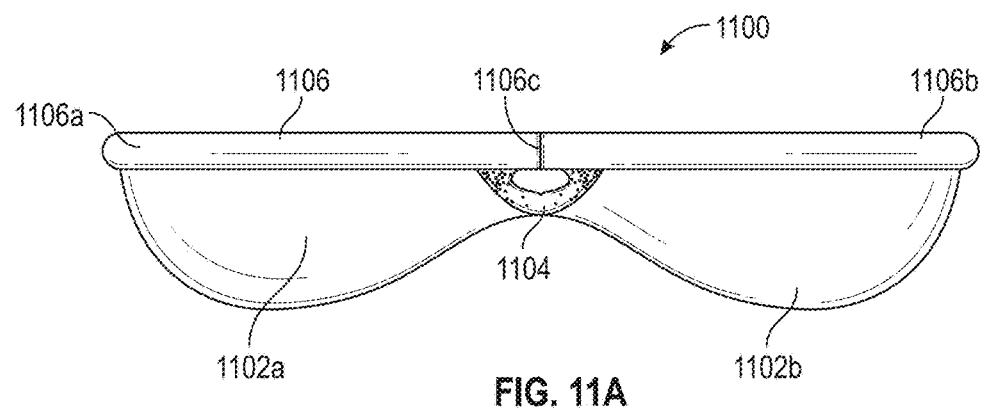
FIG. 11A
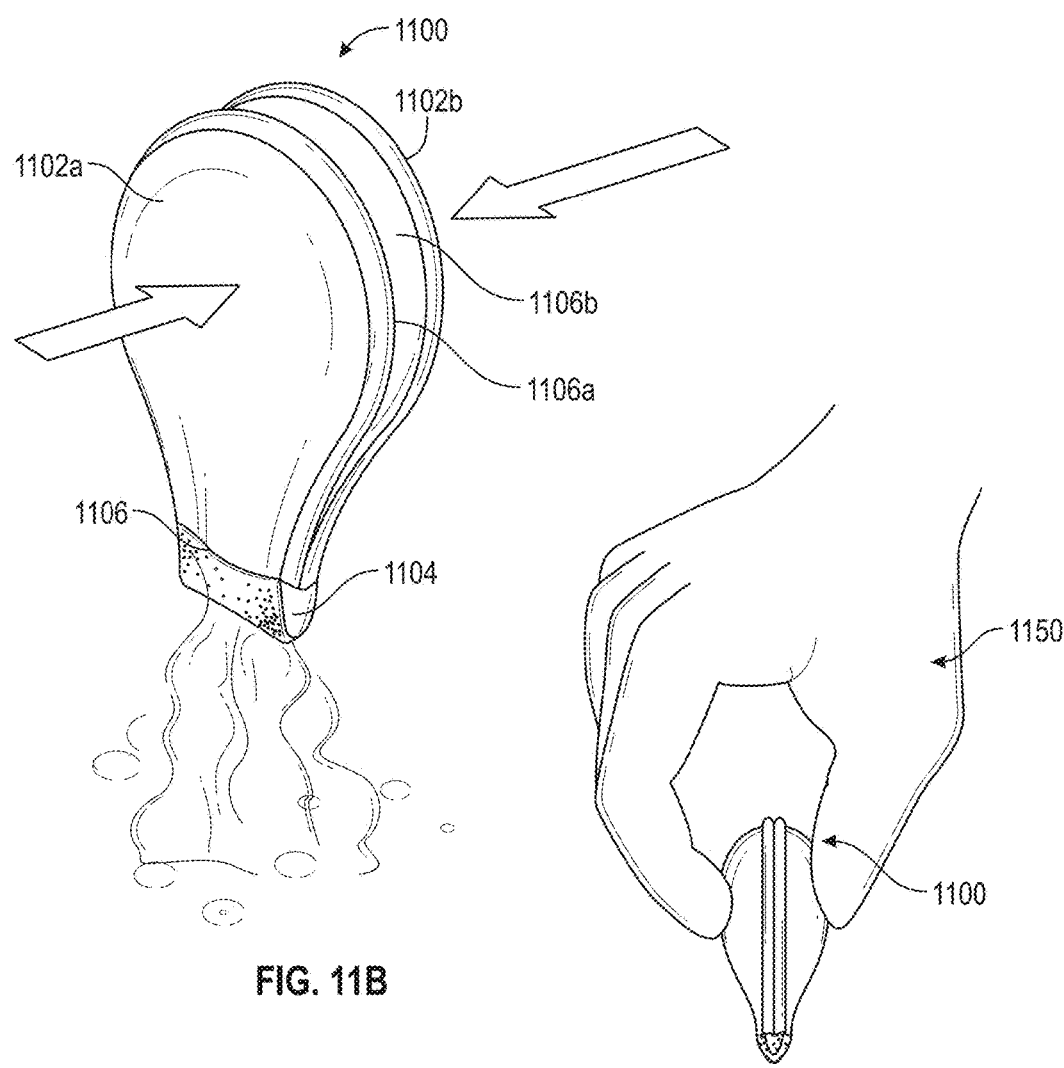
FIG. 11B
FIG. 11C

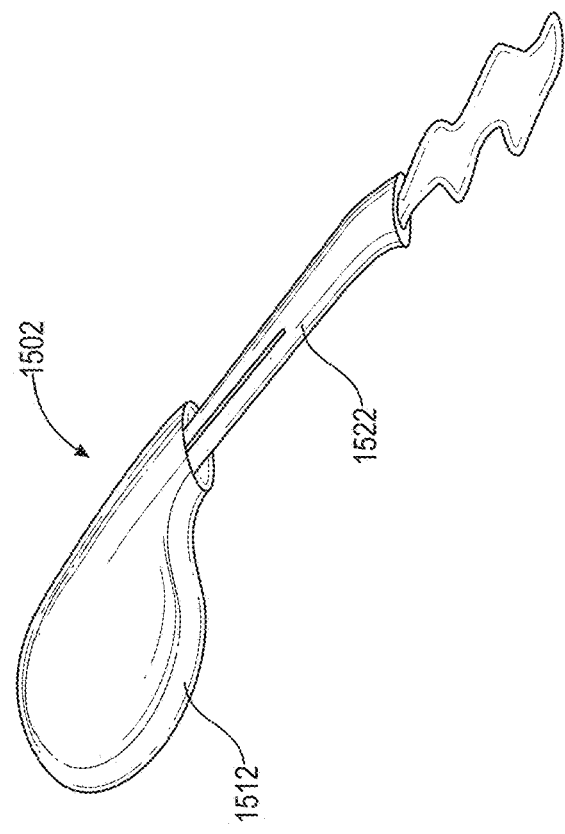
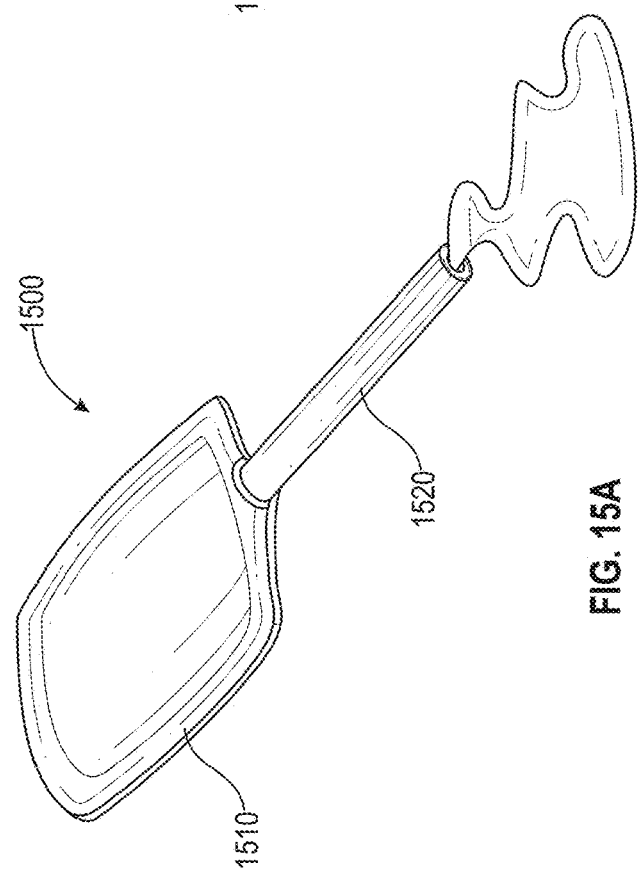

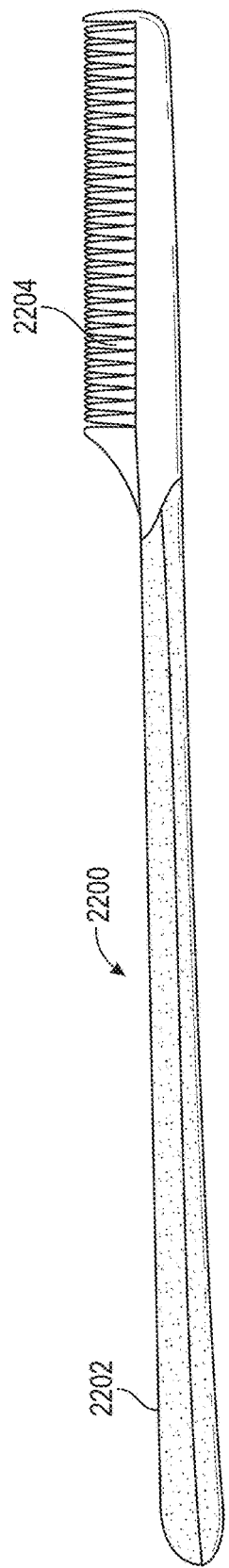
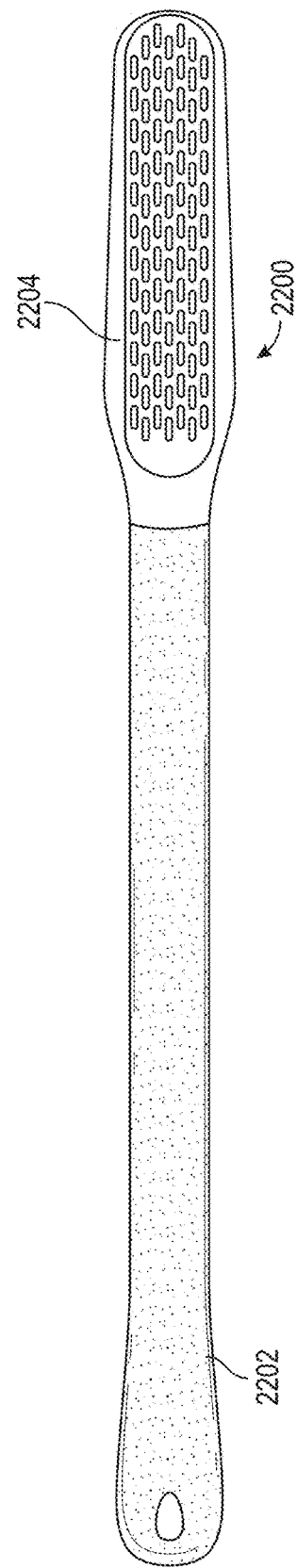
FIG. 22A
FIG. 22B

GEL APPLICATION SYSTEM

RELATED APPLICATIONS

The present disclosure claims priority to U.S. Provisional Patent Application No. 62/589,982, filed on Nov. 22, 2017, the entire contents of which are fully incorporated herein by reference.

BACKGROUND

Maintaining hygiene and cleanliness is a high priority for health care providers and procedures. One scenario in which hygiene may be compromised is when materials and instruments (e.g., gel or liquid containers and applicators) are reused on different patients. In addition, reusable medical instruments and materials may require intensive cleaning between uses and can be cumbersome for use by a health care provider.

SUMMARY

According to various embodiments, a gel application system is configured to be disposable such that it is not or need not be reused between more than one subject. In addition, according to various embodiments, the gel application system is configured for ease of use. As such, hygiene and cleanliness can be increased, while allowing health care providers to more efficiently and easily use the system.

According to various embodiments, a gel application system includes a container having an enclosed interior volume for containing a gel. An applicator is coupled to the container, for applying gel to a surface. A seal is provided between the container and the applicator. The seal has a first state in which it is configured to block the gel from exiting the gel application system. The seal has a second state in which it is configured to allow at least a portion of the gel to flow from the enclosed interior volume of the container to the applicator or to an environment exterior to the gel application system.

In various embodiments, the seal, when in the first state, provides a physical barrier for preventing the gel from flowing beyond the seal, and when in the second state, provides an opening to allow gel to pass the seal.

In various embodiments, the seal is made of a rigid material including one or more of a plastic, aluminum, steel, titanium, magnesium, metal alloy or other metal, composite material, carbon fiber, fiber glass, expanded foam, compression molded foam, stereolithography (SLA) or Fused Deposition Modeling (FDM)-made materials, Reaction Injection Molding (RIM) molding material, acrylonitrile butadiene styrene (ABS), thermoplastic olefin (TPO), nylon, polyvinyl chloride (PVC), or fiber reinforced resin.

In various embodiments, the seal is configured to be broken to open a pathway to allow the gel to exit the gel application system, wherein the seal is configured to withstand the flow of the gel when unbroken, yet brittle enough to enable a user to break the seal by applying predefined force to the seal.

In various embodiments, the seal may be broken or opened upon or in response to a gel pressure within the interior volume of the container reaching or exceeding a magnitude sufficient to cause the seal to break or open.

In various embodiments, the seal is configured to be break or open in response to a user squeezing and compressing the container by an amount that increases the gel pressure within the interior volume of the container sufficient to reach or exceed a threshold magnitude.

In various embodiments, the seal is configured to be break or open in response to a user puncturing the seal with an implement.

In various embodiments, the container is made from a single or uniform material and has no seams such that the container is airtight.

In various embodiments, the container is made from one or more of a polymer, a plastic, or a rubber material.

In various embodiments, the container is made of one or more materials connected and sealed at one or more seams to form the enclosed interior volume.

In various embodiments, the container is made of a material that is sufficiently flexible to allow a user to squeeze the container with manual force by hand, to compress the enclosed interior volume and apply or increase the pressure of the gel in the interior volume.

In various embodiments, the container is made of a material that is sufficiently resilient to allow the container to resume its shape before it is squeezed, once the manual force is withdrawn from the container.

In various embodiments, the gel includes ultrasound gel for use with ultrasound emitting devices, including Transcranial Doppler (TCD) devices.

In various embodiments, the container includes a section having a channel, the channel having a first end in gel flow communication with the interior volume of the container, the channel having a second end that is open or in gel flow communication with an outlet port through which gel may flow from the channel to the applicator or to discharge at least some of the gel from the gel application system.

In various embodiments, the seal is located within the channel.

In various embodiments, the applicator includes a hole through the applicator.

In various embodiments, the hole in the applicator is aligned with the channel such that at least a portion of the gel can flow from the interior volume of the container, through the channel, and through the applicator, to a free end of the applicator.

In various embodiments, the applicator includes a soft, flexible, or resilient material, including at least one of a closed cell foam, open cell foam, self-skinning open or closed cell foam material, or a cast, aerated, or extruded silicone or urethane, or polyurethane material.

In various embodiments, the applicator includes a hole through the applicator through which at least a portion of the gel can flow from the interior volume of the container, to a free end of the applicator.

In various embodiments, the applicator includes a plurality of bristles in a circular arrangement around the hole through the applicator.

In various embodiments, the applicator includes a plurality of bristles.

In various embodiments, the plurality of bristles are located in a circular arrangement around the hole defined by the applicator.

In various embodiments, the bristles include flexible, hair-like bristles having a diameter in the range of about 0.04 mm. to 3.0 mm.

In various embodiments, the system further includes an applicator stick attached to the container.

In various embodiments, the applicator stick has a generally elongated, rectangular shape corresponding to an elongated plate or flat stick shape, and has an outward-facing surface defining a platform for receiving at least some of the gel from the container.

In various embodiments, the applicator stick is made of a rigid wood, plastic, metal, ceramic, composite material, cardboard, or cardstock material.

In various embodiments, the applicator stick is formed as part of the container by molding the applicator stick onto a side of the container.

In various embodiments, the applicator stick includes an end portion that extends from the container.

Further embodiments relate to a method of making a gel application system including providing a container having an enclosed interior volume for containing a gel. The method further includes coupling an applicator coupled to the container, were the applicator is configured for applying gel to a surface. The method further includes providing a seal between the container and the applicator, were the seal has a first state in which it is configured to block the gel from exiting the gel application system, and where the seal has a second state in which it is configured to allow at least a portion of the gel to flow from the enclosed interior volume of the container to the applicator or to an environment exterior to the gel application system.

In various embodiments of the method, the seal, when in the first state, provides a physical barrier for preventing the gel from flowing beyond the seal, and when in the second state, provides an opening to allow gel to pass the seal.

In various embodiments of the method, the seal is made of a rigid material including one or more of a plastic, aluminum, steel, titanium, magnesium, metal alloy or other metal, composite material, carbon fiber, fiber glass, expanded foam, compression molded foam, stereolithography (SLA) or Fused Deposition Modeling (FDM)-made materials, Reaction Injection Molding (RIM) molding material, acrylonitrile butadiene styrene (ABS), thermoplastic olefin (TPO), nylon, polyvinyl chloride (PVC), or fiber reinforced resin.

In various embodiments of the method, the seal is configured to be broken to open a pathway to allow the gel to exit the gel application system, wherein the seal is configured to withstand the flow of the gel when unbroken, yet brittle enough to enable a user to break the seal by applying predefined force to the seal.

In various embodiments of the method, the seal may be broken or opened upon or in response to a gel pressure within the interior volume of the container reaching or exceeding a magnitude sufficient to cause the seal to break or open.

In various embodiments of the method, the seal is configured to be break or open in response to a user squeezing and compressing the container by an amount that increases the gel pressure within the interior volume of the container sufficient to reach or exceed a threshold magnitude.

In various embodiments of the method, the seal is configured to be break or open in response to a user puncturing the seal with an implement.

In various embodiments of the method, the container is made from a single or uniform material and has no seams such that the container is airtight.

In various embodiments of the method, the container is made from one or more of a polymer, a plastic, or a rubber material.

In various embodiments of the method, providing the container includes connecting and sealing one or more materials at one or more seams to form the enclosed interior volume.

In various embodiments of the method, the container is made of a material that is sufficiently flexible to allow a user to squeeze the container with manual force by hand, to compress the enclosed interior volume and apply or increase the pressure of the gel in the interior volume.

In various embodiments of the method, the container is made of a material that is sufficiently resilient to allow the container to resume its shape before it is squeezed, once the manual force is withdrawn from the container.

In various embodiments of the method, the gel includes ultrasound gel for use with ultrasound emitting devices, including Transcranial Doppler (TCD) devices.

In various embodiments of the method, providing the container includes providing a container section having a channel, the channel having a first end in gel flow communication with the interior volume of the container, the channel having a second end that is open or in gel flow communication with an outlet port through which gel may flow from the channel to the applicator or to discharge at least some of the gel from the gel application system.

In various embodiments of the method, providing the seal includes locating the seal within the channel.

In various embodiments of the method, the applicator includes a hole through the applicator.

In various embodiments of the method, the hole in the applicator is aligned with the channel such that at least a portion of the gel can flow from the interior volume of the container, through the channel, and through the applicator, to a free end of the applicator.

In various embodiments of the method, the applicator includes a soft, flexible, or resilient material, including at least one of a closed cell foam, open cell foam, self-skinning open or closed cell foam material, or a cast, aerated, or extruded silicone or urethane, or polyurethane material.

In various embodiments of the method, the applicator includes a hole through the applicator through which at least a portion of the gel can flow from the interior volume of the container, to a free end of the applicator.

In various embodiments of the method, the applicator includes a plurality of bristles in a circular arrangement around the hole through the applicator.

In various embodiments of the method, the applicator includes a plurality of bristles.

In various embodiments of the method, the plurality of bristles is located in a circular arrangement around the hole defined by the applicator.

In various embodiments of the method, the bristles include flexible, hair-like bristles having a diameter in the range of about 0.04 mm. to 3.0 mm.

In various embodiments, the method further includes attaching an applicator stick to the container.

In various embodiments of the method, the applicator stick has a generally elongated, rectangular shape corresponding to an elongated plate or flat stick shape, and has an outward-facing surface defining a platform for receiving at least some of the gel from the container.

In various embodiments of the method, the applicator stick is made of a rigid wood, plastic, metal, ceramic, composite material, cardboard, or cardstock material.

In various embodiments of the method, the applicator stick is formed as part of the container by molding the applicator stick onto a side of the container.

In various embodiments of the method, the applicator stick includes an end portion that extends from the container.

According to various further embodiments, a gel application system includes an applicator body having a first surface, a second surface and at least one opening extending through the applicator body from the first surface to the second surface. At least one gel packet is attached to the first surface of the applicator and defining an interior volume containing gel, the interior volume of the gel packet being in fluid flow communication with the at least one opening. The at least one gel packet is made of a material that has sufficient flexibility to allow a user to squeeze and compress the interior volume and expel gel through the at least one opening, by applying a compression force on the gel packet.

In various embodiments, the applicator body includes a generally rigid or partially rigid body having an elongated shape that defines a lengthwise dimension with a first end and a second end, and wherein the at least one opening is located closer to the first end than to the second end.

In various embodiments, the at least one opening includes a slot-shaped opening having an elongated shape with a lengthwise dimension extending along the lengthwise dimension of the applicator body.

In various embodiments, the gel packet includes a large volume end and a small volume end located opposite to the large volume end, wherein the large volume end of the gel packet is configured to retain a larger volume of gel relative to the small volume end of the gel packet.

In various embodiments, the large volume end of the gel packet is located adjacent to the second end of the applicator body, and the small volume end of the gel packet is located adjacent to the first end of the applicator body.

In various embodiments, the first surface of the applicator body includes a passage or groove extending along at least a portion of the length dimension of the applicator body, forming a channel for enhancing a flow of the gel from the large volume end of the gel packet to the at least one opening in the applicator body.

In various embodiments, the gel packet includes at least one sheet of flexible material sealed around a peripheral edge to the applicator body to form a flexible wall around one or more internal volumes that contain the gel between the sheet of flexible material and the applicator body.

In various embodiments, the at least one sheet of flexible material of the gel packet includes plastic, rubber or metal foil.

In various embodiments, the one or more internal volumes the gel packet are bordered by the flexible wall of the gel packet and the first surface of the applicator body.

In various embodiments, the one or more internal volumes the gel packet include one or more envelopes or enclosed pouches of flexible material adhered to the applicator.

In various embodiments, the at least one opening includes a plurality of slot-shaped openings, each having an elongated shape.

In various embodiments, the applicator body includes a generally rigid or partially rigid body having an elongated shape that defines a lengthwise dimension with a first end and a second end, and wherein the at least one opening includes a plurality of openings located closer to the first end than to the second end.

In various embodiments, a peel-off cover is attached to the applicator body to cover and seal the at least one opening to inhibit expulsion of gel from the at least one opening.

In various embodiments, the cover includes an adhesive that is sufficiently strong to hold the cover on the applicator body until a user manually removes the cover, by peeling the cover off of the applicator body to allow gel to be expelled from the at least one opening.

In various embodiments, the cover includes a sheet of material that covers at least a portion of the second surface of the applicator body and has a surface facing outward from the applicator body on which printed information is provided.

In various embodiments, the applicator body is transparent or partially transparent such that gel may be viewable along at least a portion of the applicator body.

In various embodiments, the applicator body has an elongated shape that defines a first end and a second end, wherein one or both of the first end and the second end are rounded or have rounded corners or edges.

In various embodiments, the gel application system further including at least one of a gel spreading mechanism on the applicator body for adjusting a placement and thickness of expelled gel, or a gel scraper on the applicator body for scraping expelled gel.

In various embodiments, the gel spreading mechanism is located along an outer edge of the applicator body.

In various embodiments, the applicator body has an elongated shape that defines a lengthwise dimension with a first end and a second end, wherein the at least one opening is located closer to the first end than to the second end, and wherein the gel spreading mechanism extends along an entire edge curvature of the first end of the applicator body.

In various embodiments, the gel spreading mechanism: (a) is affixed to or formed on the first surface of the applicator body, or (b) protrudes outward relative to the first surface of the applicator body.

In various embodiments, the gel spreading mechanism: (a) is affixed to or formed on the second surface of the applicator body, or (b) protrudes outward relative to the second surface of the applicator body.

In various embodiments, the gel spreading mechanism includes a soft material including at least one of rubber, closed cell foam, open cell foam, self-skinning open or closed cell foams, cast, aerated, or extruded silicone or urethane, or polyurethane.

In various embodiments, the gel spreading mechanism or the scraper includes a rigid material including at least one of plastic, rubber, silicon, metal, ceramic, composite material, wood, cardboard, or cardstock.

In various embodiments, the scraper protrudes outward relative to the first surface of the applicator body.

In various embodiments, the gel spreading mechanism protrudes outward relative to the second surface of the applicator body, and the scraper protrudes outward relative to the first surface of the applicator body.

In various embodiments, the gel spreading mechanism includes a soft material including at least one of rubber, closed cell foam, open cell foam, self-skinning open or closed cell foams, cast, aerated, or extruded silicone or urethane, or polyurethane; and the scraper includes a rigid material including at least one of plastic, rubber, silicon, metal, ceramic, composite material, wood, cardboard, or cardstock.

Further embodiments relate to a method of making a gel application system including providing an applicator body having a first surface, a second surface and at least one opening extending through the applicator body from the first surface to the second surface. The method further includes attaching at least one gel packet to the first surface of the applicator and defining an interior volume containing gel, the interior volume of the gel packet being in fluid flow communication with the at least one opening, wherein the at least one gel packet is made of a material that has sufficient flexibility to allow a user to squeeze and compress the interior volume and expel gel through the at least one opening, by applying a compression force on the gel packet.

In various embodiments of the method, the applicator body includes a generally rigid or partially rigid body having an elongated shape that defines a lengthwise dimension with a first end and a second end, and wherein the at least one opening is located closer to the first end than to the second end.

In various embodiments of the method, the gel packet includes a large volume end and a small volume end located opposite to the large volume end, wherein the large volume end of the gel packet is configured to retain a larger volume of gel relative to the small volume end of the gel packet.

In various embodiments of the method, the large volume end of the gel packet is located adjacent to the second end of the applicator body, and the small volume end of the gel packet is located adjacent to the first end of the applicator body.

Various embodiments of the method further includes providing a passage or groove in the first surface of the applicator body, the passage or groove extending along at least a portion of the length dimension of the applicator body to form a channel for enhancing a flow of the gel from the large volume end of the gel packet to the at least one opening in the applicator body.

In various embodiments of the method, the attaching at least one gel packet includes sealing at least one sheet of flexible material to the applicator body to form a flexible wall around one or more internal volumes that contain the gel between the sheet of flexible material and the applicator body.

In various embodiments of the method, the one or more internal volumes the gel packet are bordered by the flexible wall of the gel packet and the first surface of the applicator body.

In various embodiments of the method, the one or more internal volumes the gel packet include one or more envelopes or enclosed pouches of flexible material adhered to the applicator.

Various embodiments of the method further include attaching a peel-off cover to the applicator body to cover and seal the at least one opening to inhibit expulsion of gel from the at least one opening.

In various embodiments of the method, the peel-off cover includes a sheet of material that covers substantially the entire second surface of the applicator body.

In various embodiments of the method, the peel-off cover includes a sheet of material that covers at least a portion of the second surface of the applicator body and has a surface facing outward from the applicator body on which printed information is provided.

In various embodiments of the method, providing an applicator body includes providing an applicator body that is transparent or partially transparent such that the gel may be viewable along at least a portion of the applicator body.

Various embodiments of the method further include providing at least one of a gel spreading mechanism on the applicator body for adjusting a placement and thickness of expelled gel, or a gel scraper on the applicator body for scraping expelled gel.

In various embodiments of the method, the gel spreading mechanism is located along an outer edge of the applicator body.

In various embodiments of the method, the applicator body has an elongated shape that defines a lengthwise dimension with a first end and a second end, wherein the at least one opening is located closer to the first end than to the second end, and wherein the gel spreading mechanism extends along an entire edge curvature of the first end of the applicator body.

In various embodiments of the method, the gel spreading mechanism: (a) is affixed to or formed on the first surface of the applicator body, or (b) protrudes outward relative to the first surface of the applicator body.

In various embodiments of the method, the gel spreading mechanism: (a) is affixed to or formed on the second surface of the applicator body, or (b) protrudes outward relative to the second surface of the applicator body.

In various embodiments of the method, the gel spreading mechanism includes a soft material including at least one of rubber, closed cell foam, open cell foam, self-skinning open or closed cell foams, cast, aerated, or extruded silicone or urethane, or polyurethane.

In various embodiments of the method, the gel spreading mechanism or the scraper includes a rigid material including at least one of plastic, rubber, silicon, metal, ceramic, composite material, wood, cardboard, or cardstock.

In various embodiments of the method, the scraper protrudes outward relative to the first surface of the applicator body.

In various embodiments of the method, the gel spreading mechanism protrudes outward relative to the second surface of the applicator body, and the scraper protrudes outward relative to the first surface of the applicator body.

According to various further embodiments, a gel application system includes a barrier including a body having a first side and a second side. The gel applicator system further includes a first cover releasably affixed to the first side of the barrier, and a second cover releasably affixed to the second side of the barrier. The first and second covers are sealed with the barrier and form an interior volume containing a gel.

In various embodiments, an adhesive material is provided between each of the first and second covers and the body of the barrier, for releasably adhering the first and second covers to the body of the barrier.

In various embodiments, the adhesive material is configured such that at least some adhesive material remains on the first side of the body of the barrier after removal of the first cover, and the first side of the barrier is configured to be adhered to a surface by employing the at least some adhesive material that remains on the first side of the body of the barrier.

In various embodiments, at least one of the first and second covers includes a tab for allowing a user to grip the at least one cover, for peeling the at least one cover off of the body of the barrier to expose the gel contained by the barrier.

In various embodiments, each of the first and second covers includes a tab for allowing a user to grip the cover, for peeling the cover off of the body of the barrier to expose the gel contained by the barrier.

In various embodiments, each of the body of the barrier is made of at least one of a plastic, a rubber, a metal, a ceramic, a wood, a paper, a cardboard, a cardstock, or a composite material.

In various embodiments, each of the first and second covers is made of at least one of a plastic, a metal sheet or foil, a paper, or a composite material.

In various embodiments, the gel includes ultrasound gel for use with ultrasound emitting devices, including Transcranial Doppler (TCD) devices.

Further embodiments relate to a method of making a gel application system including providing a barrier including a body having a first side and a second side. The method further includes releasably affixing a first cover to the first side of the barrier, and releasably affixing a second cover to the second side of the barrier. The first and second covers are sealed with the barrier and form an interior volume containing a gel.

Various embodiments of the method further include providing an adhesive material between each of the first and second covers and the body of the barrier, for releasably adhering the first and second covers to the body of the barrier.

In various embodiments of the method, the adhesive material is configured such that at least some adhesive material remains on the first side of the body of the barrier after removal of the first cover, and the first side of the barrier is configured to be adhered to a surface by employing the at least some adhesive material that remains on the first side of the body of the barrier.

Various embodiments of the method further include providing a tab on at least one of the first and second covers for allowing a user to grip the at least one cover, for peeling the at least one cover off of the body of the barrier to expose the gel contained by the barrier.

Various embodiments of the method further comprise providing a tab on each of the first and second covers for allowing a user to grip the cover, for peeling the cover off of the body of the barrier to expose the gel contained by the barrier.

In various embodiments of the method, each of the body of the barrier is made of at least one of a plastic, a rubber, a metal, a ceramic, a wood, a paper, a cardboard, a cardstock, or a composite material.

In various embodiments of the method, each of the first and second covers is made of at least one of a plastic, a metal sheet or foil, a paper, or a composite material.

In various embodiments of the method, the gel comprises ultrasound gel for use with ultrasound emitting devices, including Transcranial Doppler (TCD) devices.

According to various further embodiments, a gel application system includes a container having an interior volume for containing gel. The container has a first end provided with a first opening and a second end provided with a second opening. A plunger extends through the first opening of the container. The plunger has a first end located within the interior volume of the container and a second end located outside of the container. The plunger is moveable in a first direction within the container to expel gel from the second opening in the second end of the container. The applicator is affixed to the second end of the container for receiving at least a portion of the gel expelled from the container.

In various embodiments, the first direction is a direction toward the second end of the container.

In various embodiments, the interior volume of the container is pre-filled with a pre-defined quantity of gel.

In various embodiments, the container comprises a generally cylindrical shaped barrel having an opening on a first end through which the plunger extends, and an opening on a second end through which gel from the interior volume of the container may be dispensed.

In various embodiments, the container is made of a transparent or partially transparent material that allows a user to view contents within the interior volume of the container, to view the amount of gel contained within the interior volume of the container.

In various embodiments, the container includes one or more markings along a length dimension, to define one or more volume levels (or amounts) of gel or other material contained in the interior volume of the container.

In various embodiments, the container includes a flange on or adjacent the first end of the container, the flange having a surface against which a user's fingers my press to provide leverage, while pushing the plunger.

In various embodiments, the applicator is made of at least one of a flexible or resilient closed cell foam, open cell foam, self-skinning open or closed cell foams, cast, aerated, or extruded silicone or urethane, or polyurethane material.

In various embodiments, the applicator has a wedge shape.

In various embodiments, the applicator has a first end and a second end, the second end of the applicator being affixed to the second end of the container, the second end of the applicator is thicker than the first end.

In various embodiments, the first end of the applicator defines a free or distal end.

In various embodiments, the plunger includes a handle for receiving a pushing force for moving the plunger towards the first end of the container.

In various embodiments, the applicator has a hole that is in gel flow communication with the opening in the second end of the container, through which the gel expelled container may flow.

In various embodiments, the applicator has a slot-shaped, elongated opening that is in gel flow communication with the opening in the second end of the container, through which the gel expelled container may flow.

Further embodiments relate to a method of making a gel application system comprising providing a container having an interior volume for containing gel. The container has a first end provided with a first opening and a second end provided with a second opening. The method includes extending a plunger extending through the first opening of the container. The plunger has a first end located within the interior volume of the container and a second end located outside of the container. The plunger is moveable in a first direction within the container to expel gel from the second opening in the second end of the container. The method further includes affixing an applicator to the second end of the container for receiving at least a portion of the gel expelled from the container.

In various embodiments of the method, the first direction is a direction toward the second end of the container.

In various embodiments of the method, the interior volume of the container is filled with a pre-defined quantity of gel.

In various embodiments of the method, the container comprises a generally cylindrical shaped barrel having an opening on a first end through which the plunger extends, and an opening on a second end through which gel from the interior volume of the container may be dispensed.

In various embodiments of the method, the container is made of a transparent or partially transparent material that allows a user to view contents within the interior volume of the container, to view the amount of gel contained within the interior volume of the container.

In various embodiments of the method, the container includes one or more markings along a length dimension, to define one or more volume levels (or amounts) of gel or other material contained in the interior volume of the container.

In various embodiments of the method, the container includes a flange on or adjacent the first end of the container, the flange having a surface against which a user's fingers my press to provide leverage, while pushing the plunger.

In various embodiments of the method, the applicator is made of at least one of a flexible or resilient closed cell foam, open cell foam, self-skinning open or closed cell foams, cast, aerated, or extruded silicone or urethane, or polyurethane material.

In various embodiments of the method, the applicator has a wedge shape.

In various embodiments of the method, the applicator has a first end and a second end, the second end of the applicator being affixed to the second end of the container, the second end of the applicator is thicker than the first end.

In various embodiments of the method, the first end of the applicator defines a free or distal end.

In various embodiments of the method, the plunger includes a handle for receiving a pushing force for moving the plunger towards the first end of the container.

In various embodiments of the method, the applicator has a hole that is in gel flow communication with the opening in the second end of the container, through which the gel expelled container may flow.

In various embodiments of the method, the applicator has a slot-shaped, elongated opening that is in gel flow communication with the opening in the second end of the container, through which the gel expelled container may flow.

According to further embodiments, a gel application system includes a container having an interior volume for containing gel. The container has a first end provided with a first opening and a second end provided with a second opening. A plunger extends through the first opening of the container. The plunger has a first end located within the interior volume of the container and a second end located outside of the container. The plunger is moveable in a first direction within the container to expel gel from the second opening in the second end of the container. An applicator including a generally flat or plate-like body of rigid or partially rigid material has a first end connected to the second end of the container. The applicator has a second end opposite the first end, the second end of the applicator defining a spreading edge or surface.

In various embodiments, the first end of the applicator includes a first state for dispensing gel and a second state for stamping or flattening dispensed gel.

In various embodiments, the applicator has a valve that has an open state and a closed state wherein, when the valve is in the open state, the valve allows a portion of the volume of the gel within the container to be expelled, and when the valve is in a closed state, the valve provides a pressing surface for manually pressing against a volume portion of gel that has been expelled.

In various embodiments, the pressing surface is configured sufficiently flat to provide a gel flattening or spreading operation to flatten or spread the volume portion of gel, when the surface is pressed against the volume portion of gel.

In various embodiments, the valve includes an outlet having one or more openings arranged over a defined area, through which a volume portion of the gel may be expelled when the valve is in the open state.

In various embodiments, each opening has a shape of one or more of a slot, a logo, a letter, a number or a word.

In various embodiments, the one or more openings are arranged or shaped to provide a pattern of openings over a defined area, to expel the volume portion of the gel from the outlet over an area of a surface corresponding to the defined area.

In various embodiments, when the valve is in the closed state, the one or more openings of the outlet are covered or closed, to inhibit the passage of gel through the one or more openings.

In various embodiments, the valve is operated to transition from the open state to the closed state by rotating a portion of the valve.

In various embodiments, the valve includes an outlet plate having one or more openings through the plate, the one or more openings being arranged over a surface area of the outlet plate, through which a volume portion of the gel may be expelled when the valve is in the open state.

In various embodiments, when the valve is in the closed state, the one or more openings of the outlet plate are covered or closed, to inhibit the passage of gel through the one or more openings.

In various embodiments, the valve includes a second plate arranged against and parallel to the outlet plate, where one or both of the second plate and the outlet plate are rotatable relative to each other between at least a first relative rotary position and a second relative rotary position.

In various embodiments, the second plate has an arrangement of openings or other pattern of one or more openings that correspond to or otherwise align with the one or more openings in the outlet plate to allow the passage of gel through the second plate and the outlet plate when the second plate and the outlet plate are in the first rotational position relative to each other, but that are offset from the one or more openings in the outlet plate and inhibit the passage of gel through the second plate and the outlet plate when the second plate and the outlet plate are in the second rotary position relative to each other.

In various embodiments, the outlet plate and the second plate may be held within an annular body that is affixed to the second end of the container and that supports one or both of the plates for rotational motion relative to each other.

In various embodiments, the interior volume of the container is filled with a pre-defined quantity of gel.

In various embodiments, the gel comprises ultrasound gel for use with ultrasound emitting devices, including Transcranial Doppler (TCD) devices.

In various embodiments, the container is made of a transparent or partially transparent material that allows a user to view contents within the interior volume of the container, to view the amount of gel contained within the interior volume of the container.

In various embodiments, the container includes one or more markings along a length dimension, to define one or more volume levels (or amounts) of gel or other material contained in the interior volume of the container.

Various further embodiments relate to a method of making a gel application system, where the method includes providing a container having an interior volume for containing gel, where the container has a first end provided with a first opening and a second end provided with a second opening. The method further includes extending a plunger through the first opening of the container, such that the plunger has a first end located within the interior volume of the container and a second end located outside of the container, where the plunger is moveable in a first direction within the container to expel gel from the second opening in the second end of the container. The method further includes connecting a first end of an applicator to the second end of the container, where the applicator includes a generally flat or plate-like body of rigid or partially rigid material. The method further includes providing a spreading edge or surface on a second end of the applicator, the second end of the applicator being opposite the first end, of the applicator.

In various embodiments of the method, the first end of the applicator includes a first state for dispensing gel and a second state for stamping or flattening dispensed gel.

In various embodiments of the method, the applicator has a valve that has an open state and a closed state wherein, when the valve is in the open state, the valve allows a portion of the volume of the gel within the container to be expelled, and when the valve is in a closed state, the valve provides a pressing surface for manually pressing against a volume portion of gel that has been expelled.

In various embodiments of the method, the pressing surface is configured sufficiently flat to provide a gel flattening or spreading operation to flatten or spread the volume portion of gel, when the surface is pressed against the volume portion of gel.

In various embodiments of the method, the valve includes an outlet having one or more openings arranged over a defined area, through which a volume portion of the gel may be expelled when the valve is in the open state.

In various embodiments of the method, each opening has a shape of one or more of a slot, a logo, a letter, a number or a word.

In various embodiments of the method, the one or more openings are arranged or shaped to provide a pattern of openings over a defined area, to expel the volume portion of the gel from the outlet over an area of a surface corresponding to the defined area.

In various embodiments of the method, when the valve is in the closed state, the one or more openings of the outlet are covered or closed, to inhibit the passage of gel through the one or more openings.

In various embodiments of the method, the valve is operated to transition from the open state to the closed state by rotating a portion of the valve.

In various embodiments of the method, the valve includes an outlet plate having one or more openings through the plate, the one or more openings being arranged over a surface area of the outlet plate, through which a volume portion of the gel may be expelled when the valve is in the open state.

In various embodiments of the method, when the valve is in the closed state, the one or more openings of the outlet plate are covered or closed, to inhibit the passage of gel through the one or more openings.

In various embodiments of the method, the valve includes a second plate arranged against and parallel to the outlet plate, where one or both of the second plate and the outlet plate are rotatable relative to each other between at least a first relative rotary position and a second relative rotary position.

In various embodiments of the method, the second plate has an arrangement of openings or other pattern of one or more openings that correspond to or otherwise align with the one or more openings in the outlet plate to allow the passage of gel through the second plate and the outlet plate when the second plate and the outlet plate are in the first rotational position relative to each other, but that are offset from the one or more openings in the outlet plate and inhibit the passage of gel through the second plate and the outlet plate when the second plate and the outlet plate are in the second rotary position relative to each other.

In various embodiments of the method, the outlet plate and the second plate may be held within an annular body that is affixed to the second end of the container and that supports one or both of the plates for rotational motion relative to each other.

Various embodiments of the method further comprise filling the interior volume of the container with a pre-defined quantity of gel.

In various embodiments of the method, the gel comprises ultrasound gel for use with ultrasound emitting devices, including Transcranial Doppler (TCD) devices.

According to further embodiments, a gel application system includes a container having an interior volume for containing gel. The container having a first end provided with a first opening and a second end provided with a second opening. A plunger extends through the first opening of the container. The plunger has a first end located within the interior volume of the container and a second end located outside of the container. The plunger is moveable in a first direction within the container to expel gel from the second opening in the second end of the container. An applicator includes a generally flat or plate-like body of rigid or partially rigid material that has a first end connected to the second end of the container. The applicator has a second end opposite the first end, the second end of the applicator defining a spreading edge or surface.

In various embodiments, the first end of the applicator is thinner in a width dimension than the second end of the applicator.

In various embodiments, the applicator body has a tapered shape that tapers from the thinner first end, toward the second end.

In various embodiments, the second end of the applicator has an edge feature on the spreading edge or surface, the edge feature configured to enhance the ability to spread gel.

In various embodiments, the edge feature is formed on and is unitary with the applicator, at the second end of the applicator.

In various embodiments, the edge feature is a separate element that is attached to the second end of the applicator by at least one of an adhesive, welding, thermal bonding, snap fitting, or friction or press fitting.

In various embodiments, the edge feature is a separate element that is molded or co-molded onto the body of the applicator.

In various embodiments, the edge feature includes one or more of an angled or a beveled edge, a stepped or a reduced width edge, or a blade or an edging strip made of silicon, plastic, rubber, metal, or ceramic.

In various embodiments, the edge feature includes a blade or an edging strip that is made of a material that is more flexible than the material of the rest of the applicator.

In various embodiments, the applicator has one or more interior channels having a first end in gel flow communication with the opening in the second end of the container, the one or more interior channels of the applicator extend along at least a portion of a length dimension of the applicator, from the first end of the applicator, to one or more outlet openings in the applicator.

In various embodiments, the one or more outlet openings are located on a first surface of the generally flat or plate-like body of the applicator.

In various embodiments, the applicator has a second surface facing opposite to the first surface, the second surface of the applicator being generally flat and devoid of outlet openings, for contacting and spreading gel.

In various embodiments, the one or more outlet openings includes a plurality of outlet openings of different sizes or shapes.

In various embodiments, the one or more outlet openings includes one or more slot shaped openings.

In various embodiments, the one or more outlet openings include a combination of one or more slot-shaped openings and one or more round openings.

In various embodiments, the one or more outlet openings includes a plurality of outlet openings arranged along a width dimension of the body of the applicator, so as to dispense gel over a band or area having a width dimension.

In various embodiments, the one or more outlet openings are arranged adjacent to and along the second end of the body of the applicator.

In various embodiments, the container includes a flange on or adjacent the first end of the container, the flange having a surface against which a user's fingers my press to provide leverage, while pushing the plunger.

In various embodiments, the container includes a second flange at or near the second end of the container, the second flange having a surface against which a user may engage one or more fingers of one hand, while engaging the plunger, to move the second end of the container toward the plunger.

In various embodiments, the interior volume of the container is pre-filled with a pre-defined quantity of gel.

In various embodiments, the gel comprises ultrasound gel for use with ultrasound emitting devices, including Transcranial Doppler (TCD) devices.

In various embodiments, the container is made of a transparent or partially transparent material that allows a user to view contents within the interior volume of the container, to view the amount of gel contained within the interior volume of the container.

In various embodiments, the container includes one or more markings along a length dimension, to define one or more volume levels (or amounts) of gel or other material contained in the interior volume of the container.

Various further embodiments relate to a method of making a gel application system, where the method includes providing a container having an interior volume for containing gel, the container having a first end provided with a first opening and a second end provided with a second opening; extending a plunger through the first opening of the container, such that the plunger has a first end located within the interior volume of the container and a second end located outside of the container, where the plunger is moveable in a first direction within the container to expel gel from the second opening in the second end of the container; connecting a first end of an applicator to the second end of the container, the applicator including a generally flat or plate-like body of rigid or partially rigid material; and providing a spreading edge or surface on a second end of the applicator, the second end of the applicator being opposite the first end of the applicator.

In various embodiments of the method, the first end of the applicator is thinner in a width dimension than the second end of the applicator.

In various embodiments of the method, the applicator body has a tapered shape that tapers from the thinner first end, toward the second end.

In various embodiments of the method, providing a spreading edge or surface comprises providing the second end of the applicator with an edge feature configured to enhance the ability to spread gel.

In various embodiments of the method, providing the second end of the applicator with an edge feature comprises forming the edge feature on and unitary with the applicator, at the second end of the applicator.

In various embodiments of the method, providing the second end of the applicator with an edge feature comprises providing the edge feature as a separate element and attaching the edge feature to the second end of the applicator by at least one of an adhesive, welding, thermal bonding, snap fitting, or friction or press fitting.

In various embodiments of the method, providing the second end of the applicator with an edge feature comprises providing the edge feature as a separate element and molding or co-molding the edge feature onto the body of the applicator.

In various embodiments of the method, the edge feature includes one or more of an angled or a beveled edge, a stepped or a reduced width edge, or a blade or an edging strip made of silicon, plastic, rubber, metal, or ceramic.

In various embodiments of the method, the edge feature includes a blade or an edging strip that is made of a material that is more flexible than the material of the rest of the applicator.

Various embodiments of the method further comprise providing the applicator with one or more interior channels having a first end in gel flow communication with the opening in the second end of the container, the one or more interior channels of the applicator extend along at least a portion of a length dimension of the applicator, from the first end of the applicator, to one or more outlet openings in the applicator.

In various embodiments of the method, the one or more outlet openings are located on a first surface of the generally flat or plate-like body of the applicator.

In various embodiments of the method, the applicator having a second surface facing opposite to the first surface, the second surface of the applicator being generally flat and devoid of outlet openings, for contacting and spreading gel.

In various embodiments of the method, the one or more outlet openings includes a plurality of outlet openings of different sizes or shapes.

In various embodiments of the method, the one or more outlet openings includes one or more slot shaped openings.

In various embodiments of the method, the one or more outlet openings include a combination of one or more slot-shaped openings and one or more round openings.

In various embodiments of the method, the one or more outlet openings includes a plurality of outlet openings arranged along a width dimension of the body of the applicator, so as to dispense gel over a band or area having a width dimension.

In various embodiments of the method, the one or more outlet openings are arranged adjacent to and along the second end of the body of the applicator.

Various embodiments of the method further comprise providing the container with a flange on or adjacent the first end of the container, the flange having a surface against which a user's fingers my press to provide leverage, while pushing the plunger.

Various embodiments of the method further comprise providing the container with a second flange at or near the second end of the container, the second flange having a surface against which a user may engage one or more fingers of one hand, while engaging the plunger, to move the second end of the container toward the plunger.

Various embodiments of the method further comprising filling the interior volume of the container with a pre-defined quantity of gel.

In various embodiments of the method, the gel comprises ultrasound gel for use with ultrasound emitting devices, including Transcranial Doppler (TCD) devices.

According to various further embodiments, a gel application system includes a bag made of flexible material. The bag has an enclosed interior volume containing a gel, and is flexible and configured to receive a squeezing force to compress the interior volume. The system further includes a spreader or scraper, wherein the spreader or scraper is attached to the bag, or wherein the gel application system further includes a head portion to which an end of the bag is adhered and to which the spreader or scraper is secured, the head portion having a gel slot in gel flow communication with the interior volume of the bag.

In various embodiments, the spreader or scraper is secured to an end of the head portion opposite to an end of the head portion that is adhered to the end of the bag.

In various embodiments, the head portion is made of at least one of a plastic, a rubber, a metal, a ceramic, or a composite material.

In various embodiments, the bag is made of at least one of a pliable plastic, a rubber, or a metal foil material.

In various embodiments, the spreader or scraper is made of at least one of a rubber, closed cell foam, open cell foam, self-skinning open or closed cell foams, cast, aerated, or extruded silicone or urethane, or polyurethane material.

In various embodiments, the spreader or scraper is made of at least one of a rigid plastic, silicon, rubber, metal, ceramic, composite material, wood, cardboard, or cardstock material.

In various embodiments, the gel in the bag comprises ultrasound gel for use with ultrasound emitting devices, including Transcranial Doppler (TCD) devices.

Further embodiments relate to a method of making a gel application system comprising providing a bag made of flexible material, where the bag has an enclosed interior volume containing a gel, and where the bag is flexible and configured to receive a squeezing force to compress the interior volume. The method further comprises attaching a spreader or scraper to the bag, or attaching the spreader or scraper to a head portion and attaching the head portion to the bag, the head portion or the bag having a gel slot in gel flow communication with the interior volume of the bag.

In various embodiments of the method, the spreader or scraper is secured to an end of the head portion opposite to an end of the head portion that is adhered to the end of the bag.

In various embodiments of the method, the head portion is made of at least one of a plastic, a rubber, a metal, a ceramic, or a composite material.

In various embodiments of the method, the bag is made of at least one of a pliable plastic, a rubber, or a metal foil material.

In various embodiments of the method, the spreader or scraper is made of at least one of a rubber, closed cell foam, open cell foam, self-skinning open or closed cell foams, cast, aerated, or extruded silicone or urethane, or polyurethane material.

In various embodiments of the method, the spreader or scraper is made of at least one of a rigid plastic, silicon, rubber, metal, ceramic, composite material, wood, cardboard, or cardstock material.

In various embodiments of the method, the gel in the bag comprises ultrasound gel for use with ultrasound emitting devices, including Transcranial Doppler (TCD) devices.

According to various embodiments, a further gel application system comprises a base providing a support structure having a first surface. The base has a central portion separating two side portions and is configured to fold across the central portion. One or more containers is supported by the first surface of the base, on one or both of the side portions of the base. Each container encloses a volume of gel. An applicator is supported at the central portion of the base.

In various embodiments, the base comprises a generally flat, plate-like or sheet-like structure.

In various embodiments, the one or more containers defines at least one first packet on one of the two side portions of the base, and at least one second packet on the other of the two side portions of the base.

In various embodiments, the applicator is located between the at least one first packet and the at least one second packet.

In various embodiments, the one or more containers comprises one or more sheets of flexible material that is sealed to the base to form a flexible wall around one or more internal volumes for containing gel between the sheet of flexible material and the base.

In various embodiments, the one or more sheets of flexible material comprises plastic, rubber or metal foil.

In various embodiments, the base is more rigid than the one or more sheets of flexible material.

In various embodiments, the one or more containers comprises one or more envelopes or enclosed pouches made of flexible material adhered to the base.

In various embodiments, each of the one or more containers is affixed to the base by adhesives, welding, bonding, one or more hooks and latches, or press fittings.

In various embodiments, the one or more containers is molded or co-molded with or on the base.

In various embodiments, the applicator is secured to the first surface of the base and is covered by at least one wall of the one or more containers when the gel application system is in an inactivated state, and the at least one wall of the one or more containers is configured to open and expose the applicator upon the base being folded across the central portion to place the gel application system in an activated state.

In various embodiments, the at least one wall of the one or more containers is configured to rupture or tear automatically upon the base being folded across the central portion to place the gel application system in the activated state.

In various embodiments, the applicator is secured to the second surface of the base and the base includes one or more openings or passages that allow gel to flow through the base to the applicator.

In various embodiments, the base has a second surface facing opposite the first surface, and is configured to fold across the central portion to a pivoted state in which the second surface of the two side portions of the base are pivoted toward each other, such that the one or more containers on the first surface of the base are pivoted to face outward from two sides of the folded base.

In various embodiments, in the pivoted state of the base, a user may apply a force to the one or more containers by squeezing the one or more containers to expel at least some of the gel onto the applicator.

In various embodiments, the base is formed as a single, continuous, uniform sheet or plate of material that is foldable at the center portion.

In various embodiments, the single sheet or plate of material includes a fold line across the center portion, the fold line including one or more of a marking, groove, indentation, or series of perforations, to identify a folding orientation or to increase the flexibility of the center portion.

In various embodiments, the base side portions are separate members that are connected together at the center portion by a hinge, seam or other connection structure that allows the base side portions to be pivoted relative to each other.

In various embodiments, each of the base side portions is wider than the central portion.

In various embodiments, the applicator includes a triangular or wedge-shaped body of foam material.

Further embodiments relate to a method of making a gel application system comprising providing a base as a support structure having a first surface. The base has a central portion separating two side portions. The base configured to fold across the central portion. The method further comprises supporting one or more containers by the first surface of the base, on one or both of the side portions of the base. The method further comprises enclosing a volume of gel in each container, and supporting an applicator at the central portion of the base.

In various embodiments of the method, the base comprises a generally flat, plate-like or sheet-like structure.

In various embodiments of the method, supporting the one or more containers comprises supporting at least one first packet on one of the two side portions of the base, and at least one second packet on the other of the two side portions of the base.

In various embodiments of the method, supporting the applicator comprises locating the applicator between the at least one first packet and the at least one second packet.

In various embodiments of the method, supporting the one or more containers comprises sealing one or more sheets of flexible material to the base to form a flexible wall around one or more internal volumes for containing gel between the sheet of flexible material and the base.

In various embodiments of the method, the one or more sheets of flexible material comprises plastic, rubber or metal foil.

In various embodiments of the method, the base is more rigid than the one or more sheets of flexible material.

In various embodiments of the method, supporting the one or more containers comprises adhering one or more envelopes or enclosed pouches made of flexible material to the base.

In various embodiments of the method, supporting the one or more containers comprises affixing each of the one or more containers to the base by adhesives, welding, bonding, one or more hooks and latches, or press fittings.

In various embodiments of the method, the supporting the one or more containers comprises molding or co-molding the one or more containers with or on the base.

In various embodiments of the method, the supporting the applicator comprises securing the applicator to the first surface of the base. In such embodiments, the method further comprises covering the applicator by at least one wall of the one or more containers when the gel application system is in an inactivated state, and configuring the at least one wall of the one or more containers to open and expose the applicator upon the base being folded across the central portion to place the gel application system in an activated state.

In various embodiments of the method, configuring the at least one wall of the one or more containers to open comprises configuring the at least one wall to rupture or tear automatically upon the base being folded across the central portion to place the gel application system in the activated state.

In various embodiments of the method, supporting the applicator comprises securing the applicator to the second surface of the base and the base includes one or more openings or passages that allow gel to flow through the base to the applicator.

In various embodiments of the method, the base has a second surface facing opposite the first surface, and is configured to fold across the central portion to a pivoted state in which the second surface of the two side portions of the base are pivoted toward each other, such that the one or more containers on the first surface of the base are pivoted to face outward from two sides of the folded base.

In various embodiments of the method, in the pivoted state of the base, a user may apply a force to the one or more containers by squeezing the one or more containers to expel at least some of the gel onto the applicator.

In various embodiments of the method, supporting the applicator comprises securing the applicator to the first surface of the base, and wherein the method further comprises covering the applicator by at least one wall of the one or more containers when the gel application system is in an inactivated state, and configuring the at least one wall of the one or more containers to open and expose the applicator upon the base being folded across the central portion to place the gel application system in an activated state.

In various embodiments of the method, configuring the at least one wall of the one or more containers to open comprises configuring the at least one wall to rupture or tear automatically upon the base being folded across the central portion to place the gel application system in the activated state.

In various embodiments of the method, providing the base comprises forming the base as a single, continuous, uniform sheet or plate of material that is foldable at the center portion.

In various embodiments of the method, providing the base further comprises providing the single sheet or plate of material with a fold line across the center portion, the fold line including one or more of a marking, groove, indentation, or series of perforations, to identify a folding orientation or to increase the flexibility of the center portion.

In various embodiments of the method, the base side portions are separate members that are connected together at the center portion by a hinge, seam or other connection structure that allows the base side portions to be pivoted relative to each other.

In various embodiments of the method, each of the base side portions is wider than the central portion.

In various embodiments of the method, the applicator includes a triangular or wedge-shaped body of foam material.

According to various further embodiments, a gel application system includes a gel packet made of a flexible material that forms an enclosed interior volume containing a gel. The gel packet has one or more tear sections, each tear section being configured to be at least partially torn away from the rest of the gel packet to form an opening into the interior volume of the gel packet through which gel may be expelled from the gel packet. In addition, either (a) the one or more tear sections includes a first tear section along an entire width dimension of the gel packet, and a second tear section across a corner of the gel packet, or (b) the gel packet can have a handle shape, or a shape that has a wider end portion for gripping and squeezing in a user's hand and a narrower end portion for extending out from the user's hand in a controllable direction, and wherein the one or more tear sections includes a tear section across the narrower end of the gel packet.

In various embodiments, the one or more tear sections includes the first tear section along the entire width dimension of the gel packet, and the second tear section across the corner of the gel packet, the gel packet has a generally rectangular shape, and the first tear section extends from one lengthwise edge to an opposite lengthwise edge of the generally rectangular shape, adjacent and along a widthwise edge of the generally rectangular shape.

In various embodiments, upon tearing away the first tear section, the interior volume of the gel packet is opened along the entire width dimension of the gel packet to allow a relatively high rate of gel flow from the gel packet.

In various embodiments, upon tearing away the second tear section, the interior volume of the gel packet is opened along the corner of the gel packet to allow a relatively low rate of gel flow from the gel packet.

In various embodiments, each of the first tear section and the second tear section includes one or more lines of perforations, indentations, thin regions or weaker regions on or in the flexible material of the gel packet, to enhance the ability of the gel packet to tear along the tear section.

In various embodiments, upon tearing away the second tear section, the interior volume of the gel packet is opened along the corner of the gel packet to allow a relatively low rate of gel flow from the gel packet.

In various embodiments, the gel packet has the handle shape, or the shape that has the wider end portion for gripping and squeezing in the user's hand and the narrower end portion for extending out from the user's hand in a controllable direction, wherein the one or more tear sections includes the tear section across the narrower end of the gel packet; and wherein the tear section across the narrower end of the gel packet includes one or more lines of perforations, indentations, thin regions or weaker regions on or in the flexible material of the gel packet, to enhance the ability of the gel packet to tear along the tear section.

In various embodiments, each tear section includes one or more lines of perforations, indentations, thin regions or weaker regions on or in the flexible material of the gel packet, to enhance the ability of the gel packet to tear along the tear section.

In various embodiments, the gel packet is made of one or more sheets of flexible material that is folded or sealed at peripheral edges to form the enclosed interior volume.

In various embodiments, the gel packet is made of one or more of a flexible plastic, rubber, or metal foil material.

In various embodiments, the gel packet is transparent or partially transparent to allow a user to view the gel inside of the gel packet from outside of the gel packet.

In various embodiments, the gel in the gel packet comprises ultrasound gel for use with ultrasound emitting devices, including Transcranial Doppler (TCD) devices.

Further embodiments relate to a method of making a gel application system comprising providing a gel packet made of a flexible material that forms an enclosed interior volume containing a gel. The method further comprises providing the gel packet with one or more tear sections, each tear section being configured to be at least partially torn away from the rest of the gel packet to form an opening into the interior volume of the gel packet through which gel may be expelled from the gel packet. In addition, either (a) the one or more tear sections includes a first tear section along an entire width dimension of the gel packet, and a second tear section across a corner of the gel packet, or (b) the gel packet can have a handle shape, or a shape that has a wider end portion for gripping and squeezing in a user's hand and a narrower end portion for extending out from the user's hand in a controllable direction, and wherein the one or more tear sections includes a tear section across the narrower end of the gel packet.

In various embodiments of the method, the one or more tear sections includes the first tear section along the entire width dimension of the gel packet, and the second tear section across the corner of the gel packet, the gel packet has a generally rectangular shape, and the first tear section extends from one lengthwise edge to an opposite lengthwise edge of the generally rectangular shape, adjacent and along a widthwise edge of the generally rectangular shape.

In various embodiments of the method, upon tearing away the first tear section, the interior volume of the gel packet is opened along the entire width dimension of the gel packet to allow a relatively high rate of gel flow from the gel packet.

In various embodiments of the method, upon tearing away the second tear section, the interior volume of the gel packet is opened along the corner of the gel packet to allow a relatively low rate of gel flow from the gel packet.

In various embodiments of the method, each of the first tear section and the second tear section includes one or more lines of perforations, indentations, thin regions or weaker regions on or in the flexible material of the gel packet, to enhance the ability of the gel packet to tear along the tear section.

In various embodiments of the method, upon tearing away the second tear section, the interior volume of the gel packet is opened along the corner of the gel packet to allow a relatively low rate of gel flow from the gel packet.

In various embodiments of the method, the gel packet has the handle shape, or the shape that has the wider end portion for gripping and squeezing in the user's hand and the narrower end portion for extending out from the user's hand in a controllable direction, and wherein the one or more tear sections includes the tear section across the narrower end of the gel packet; and wherein the tear section across the narrower end of the gel packet includes one or more lines of perforations, indentations, thin regions or weaker regions on or in the flexible material of the gel packet, to enhance the ability of the gel packet to tear along the tear section.

In various embodiments of the method, each tear section includes one or more lines of perforations, indentations, thin regions or weaker regions on or in the flexible material of the gel packet, to enhance the ability of the gel packet to tear along the tear section.

In various embodiments of the method, the gel packet is made of one or more sheets of flexible material that is folded or sealed at peripheral edges to form the enclosed interior volume.

In various embodiments of the method, the gel packet is made of one or more of a flexible plastic, rubber, or metal foil material.

In various embodiments of the method, the gel packet is transparent or partially transparent to allow a user to view the gel inside of the gel packet from outside of the gel packet.

In various embodiments of the method, the gel in the gel packet comprises ultrasound gel for use with ultrasound emitting devices, including Transcranial Doppler (TCD) devices.

According to further embodiments, a gel application system includes one or more gel packets, where each gel packet has an interior volume containing a gel. The gel application system further includes a gel packet container for receiving one of the one or more gel packets. The gel packet container has a force applicator to apply a compression force on the gel packet, when the gel packet is received by the gel packet container.

In various embodiments, the gel packet container has a base portion and a lid portion, the base portion having a receptacle for receiving the gel packet, the lid portion being configured to close over the base portion when the gel packet is received in the receptacle of the base portion.

In various embodiments, the force applicator is supported on the lid portion and is arranged to apply the compression force on the gel packet, when the gel packet is located within the gel packet container and the lid portion is closed over the base portion.

In various embodiments, the force applicator includes a squeezing member located on the interior-facing side of the lid portion, a trigger or handle located on the exterior-facing side of the lid portion, and a central section connecting the squeezing member and the trigger or handle together, wherein the central section of the force applicator extends through a slot-shaped opening in the lid portion and allows the force applicator to move along the length of the slot-shaped opening relative to the lid portion.

In various embodiments, the squeezing member is arranged to impart a compression force onto the gel packet, as the force applicator is moved along a direction of the slot-shaped opening in the lid portion, to cause at least some of the gel to be expelled through an outlet portion of the gel packet, when the outlet portion is open.

In various embodiments, the base portion and the lid portion are each made from one or more generally rigid plastic, metal, wood, cardboard, ceramic, or composite material.

In various embodiments, the lid portion is coupled to the base portion through a hinge portion.

In various embodiments, the hinge portion is a living hinge that is unitary with the base portion and the lid portion.

In various embodiments, the hinge portion includes a hinge structure that connects the lid portion with the base portion and allows the lid portion to pivot between an open and a closed position relative to the base portion.

In various embodiments, the base portion includes one or more registration features for alignment of the gel packet within the receptacle region.

In various embodiments, each gel packet includes one or more registration features for alignment of the gel packet within the receptacle region of the base portion.

In various embodiments, the base portion includes one or more first registration features, and each gel packet includes one or more second registration features for alignment of the gel packet within the receptacle region of the base portion.

In various embodiments, the one or more first registration features are configured to engage the one or more second registration features when the gel packet with the first registration features is properly aligned within a receptacle region of the base portion.

In various embodiments, the lid portion of the container is configured to be closed shut over the base portion to at least partially enclose the gel packet within the gel packet container, once the gel packet is properly aligned within the gel packet container.

In various embodiments, the second registration features include a pair of slot-shaped openings, and the first registration features include a pair of elongated protrusions configured to fit within the slot-shaped openings.

In various embodiments, the first and second registration features include one or more holes, openings, indentations or other mating shapes.

In various embodiments, the gel packet includes an outlet portion and a tear section that seals the outlet portion and inhibits gel from flowing from the interior volume of the gel packet, but that is removable by tearing to open the outlet portion and allow gel to be expelled from the interior volume of the gel packet.

In various embodiments, the gel packet includes a narrowed neck portion coupling the interior volume with the outlet portion, wherein the tear section is located across the neck portion.

In various embodiments, the one or more second registration features comprise at least one registration feature arranged adjacent each respective side of the narrowed or neck portion of the gel packet.

In various embodiments, the tear section includes one or more lines of perforations, indentations, thin regions or weaker regions on or in the gel packet, to enhance the user's ability to tear the tear section.

In various embodiments, the gel packet container includes an outlet opening through which gel expelled from the gel packet is expelled from the gel packet container, wherein the outlet opening of the gel packet container is formed as a gap or open space between the base portion and the lid portion, when the lid portion is closed over the base portion.

In various embodiments, the outlet opening of the container receives a portion of an outlet opening end of the gel packet, when the gel packet is properly received and registered within the container.

Various further embodiments relate to a method of making a gel application system, where the method comprises providing one or more gel packets, each gel packet having an interior volume containing a gel, providing a gel packet container for receiving one of the one or more gel packets, and coupling a force applicator to the gel packet container, to apply a compression force on the gel packet, when the gel packet is received by the gel packet container.

In various embodiments of the method, the gel packet container has a base portion and a lid portion, the base portion having a receptacle for receiving the gel packet, the lid portion being configured to close over the base portion when the gel packet is received in the receptacle of the base portion.

In various embodiments of the method, coupling the force applicator comprises supporting the force applicator on the lid portion and arranging the force applicator to apply the compression force on the gel packet, when the gel packet is located within the gel packet container and the lid portion is closed over the base portion.

In various embodiments of the method, the force applicator includes a squeezing member located on the interior-facing side of the lid portion, a trigger or handle located on the exterior-facing side of the lid portion, and a central section connecting the squeezing member and the trigger or handle together, wherein the central section of the force applicator extends through a slot-shaped opening in the lid portion and allows the force applicator to move along the length of the slot-shaped opening relative to the lid portion.

In various embodiments of the method, the squeezing member is arranged to impart a compression force onto the gel packet, as the force applicator is moved along a direction of the slot-shaped opening in the lid portion, to cause at least some of the gel to be expelled through an outlet portion of the gel packet, when the outlet portion is open.

A gel application system according to various further embodiments includes a flexible tip member having a first end, a second end and a gel flow channel connecting the first end and the second end, the second end of the flexible tip member having a self-closing outlet tip. The gel application system also includes a container defining an interior volume containing gel and having one end coupled in gel flow communication with the gel flow channel of the flexible tip member. The self-closing outlet tip is configured to remain in a closed (or sealed) state with sufficient force that gel is not able to pass through the outlet tip, unless an external force above a threshold is applied to the gel in the gel container.

In various embodiments, the container is made of a material that has sufficient flexibility to allow a user to squeeze and compress the interior volume and expel gel through the one end, into the gel flow channel of the flexible tip member, by applying a compression force on the container.

In various embodiments, the outlet tip is configured to open from its closed state to open to expel at least some of the gel upon the application of an external force above a threshold to the gel in the gel container.

In various embodiments, the outlet tip of the flexible tip member is made of a flexible silicone material.

In various embodiments, the outlet tip of the flexible tip member has a slot-shaped opening through which gel may be expelled.

In various embodiments, the flexible tip member is attached to the container by at least one of an adhesive, welding, thermal bonding, a threaded connector, a snap connector, or a friction or press fit connection.

In various embodiments, the container is made of one or more materials connected and sealed at one or more seams by one or more of vacuum sealing, heat sealing, or adhesive, to form an enclosed, hollow interior volume.

In various embodiments, the container is made of a single sheet of flexible material that is folded and sealed at its peripheral edge to form an enclosed interior volume for containing the gel.

In various embodiments, the container is made of two sheets of flexible material that are sealed together at their peripheral edges to form an enclosed interior volume for containing the gel.

In various embodiments, the gel comprises an ultrasound gel for use in connection with an ultrasound emitting device.

Various further embodiments relate to a method of making a gel application system, where the method comprises providing a flexible tip member having a first end, a second end and a gel flow channel connecting the first end and the second end, the second end of the flexible tip member having a self-closing outlet tip. The method further includes coupling one end of a container in gel flow communication with the gel flow channel of the flexible tip member, the container defining an interior volume containing gel, where the self-closing outlet tip is configured to remain in a closed (or sealed) state with sufficient force that gel is not able to pass through the outlet tip, unless an external force above a threshold is applied to the gel in the gel container.

In various embodiments of the method, the container is made of a material that has sufficient flexibility to allow a user to squeeze and compress the interior volume and expel gel through the one end, into the gel flow channel of the flexible tip member, by applying a compression force on the container.

In various embodiments of the method, the outlet tip is configured to open from its closed state to open to expel at least some of the gel upon the application of an external force above a threshold to the gel in the gel container.

In various embodiments of the method, the outlet tip of the flexible tip member is made of a flexible silicone material.

In various embodiments of the method, the outlet tip of the flexible tip member has a slot-shaped opening through which gel may be expelled.

In various embodiments of the method, coupling one end of the container with the flexible tip member comprises attaching the flexible tip member to the container by at least one of an adhesive, welding, thermal bonding, a threaded connector, a snap connector, or a friction or press fit connection.

In various embodiments of the method, the container is made of one or more materials connected and sealed at one or more seams by one or more of vacuum sealing, heat sealing, or adhesive, to form an enclosed, hollow interior volume.

In various embodiments of the method, the container is made of a single sheet of flexible material that is folded and sealed at its peripheral edge to form an enclosed interior volume for containing the gel.

In various embodiments of the method, the container is made of two sheets of flexible material that are sealed together at their peripheral edges to form an enclosed interior volume for containing the gel.

In various embodiments of the method, the gel comprises an ultrasound gel for use in connection with an ultrasound emitting device.

According to various further embodiments, a gel applicator comprises an applicator body including a generally rigid or partially rigid body having an elongated shape that defines a length dimension with a first end and a second end, a first surface and a second surface facing opposite the first surface. A gel controlling mechanism is secured or formed on or near the first end of the length dimension of the applicator body. The applicator body includes a handle at or near a second end of its length dimension. The handle is configured for a user to grip and hold the applicator body. The gel controlling mechanism includes one or more of: (a) a raised lip extending along an edge of the first end of the applicator body and along a portion of at least one side edge of the applicator body; (b) a side edge and an end edge that are extend along the first surface of the applicator body and form a generally flat, spatula-shaped end portion; or (c) a set of bristles.

In various embodiments, the first end of the applicator body is rounded such that the raised lip shape is rounded around the edge of the first end of the applicator body.

In various embodiments, the raised lip of the gel controlling mechanism includes a first length portion that extends along a first length of one side edge of the applicator body and a second length portion that extends along a second length of a second side edge of the applicator body. The second side edge of the applicator body is opposite to the first side of the applicator body.

In various embodiments, the second length is shorter than the first length.

In various embodiments, the second length equal to the first length.

In various embodiments, the first end and the second end of the applicator body have a rounded corner or edge.

In various embodiments, the applicator body has a recessed or indented surface having a shape for receiving a user's thumb at or near the second end of the applicator body.

In various embodiments, the applicator body includes one or more textured features within the recessed or indented surface for enhancing the user's grip.

In various embodiments, the applicator body includes a raised peripheral lip round its outer edge, or one or more protrusions or raised elements forming a textured surface adjacent the second end of the applicator body.

In various embodiments, the gel controlling mechanism: (a) is affixed to or formed on the first surface of the applicator body, or (b) protrudes outward relative to the first surface of the applicator body.

In various embodiments, the gel controlling mechanism comprises a soft material including at least one of rubber, closed cell foam, open cell foam, silicone, urethane, or polyurethane.

In various embodiments, the applicator body comprises a rigid material including at least one of plastic, rubber, silicon, metal, ceramic, composite material, wood, cardboard, or cardstock.

In various embodiments, the gel controlling mechanism is made of a silicone material.

Further embodiments relate to a method of making a gel applicator, where the method comprises providing an applicator body including a generally rigid or partially rigid body having an elongated shape that defines a length dimension with a first end and a second end, a first surface and a second surface facing opposite the first surface. The method further comprises securing a gel controlling mechanism on or near the first end of the length dimension of the applicator body. The applicator body includes a handle at or near a second end of its length dimension. The handle is configured for a user to grip and hold the applicator body. The gel controlling mechanism includes one or more of: (a) a raised lip extending along an edge of the first end of the applicator body and along a portion of at least one side edge of the applicator body; (b) a side edge and an end edge that are extend along the first surface of the applicator body and form a generally flat, spatula-shaped end portion; or (c) a set of bristles.

In various embodiments of the method, the first end of the applicator body is rounded such that the raised lip shape is rounded around the edge of the first end of the applicator body.

In various embodiments of the method, the raised lip of the gel controlling mechanism includes a first length portion that extends along a first length of one side edge of the applicator body and a second length portion that extends along a second length of a second side edge of the applicator body, the second side edge of the applicator body being opposite to the first side of the applicator body.

In various embodiments of the method, the second length is shorter than the first length.

In various embodiments of the method, the second length equal to the first length.

In various embodiments of the method, the first end and the second end of the applicator body have a rounded corner or edge.

In various embodiments of the method, the applicator body has a recessed or indented surface having a shape for receiving a user's thumb at or near the second end of the applicator body.

In various embodiments of the method, the applicator body includes one or more textured features within the recessed or indented surface for enhancing the user's grip.

In various embodiments of the method, the applicator body includes a raised peripheral lip round its outer edge, or one or more protrusions or raised elements forming a textured surface adjacent the second end of the applicator body.

In various embodiments of the method, securing the gel controlling mechanism comprises affixing the gel controlling mechanism to or forming the gel controlling mechanism on the first surface of the applicator body.

In various embodiments of the method, the gel controlling mechanism comprises a soft material including at least one of rubber, closed cell foam, open cell foam, self-skinning open or closed cell foams, cast, aerated, or extruded silicone or urethane, or polyurethane.

In various embodiments of the method, the applicator body comprises a rigid material including at least one of plastic, rubber, silicon, metal, ceramic, composite material, wood, cardboard, or cardstock.

In various embodiments of the method, the gel controlling mechanism is made of a silicone material.

BRIEF DESCRIPTION OF THE FIGURES

Features and aspects will become apparent from the following description and the accompanying example embodiments shown in the drawings, which are briefly described below.

FIG. 1A illustrates a top view of a gel application system according to various embodiments.

FIG. 1B illustrates a front view of the gel application system shown in FIG. 1A according to various embodiments.

FIG. 2A illustrates a top view of a gel application system according to various embodiments.

FIG. 2B illustrates a front view of the gel application system shown in FIG. 2A according to various embodiments.

FIG. 5B illustrates an exploded view of a gel application system according to various embodiments.

FIGS. 6C-6I illustrate perspective views of gel application systems according to various embodiments.

FIG. 9E illustrates a side view of a gel application system according to various embodiments.

FIG. 9F illustrates a side view of a portion of an applicator of the gel application system shown in FIG. 9E.

FIG. 11A illustrates a side view of a gel application system that is inactive according to various embodiments.

FIG. 11B and FIG. 11C illustrate perspective views of the gel application system shown in FIG. 11A that is activated according to various embodiments.

FIG. 15A, FIG. 15B, FIG. 15C, FIG. 15D, FIG. 15E and FIG. 15F illustrate perspective views of various gel application systems according to various embodiments.

FIG. 22A, FIG. 22B, FIG. 22C, and FIG. 22D illustrate various views of a gel applicator according to various embodiments.

DETAILED DESCRIPTION

Figure 3A:
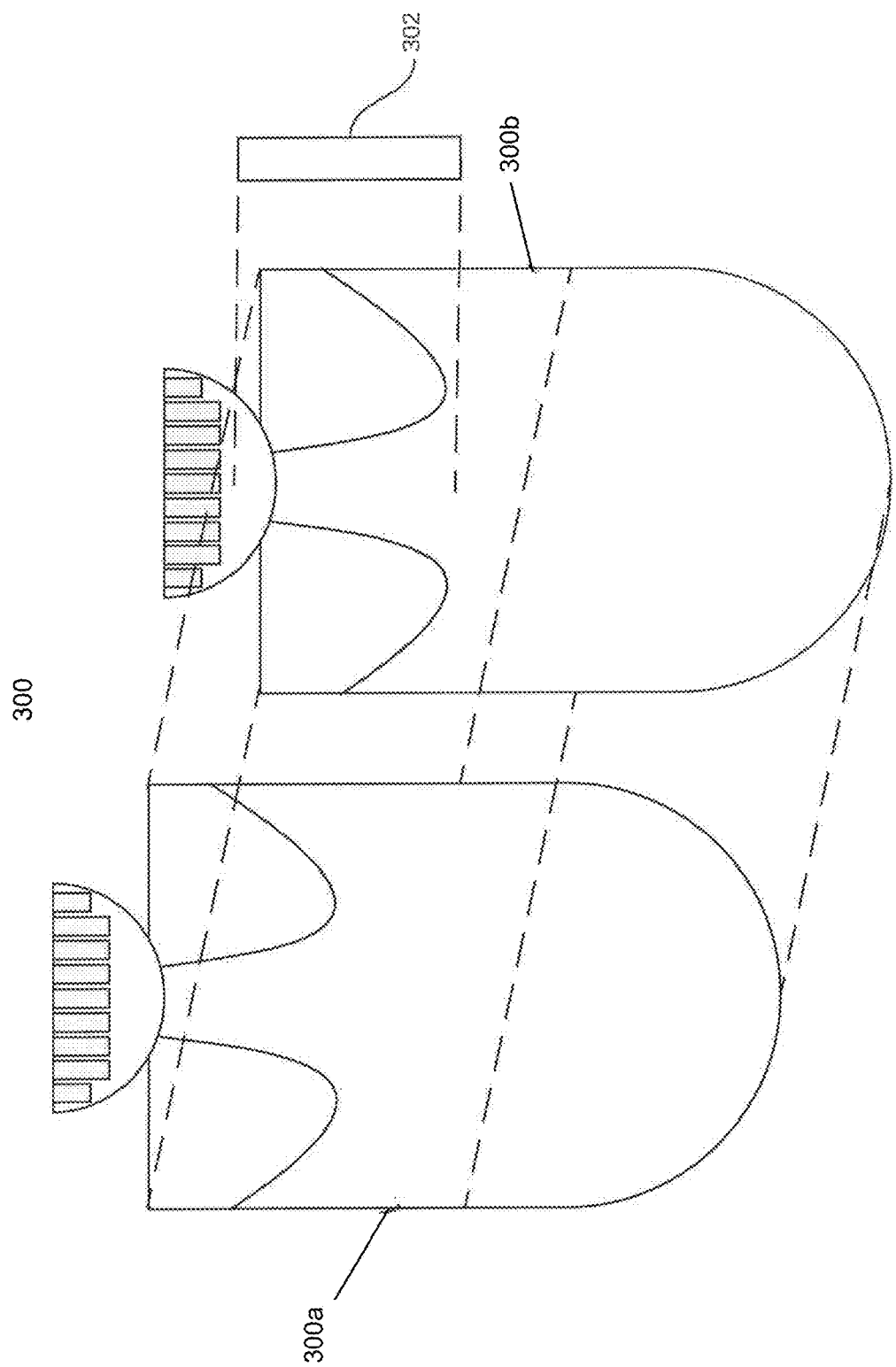
FIG. 3A illustrates a plurality of components of a gel application system according to various embodiments.

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various embodiments, reference is made to the accompanying drawings which form a part hereof and in which are shown, by way of illustration, specific embodiments that may be practiced. It is to be understood that other embodiments may be utilized, and structural changes may be made without departing from the scope of the various embodiments disclosed in the present disclosure.

In some embodiments, gel application systems are disposable and provide increased ease of use. Accordingly, in some embodiments, health care providers dispose of (or otherwise do not reuse) gel containers after a single use on a single patient or subject, thereby decreasing risk of the spread of bacteria. Furthermore, certain embodiments are configured to provide a user-friendly packaging that includes different components for administering gel onto a subject (e.g., the gel itself, an applicator, and the like), healthcare providers can more quickly and easily administer health care to patients. In addition, by providing a predetermined amount of gel within each disposable gel application system appropriate for conducting a healthcare procedure, a healthcare provider does not have to determine or measure an amount of gel to apply to a subject, and can therefore focus on other more significant aspects of the healthcare procedure.

FIG. 1A illustrates a top view of a gel application system 100 according to various embodiments. FIG. 1B illustrates a front view of the gel application system 100 shown in FIG. 1A according to various embodiments.

In some embodiments, the gel application system 100 includes a container 102, a pre-measured amount of gel 104, a seal 106, an applicator 108, and a channel 110, in a single tool or device, for ease of use. The container 102 defines an enclosed, pocket-like, hollow interior volume for containing the gel 104 therein. In some embodiments, the container 102 is made from a single or uniform material and has no seams such that the container 102 is airtight. In some embodiments, the container 102 is made from any suitable material for retaining the gel 104, such as, but not limited to, polymer, plastic, rubber, and the like. In other embodiments, the container 102 is made of one or more materials connected and sealed at one or more seams to form an enclosed, hollow interior volume. For example, the container 102 may be sealed along the edges thereof by any suitable mechanism including, but not limited to vacuum sealing, heat sealing, and the like. In some embodiments, the container 102 is made of a material that is sufficiently flexible to allow a user to squeeze the container 102 with manual force (such as by hand), to compress the pocket-like hollow interior and apply or increase the pressure of the fluid (or gel) in the pocket-like hollow interior. In some embodiments, the container 102 is made of a material that is also sufficiently resilient to allow the container 102 to resume its shape (the shape before it is squeezed), once squeezing pressure is withdrawn from the container.

In some embodiments, the gel 104 includes a suitable gel used in conjunction with healthcare, including, but not limited to, ultrasound gel used in connection with ultrasound emitting devices (e.g., Transcranial Doppler (TCD) devices). In other embodiments, the gel 104 may be other suitable gel, liquid, powder, composite material, or the like, for other types of procedures.

In some embodiments, the container 102 further includes a section having a channel 110. The channel 110 has a first end in gel or fluid flow communication with the interior volume of the pocket of the container 102. The channel 110 has a second end that is open to (or in gel or fluid flow communication with) an outlet port through which gel may flow from the channel to the applicator 108 or to the environment external to the container 102, to discharge the gel 104 from the gel application system 100. The seal 106 is located within the channel 110. In other examples, the seal 106 may be located on or adjacent one of the first or second ends of the channel 110. The seal 106 has a first state, in which it is configured to block the gel 104 from exiting the gel application system 100 through the channel 110. For example, the seal 106, when in the first state, can provide a physical barrier for preventing the gel 104 from flowing beyond the seal 106. The seal 106 has a second state, in which it is configured to allow gel 104 to pass through the channel 110, from the interior volume (or pocket), to and out of the outlet port. In some embodiments, the seal 106 is configured to be broken to open the pathway of the channel 110 to allow the gel 104 to exit the gel application system 100. In some embodiments, the seal 106 is strong enough to withstand the flow of the gel 104 when unbroken, yet brittle enough to enable a user to break the seal 106 by applying force thereto.

In some embodiments, the seal 106 is made from any suitable rigid material, such as, but not limited to, hard plastic, metals, aluminum, steel, titanium, magnesium, various alloys, rigid plastics, composites, carbon fiber, fiber glass, expanded foam, compression molded foam, stereolithography (SLA) or Fused Deposition Modeling (FDM)-made materials, Reaction Injection Molding (RIM) molding, acrylonitrile butadiene styrene (ABS), thermoplastic olefin (TPO), nylon, polyvinyl chloride (PVC), fiber reinforced resins, or the like. In other embodiments, the seal 106 may be made of a material having some flexibility, but being sufficiently rigid to open, break or rupture upon receiving a sufficient force as described herein. In some embodiments, a user breaks the seal 106 by snapping the seal 106 into two or more pieces, by puncturing the seal 106 with a tool or finger that applies a force on the seal 106, or by any other suitable implementation for allowing flow of the gel 104 through the channel 110. In some embodiments, the seal 106 may be broken (or otherwise opened) upon and in response to a user inserting a tool (such as, but not limited to a needle or other puncturing tool) into the channel 110 a sufficient distance to contact and puncture (or otherwise open) the seal 106. In some embodiments, the seal 106 may be broken (or otherwise opened) upon or in response to a fluid (or gel) pressure within the interior volume of the container 102 reaching or exceeding a sufficient threshold magnitude to cause the seal 106 to break (or otherwise open). In particular embodiments, the seal 106 may be broken (or otherwise opened) upon or in response to a user squeezing and compressing the container 102 by an amount that increases the fluid (or gel) pressure within the interior volume of the container 102 sufficient to reach or exceed the threshold magnitude.

In some embodiments, the seal 106 may include a valve or other suitable structure that is selectively opened (or opened and closed), in response to fluid (or gel) pressure within interior volume (pocket) of the container being greater than a defined threshold magnitude. In such embodiments, the valve may be a manually operated valve that includes a manual operator located on the container 102 or the applicator 104 that allows a user to selectively and manually open the valve. In yet other embodiments, the valve may include an electronic, magnetic, or electromagnetic valve that is operated by an electronic, magnetic or electromagnetic controller, to selectively open.

In some embodiments, the applicator 108 is attached to the container 102. In some embodiments, the applicator 108 is permanently attached to the container 102, for example, by welding, adhesive, one or more hooks and latches, press fittings, or the like. In other embodiments, the applicator 108 is releasably attached to the container 102, for example, by snap fittings, screw fittings, and the like. In some embodiments, the applicator 108 includes a soft, flexible, or resilient material, such as, but not limited to, closed cell foam, open cell foam, self-skinning open or closed cell foams, cast, aerated, or extruded silicone or urethane, polyurethane, or the like. In some embodiments, the applicator 108 includes a hole through the applicator material. The hole is aligned with the channel 110 such that the gel 104 can travel from within the container 102, through the channel 110, and through the applicator 108, to the free end of the applicator 108. Accordingly, the gel 104 can be excreted onto the applicator 108 so that a user can apply the gel 104 onto a subject using the applicator 108. In other embodiments, the gel 104 is discharged directly onto a subject.

In some embodiments, the hole through the applicator 108 is of a suitable size for allowing the gel 104 to pass through the applicator 108. The hole can be relatively large (e.g., to allow a relatively high gel flow rate through the applicator) or relatively small (e.g., to allow a relatively low gel flow rate through the applicator), depending on the application of use of the gel application system 100. In some embodiments, the hole is located in the center of the applicator 108. In other embodiments, the hole is located at other suitable positions with respect to the applicator 108, such as, but not limited to, along an edge thereof. In other embodiments, the hole is located in the container 102 (at the second end of the channel 110), separate from and above or below the applicator 108.

Accordingly, in some embodiments, a user of the gel application system 100 breaks (or otherwise opens) the seal 106 to allow flow of the gel 104 from within the container 102 through the channel 110. Then, the user is able to squeeze the gel 104 out through the channel 110 onto a subject or onto the applicator 108. The user then uses the applicator 108 to spread or otherwise apply the gel 104 onto a subject (e.g., onto a side of the subject's head).

FIG. 2A illustrates a top view of a gel application system 200 according to various embodiments. FIG. 2B illustrates a front view of the gel application system 200 shown in FIG. 2A according to various embodiments.

In some embodiments, the gel application system 200 includes a container 102, gel 104 and a seal 106, which may be the same or similar to those components of the gel application system 100. However, the gel application system 200 includes an applicator 202 that is different from the applicator 108 of the system 100. In particular, the gel application system 200 includes a brush-like applicator 202 that includes a plurality of bristles 204. In some embodiments, the applicator 202 has a hole in fluid (or gel) flow communication with the channel 110 such that the gel 104 may be discharged from the container 102, onto a patient or subject or onto the bristles 204 for application on the patient or subject. In some embodiments, the bristles 204 are configured to move the hair of a subject so as to clear the area of the subject that is to receive the gel 104 (e.g., to clear a temporal window of the subject).

In some embodiments, the bristles 204 are located in a circular arrangement around the hole defined by the applicator 202. In other embodiments, the bristles 204 are arranged in any other suitable shaped arrangements, such as, but not limited to, a triangle, a square, an ellipse, and the like. The bristles 204 may be connected to the applicator 202 by any mechanism, including but not limited to adhering or embedding one end of each of the bristles 204 to the applicator 202. A second (or distal) end of each of the bristles faces outward and is free to contact the skin or surface of a patient or subject.

In some embodiments, the size of the bristles 204 range from relatively thick comb-like bristles to relatively fine hair-like bristles, depending on the desired application. As non-limiting examples, bristles 204 can have a diameter in the range of about 0.04 mm. to about 3.0 mm. In other examples, the bristles 204 can be thinner than about 0.04 mm. or thicker than about 3.0 mm. The bristles 204 may be relatively flexible, so as to bend, when pressed against a patient or subject. In some embodiments, the bristles 204 are made from any suitable material for adjusting a subject's hair and/or for applying the gel 104 to the subject, such as, but not limited to, plastic, metal, nylon, animal hair, carbon fiber, and the like.

Figure 3B:
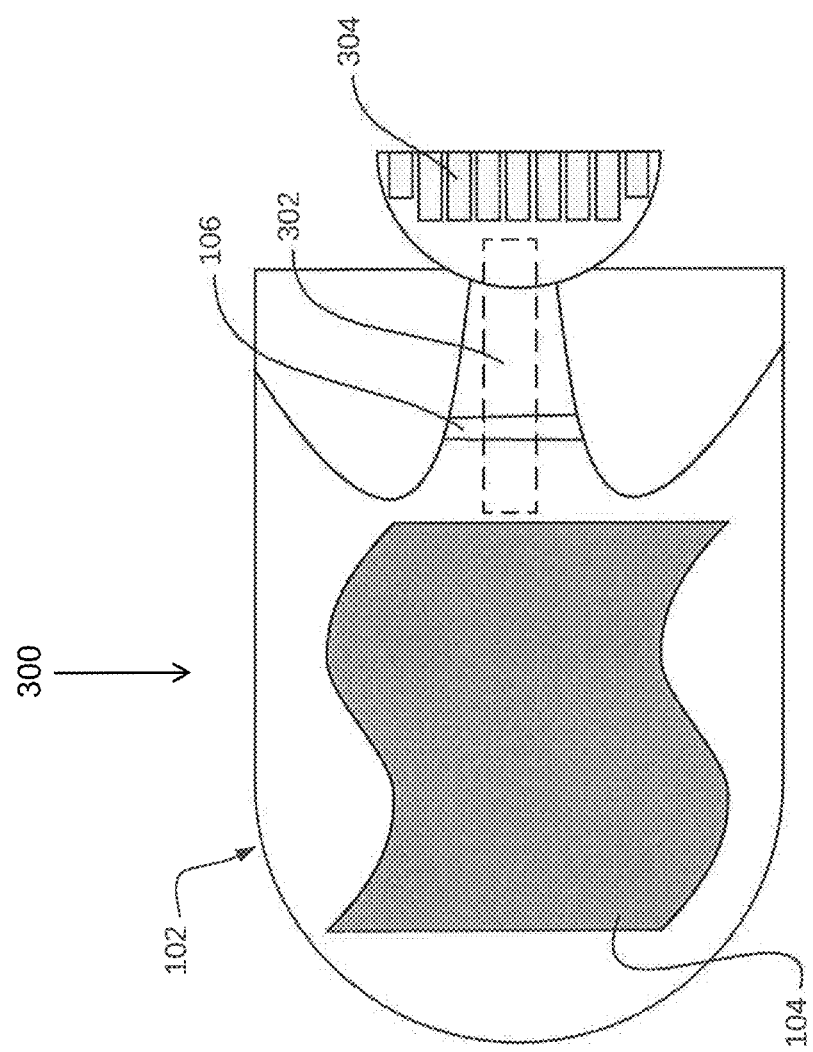
FIG. 3B illustrates a top view of the components of the gel application system shown in FIG. 3A after manufacturing according to various embodiments.
Figure 3C:
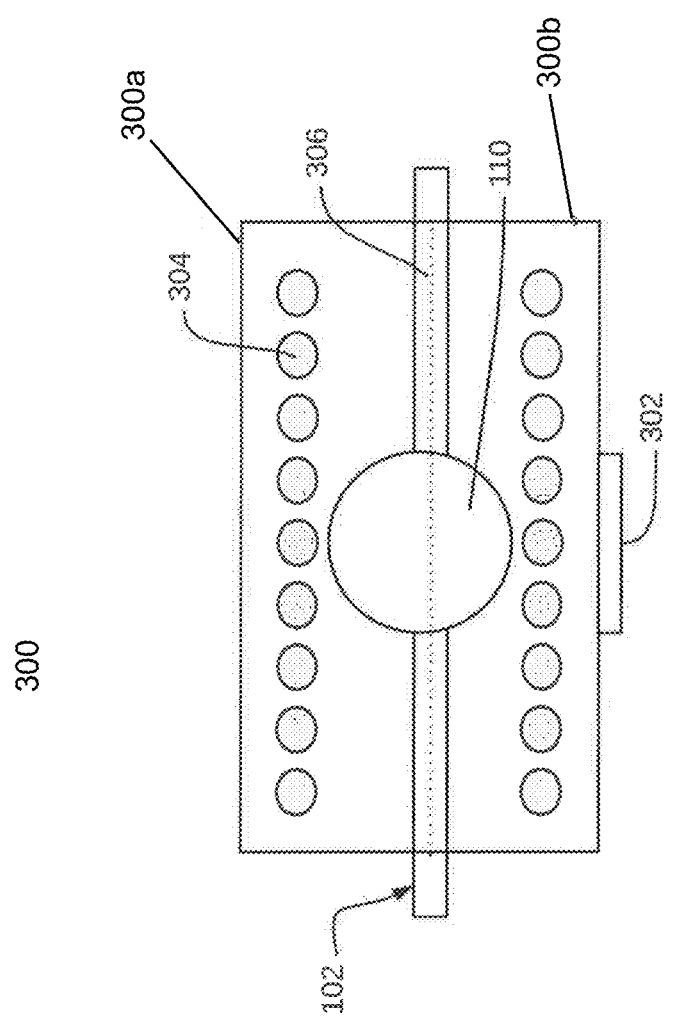
FIG. 3C illustrates a front view of the gel application system shown in FIG. 3B according to various embodiments.

FIG. 3A illustrates a plurality of components 300a, 300b of a gel application system 300 according to various embodiments. FIG. 3B illustrates a top view of the components of the gel application system 300 shown in FIG. 3A after manufacturing and assembly according to various embodiments. FIG. 3C illustrates a front view of the gel application system 300 shown in FIG. 3B according to various embodiments. In some embodiments, the gel application system 300 includes a container 102, gel 104 and a seal 106, which may be similar to those components of the gel application system 100. However, the gel application system 300 also includes a further applicator, in the form of an applicator stick 302.

In some embodiments, the gel application system 300 is made from the plurality of components including a first side component 300a, a second side component 300b, and the applicator stick 302. In such embodiments, the first side component 300a, the second side component 300b, and the applicator stick 302 are connected together and form the gel application system 300. In some embodiments, the first side component 300a and the second side component 300b are identical components, with each of the first side component 300a and the second side component 300b including about half of a container (e.g., the container 102). The first side component 300a and the second side component 300b connect together at peripheral edges to form the hollow volume (or pocket) between the side components 300a and 300b, for receiving gel 104. In certain examples, each of the first side component 300a and the second side component 300b include half of an applicator including a row (or a plurality of rows) of bristles 304. In some embodiments, the first side component 300a and the second side component 300b are affixed together by any suitable method, including, but not limited to, adhesive bonding, vacuum sealing, thermos sealing, and the like.

In some embodiments, the applicator stick 302 has a generally elongated, rectangular shape (corresponding to an elongated plate or flat stick shape), and has an outward-facing surface that can define a platform for receiving at least some of the gel 104 discharged from the container 102. Once some or all of the gel 104 is discharged from the container 102 onto the applicator stick 302 or directly onto the patient or subject (or on both the applicator stick 302 and the patient or subject), a user can apply and spread the gel 104 onto a patient or subject via the applicator stick 302. In some embodiments, the applicator stick 302 is made from any suitable rigid material for applying the gel 104 to a subject, such as, but not limited to, wood, plastic, metal, ceramic, composite material, cardboard, cardstock, and the like. In some embodiments, the applicator stick 302 is securely affixed to the container 102 by any suitable means, such as, but not limited to, welding, adhesive, one or more hooks and latches, press fittings, or the like. In other embodiments, the applicator stick 302 may be formed as part of the container 102 (or as part of the second side component 300b), for example, by molding the applicator stick onto the side (or side component) of the container 102. In some embodiments, a first end portion of the applicator stick 302 is affixed to the second side component 300b of the container 102, while a second end portion of the applicator stick 302 extends from (and is not further affixed) to the container 102 (e.g., such that the second portion of the applicator stick 302 is sufficiently free from the container 102 to allow gel 104 to be easily dispersed onto the applicator stick 302 and applied to a subject). In some embodiments, the second end of the applicator stick 302 has rounded corners or rounded edges (or both), to minimize sharp corners or edges.

In some embodiments, the gel application system 300 includes a plurality of bristles 304 (e.g., similar to bristles 204, as described above) configured to contact and adjust hair of a patient or subject, to clear an area for applying the gel 104. In the example of FIG. 3C, the bristles 304 are arranged in two, generally parallel rows, with one row arranged on one side of the channel 110 and the other row arranged on the opposite side of the channel 110. Thus, the first side component 300a includes a first row of bristles 304, and the second side component 300b includes a second row of bristles 304. In other embodiments, more than one row of bristles 304 may be provided on each side component 300a and 300b. In yet other embodiments, other arrangements of bristles may be provided at one or both side components 300a and 300b. In some embodiments, the gel application system 300 defines a seam or connection line 306, where the first side component 300a and the second side component 300b connect to each other. The seam or connection line 306 extends along the length dimension of the gel application system 300.

Figure 4:
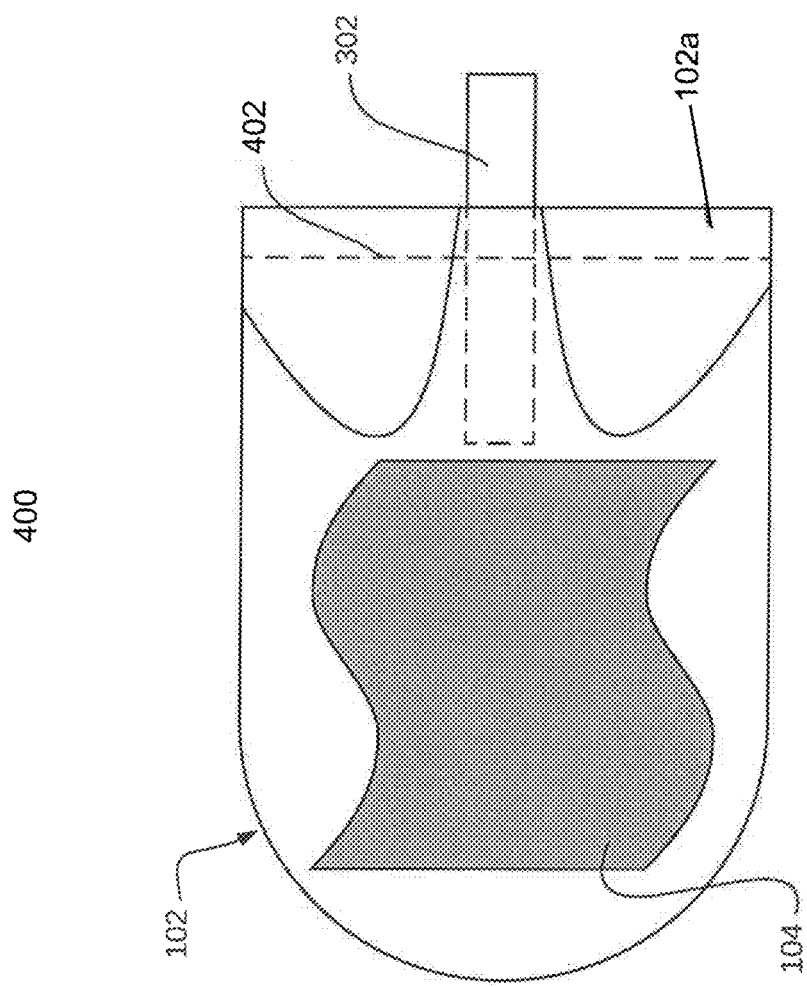
FIG. 4 illustrates a top view of a gel application system according to various embodiments.

FIG. 4 illustrates a top view of a gel application system 400 according to various embodiments. In some embodiments, the gel application system 400 includes a container 102 and gel 104 which may be similar to those components of the gel application system 100. In some embodiments the gel application system 400 may include a seal (not shown in FIG. 4), similar to the seal 106 in the gel application system 100.

In some embodiments, the gel application system 400 includes the applicator stick 302, which may be similar to the applicator stick 302 of the gel application system 300. In some embodiments, the gel application system 400 does not include the plurality of bristles 304 discussed above with respect to the gel application system 300.

In some embodiments, the container 102 (and the gel 104 therein) is sealed on one end by a tear section 102a of material that is connected to, but separated from the rest of the container 102, through a perforated portion (such as a line 402 of perforations in the material of the container 102). In some embodiments, the tear section 102a forms an end barrier that blocks the gel 104 from flowing out of the container 102 through the channel 110. However, to enable the flow of the gel 104 out of the container 102 through the channel 110, a user may rip the tear section 102a from the container 102 at the perforated line 402, to open the second end of the channel 110 such that the gel 104 can be dispersed from the container, onto a patient or subject, or onto the applicator stick 302 (or both).

Figure 5A:
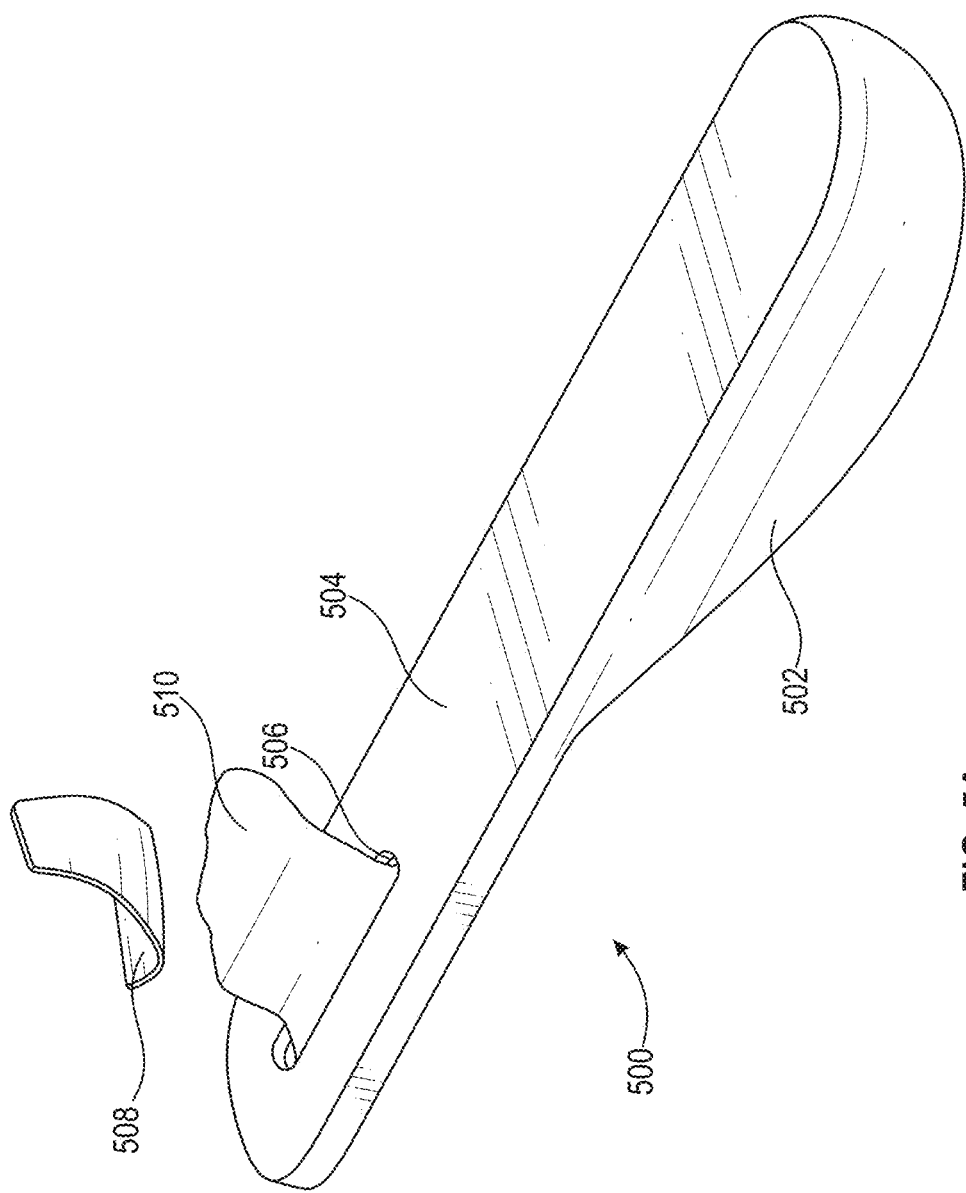
FIG. 5A illustrates a perspective view of a gel application system according to various embodiments.

FIG. 5A illustrates a perspective view of a gel application system 500 according to various embodiments. FIG. 5B illustrates an exploded view the gel application system 500 shown in FIG. 5A.

In some embodiments, the gel application system 500 includes a gel packet 502 and an applicator 504. The gel packet 502 is configured to define an enclosed, interior volume (within the gel packet 502, or between the gel packet 502 and the applicator 504) that is configured to retain gel (e.g., ultrasound gel, as described herein with respect to gel 104). In some embodiments, the gel packet 502 includes a container made from any suitable material for retaining the gel, such as, but not limited to, the material of the container 102, as described herein. In some embodiments, the gel packet 502 may be composed of one sheet (or a plurality of sheets) of flexible material, such as, but not limited to plastic, rubber, metal foil, or the like, that is (are) sealed around a peripheral edge to the applicator 504 to form a flexible wall around one or more internal volumes for containing gel between the sheet of flexible material and the applicator 504. In such embodiments, the one or more internal volumes the gel packet 502 may be bordered by the flexible wall of the gel packet 502 and a first surface of the applicator 504. In other embodiments, the gel packet 502 may have other suitable forms including, but not limited to one or more envelopes or enclosed pouches of flexible material adhered to the applicator 504.

In some embodiments, the gel packet 502 is made of a material that has sufficient flexibility to allow a user to squeeze and compress the interior volume, for example, by applying a force on the gel packet 502 with the user's hand, thumb or finger, while gripping and holding the gel application system 500 with the same hand. In some embodiments, the gel packet 502 is affixed (such as, permanently affixed) to the first surface of the applicator 504, for example, but not limited to, by welding, adhesive, one or more hooks and latches, press fittings, or the like. In some embodiments, the gel packet 502 may be molded onto the applicator 504. For example, the gel packet 502 may be molded with the applicator 504, and of the same material as the applicator. Alternatively, the gel packet 502 may be a separate material that is co-molded with, or over-molded onto the applicator 504. In some embodiments, the gel packet 502 includes a large volume end 502a (the end on the right side of FIGS. 5A and 5B) that is configured to retain a larger volume of gel 510, relative to the opposite, smaller volume end 502b (the end on the left side of FIGS. 5A and 5B) of the gel packet 52. Accordingly, the gel located at the large volume end 502a (e.g., in a default or resting state) can be guided with precision, including the flow rate of the gel, towards the end of the gel packet 502 via the small volume end 502b due to the transition from the large volume end 502a to the smaller volume end 502b of the gel packet 502. In some embodiments, more than one (a plurality of) gel packets 502 are affixed to the first surface of the applicator 504.

In some embodiments, the applicator 504 of the gel application system 500 comprises a generally rigid or partially rigid body such as, but not limited to an applicator stick that may be made of a similar material as the applicator stick 302, described above. In some embodiments, the applicator 504 defines a slot 506 (or a plurality of slots) extending through the applicator 504, and open on a second surface of the applicator 504 that faces opposite to the first surface on which the gel packet 502 is affixed. The slot 506 is located adjacent or below the smaller volume end portion of the gel packet 52 (the left end in FIGS. 5A and 5B). In some embodiments, the applicator 504 includes one or more gel slots 506, where a user is able to select and open one or more of the gel slots as desired, or partially open one or more of the gel slots.

In some embodiments, the body of the applicator 504 has an elongated shape that defines a first end and a second end. One or both of the first end and the second end may be rounded or have rounded corners or edges (or both), to avoid sharp corners or edges. In some embodiments, the slot 506 is located on an end portion adjacent the first end (for example, a top end) of the elongated shape of the applicator 504. In some embodiments, the large volume end 502a of the gel packet 502 is located on an end portion adjacent the second end (for example, a bottom end) of the elongated shape of the applicator 504. However, in other embodiments, the location of the slot 506 and the large volume end 502a of the gel packet 502 may be reversed relative to the above-described locations.

In some embodiments, gel 510 that is stored or retained within the gel packet 502 is configured to be discharged from the gel packet 502, through the gel slot 506 (e.g., onto a patient or subject), when the gel slot 506 is opened. Accordingly, in some embodiments, the interior volume of the gel packet 502 is in fluid (or gel) flow communication with the gel slot 506, to enable flow of the gel 510 from the gel packet 502 through the gel slot 506. Accordingly, once the gel slot 506 is opened, a user may regulate the dispensing rate of gel through the slot 506 by applying pressure to (for example, by squeezing and compressing the large volume end 502a of the gel packet 502), to force a desired volume of gel from the larger volume portion of the gel packet 502 to the smaller volume portion of the gel packet 502 and, then, out through the slot 506 in the applicator 504. The location of the slot 506 under the smaller volume portion 502b of the gel packet 502 can provide the user with a greater amount of control over the dispensing rate, by limiting the dispensing rate, as compared to an embodiment in which the slot 506 is located under the larger volume portion 502a of the gel packet 502. However, in other embodiments, one or more slots 506 may be located in the applicator 504, under the larger volume portion of the gel packet 502.

In some embodiments, the surface of the applicator 504 adjacent the gel packet 502 forms a passage or groove 512 along the length dimension of the applicator 504, that serves as a channel for enhancing control of fluid (or gel) flow from the large volume end 502a of the gel packet 502 to the slot 506 in the applicator 504. In some embodiments, the passage or groove has one end that is open to the slot 506.

In some embodiments, the gel application system 500 includes a closing mechanism, such as, but not limited to a peel-off cover 508 configured to attach to the applicator 504 (on a surface facing opposite the surface on which the gel packet 502 is located), to cover and seal the gel slot 506 such that the gel 510 cannot be discharged therefrom. The cover 508 may be made of any suitable material such as, but not limited to a plastic, metal sheet or foil, paper, composite material, or the like. The cover 508 (or the applicator 504, or both) may include an adhesive that is sufficiently strong to hold the cover 508 in place until a user manually removes the cover 508, by peeling the cover 508 off of the applicator 504. As such, in some embodiments, once a user removes (e.g., peels off) the cover 508, flow of the gel 510 out of the gel application system 500 is enabled. In some embodiments, a surface of the cover 508 facing the applicator 504 includes an adhesive layer such that the cover 508 is affixed to the applicator 504 and covers the gel slot 506. In other embodiments, other slot closing mechanisms may be used to allow a user to selectively open the slot 506 from a closed state. For example, in some embodiments, a slot closing mechanism may include one or more of a pivotal, rotatable, or sliding panel or door, that pivots, rotates or slides between a first position in which it blocks the slot and inhibits gel from being expelled through the slot, and a second position in which it opens the slot and allows gel to be expelled through the slot. In such embodiments, the panel or door may include or be coupled to a tab or trigger that can be engaged by a user to move the panel or door between the first and second positions. In yet other embodiments, a slot closing mechanism may include a cork or stopper that selectively fits at least partially in or over the slot, to selectively close the slot and inhibit the passage of gel through the slot, and that can be removed from the slot to selectively open the slot and allow the passage of gel through the slot.

In some embodiments, a user may use the gel application system 500 by peeling off the cover 508 to open the gel slot 506. Then, the user squeezes the large volume portion of the gel packet 502 to selectively discharge the gel 510 from the gel slot 506 onto a patient or subject (e.g., onto a head of the subject for use with a TCD device) or on the applicator 504 itself (e.g., by turning the gel application system 500 upside down to allow the discharged gel to seep onto the surface of the applicator 504 for application of the gel onto a desired surface. In some embodiments, once some or all of the gel 510 is discharged onto the patient or subject, the applicator 504 is utilized to move the gel 510 into desired locations or to spread the gel 510 evenly or as desired on the subject.

In FIGS. 5A and 5B, the gel slot 506 is located adjacent, but spaced from a distal end edge of the applicator 504 and is oriented such that the length dimension of the slot 506 extends along (or parallel to) the length dimension of the body of the applicator 504. In other embodiments, the gel slot 506 is positioned at other locations or orientations on the applicator 504, such as, but not limited to, at or long a distal end edge of the applicator 504. In some embodiments, the gel slot 506 is positioned in different orientations, such as, but not limited to, lengthwise along the applicator 504, widthwise (e.g., perpendicular to lengthwise) across the applicator 504, diagonally, or other suitable location or arrangement. In some embodiments, the applicator 504 defines a plurality of gel slots 506. In certain embodiments, a plurality of gel slot 506 having a corresponding plurality of different shapes is provided, such as, but not limited to, a circle, a star, a cross, and the like. In certain embodiments, a plurality of gel slot 506 having a corresponding plurality of different opening sizes (for providing a plurality of different dispensing rates at a given fluid pressure) is provided. In embodiments in which multiple slots are provided, each slot may include a separate cover 508 (or other closing mechanism) to allow the user to selectively open (or leave closed) one or more of the plurality of slots or portions thereof.

In some embodiments, the body of the applicator 504 is transparent or partially transparent, such that a user can view the amount of remaining gel or the flow of gel 510 along at least a portion of the applicator 504.

FIGS. 6A-6I illustrate perspective views of gel application systems that may be similar to the gel application system 500, but include further features or differences described herein and shown in the drawings.

Figure 6B:
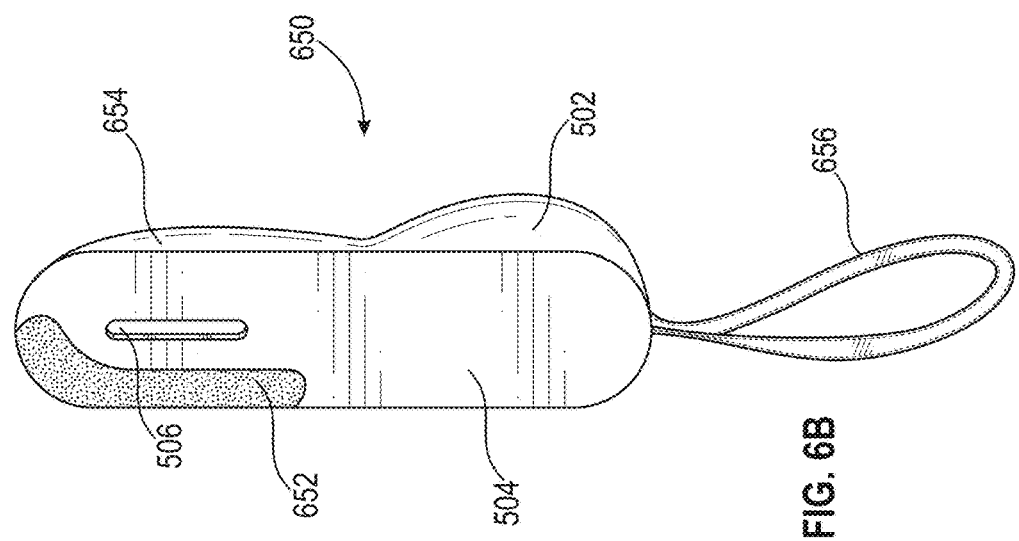
FIG. 6B illustrates a perspective view of a gel application system according to various embodiments.
Figure 6A:
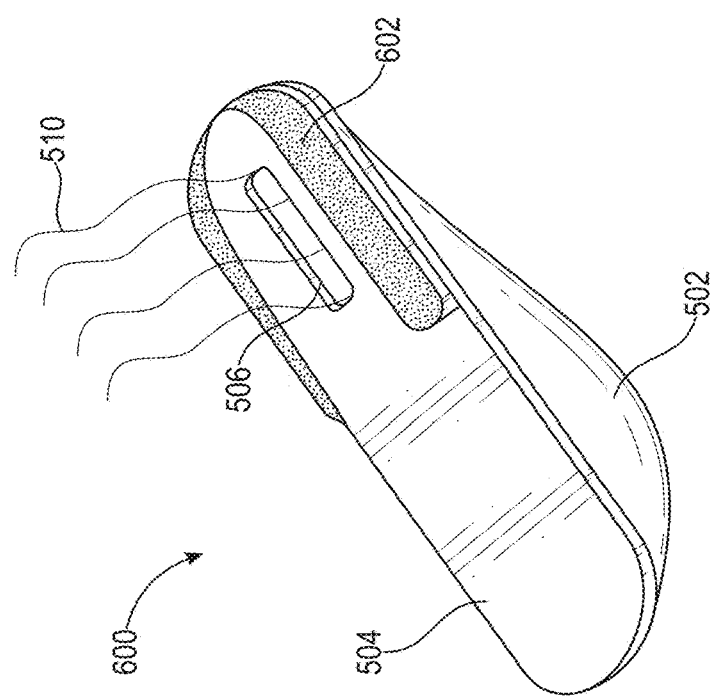
FIG. 6A illustrates a perspective view of a gel application system according to various embodiments.

For example, FIG. 6A illustrates a perspective view of a gel application system 600 according to various embodiments.

In some embodiments as shown in FIG. 6A, the gel application system 600 includes the gel packet 502, the applicator 504, the gel slot 506, and the gel 510, which may be the same or similar to those components described above in the gel application system 500. In some embodiments, the gel application system 600 further includes a gel spreading mechanism 602 configured to contact gel 510 that is applied onto a patient or subject, and adjust placement and thickness of the gel 510 (e.g., along a temporal window or other defined area of the patient or subject). In some embodiments, the gel spreading mechanism 602 is located along an outer edge of a surface (the bottom surface) of the applicator 504. In some embodiments, the gel spreading mechanism 602 extends along the entire edge curvature of one end of the applicator 504 (for example, the end of the applicator 504 adjacent or closest to the gel slot 506), but does not extend along the rest of the edge of the applicator 504. In other embodiments, the gel spreading mechanism 602 extends along and around the entire edge of the applicator 504, or along one or more selected portions of the edge of the applicator.

In some embodiments, the gel spreading mechanism 602 is affixed to or formed on one surface of the applicator 504, such as the surface facing opposite to the surface on which the gel packet 502 is located. In other embodiments, the gel spreading mechanism 602 is affixed to or formed on the same side of the applicator 504 on which the gel packet 502 is located. In some embodiments, a gel spreading mechanism 602 is affixed to each or both surfaces of the applicator 504. In some embodiments, the gel spreading mechanism 602 is located at the edge of the end portion of the applicator 504 that is proximate the gel slot 506, as discussed above and shown in the drawings. In other embodiments, the gel spreading mechanism 602 is located at the edge of end portion of the applicator 504 that is opposite the end portion that is proximate the gel slot 506.

In some embodiments, the gel spreading mechanism 602 is made from any suitable soft material, such as, but not limited to, rubber, closed cell foam, open cell foam, self-skinning open or closed cell foams, cast, aerated, or extruded silicone or urethane, polyurethane, or the like. In other embodiments, the gel spreading mechanism 602 is made from any suitable rigid material, such as, but not limited to, plastic, rubber, silicon, metal, ceramic, composite material, wood, cardboard, cardstock and the like. In some embodiments, the gel spreading mechanism 602 is made of a combination of such soft and rigid materials. In some embodiments, the gel spreading mechanism 602 is affixed (e.g., permanently affixed) to the applicator 504 by, for example, but not limited to, welding, adhesive, one or more hooks and latches, friction or press fittings, or the like. In some embodiments, the gel spreading mechanism 602 may be formed directly on the applicator 504 by any suitable manufacturing techniques, including, but not limited to molding, machining, or the like. In some embodiments, after discharging the gel 510 onto a subject, a user may employ the gel spreading mechanism 602 to adjust the thickness and position of the gel 510 on the patient or subject as desired. The gel spreading mechanism 602 can provide the user with a relatively fine control of the thickness and placement of the gel 510. In some embodiments, the gel spreading mechanism 602 can have any suitable shape or configuration for spreading or controlling gel. For example, the gel spreading mechanism may have one or more generally flat, tapered or curved surfaces that extend outward from a surface of the applicator 504 (extend outward from the surface facing opposite to the surface on which the gel packet 502 is located) and form one or more tapered or pointed distal edges). In some examples, the generally flat, tapered or curved surfaces of the gel spreading mechanism has a curvature that curves around (or partially around) the first end of the applicator 504.

FIG. 6B illustrates a perspective view of a gel application system 650 according to various embodiments.

In some embodiments, the gel application system 650 is similar to the gel application system 600 described above, and includes the gel packet 502, the applicator 504 and the slot 506, which may be the same or similar to those components described above for the gel applicator system 602. In some embodiments, the gel application system 650 includes a gel spreading mechanism 652, which may be similar to the gel spreading mechanism 602 discussed above, or may have a different configuration such as described below and shown in FIG. 6B. In some embodiments, the gel application system 650 also includes a scraper 654, and a string or lanyard 656.

In some embodiments, the gel spreading mechanism 652 protrudes outward relative to the surface of the applicator 504 opposite to the surface on which the gel packet 502 is located, and extends along one side edge and a portion of the first end (top end) edge of that surface of the applicator 504. In some embodiments, the scraper 654 is located adjacent the gel spreading mechanism 652 and protrudes outward relative to the surface of the applicator on which the gel packet 502 is located, and extends along one side edge and a portion of the first end (top end) edge of that surface of the applicator 504. In other embodiments, the gel spreading mechanism 652 and the scraper 654 are located at opposite ends of the applicator 504. In some embodiments, the scraper 654 is configured to move and lift gel 510 from a patient or subject (e.g., for cleaning the patient or subject). In some embodiments, the scraper 654 is made from any suitable rigid material, including, but not limited to, plastic, silicon, rubber, metal, ceramic, composite material, wood, cardboard, cardstock and the like. In some embodiments, the scraper 654 includes a raised lip along its outer edge configured such that the scraper 654 can lift gel 510 off of a subject.

In some embodiments, the string or lanyard 656 is formed in a loop shape to allow a user to easily grip the gel application system 650. In other embodiments, the string or lanyard 656 includes a strip or piece of material that a user can grip while utilizing the gel application system 650, or for grabbing in the event the gel application system 650 is dropped (e.g., within a TCD system) such that the user can easily retrieve the gel application system 650. In some embodiments, the string or lanyard 656 is attached (e.g., permanently attached) to the applicator 504 by, for example, but not limited to, welding, adhesive, one or more hooks and latches, press fittings, or the like. In other embodiments, the string or lanyard 656 is attached to the applicator 504 in a releasable manner, to allow the string or lanyard 656 to be removed from the applicator 504, if desired. The string or lanyard 656 is made from any suitable material, such as, but not limited to, nylon, plastic, fabric, cotton, metal, or the like.

For example, FIG. 6C-6I illustrate various gel application systems 660, 665, 670, 675, 680, 685 and 690 having various different slot or opening configurations or gel packet configurations, according to various embodiments. In some embodiments, the gel application systems 660, 665, 670, 675, 680, 685 and 690 are the same or similar to the gel application systems 500, 600, and 650, as described above, but with the differences described and shown herein.

Figure 6D:
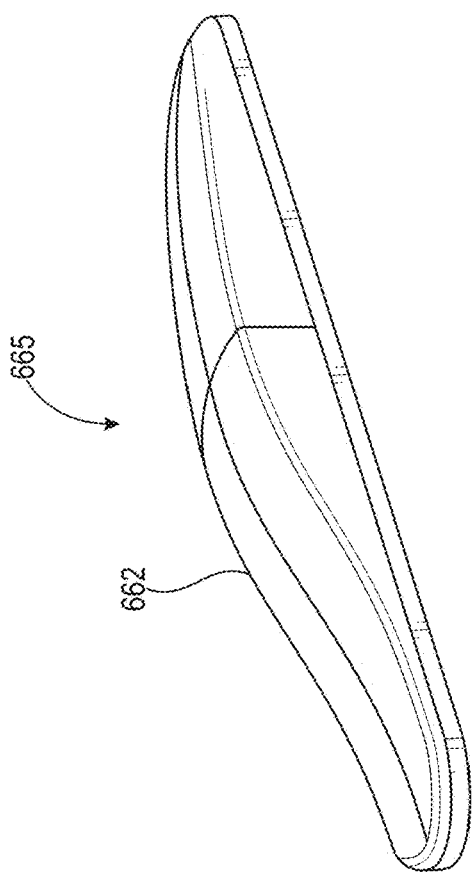
Figure 6C:
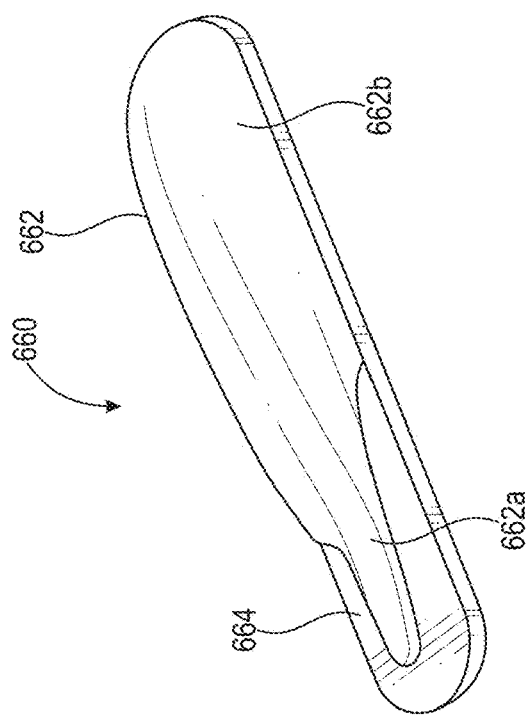

For example, the gel application system 660 in FIG. 6C includes a gel packet 662 that has a narrow or neck section 662a and a wider reservoir section 662b. The narrow or neck section 662a is narrower in width than the wider reservoir section 662b, and extends over a slot-shaped opening on an applicator 664 (such as the slot-shaped opening 506 described above). In other embodiments, the neck section 662a extends over one or more openings having other shapes or arrangements that fit under the neck section 662a. The narrower neck section 662a can provide a limited flow rate and, thus, can provide the user with a greater level of control over the rate of flow of gel to (and through) the slot-shaped opening, from the wider reservoir section 662b of the gel packet 662 (as compared to a gel packet configuration of the gel application system 665 and 670 as shown in FIGS. 6D and 6E). In other embodiments such as shown in FIGS. 6D and 6E, the gel packet 662 may have other shapes or configurations, for example, that cover all (or substantially all) of the first surface of the applicator 664.

In various embodiments described herein, the gel application system includes one or more gel slots or other shaped openings in the applicator. Examples of some, but not all, slot or opening configurations are shown in FIGS. 6F-6I, including a configuration having a single slot (such as the gel application system 675 in FIG. 6F), a configuration having a plurality of slots arranged generally parallel to each other (such as the gel application system 680 in FIG. 6G) and a configuration having an arrangement of a plurality of round openings (such as the gel application system 685 in FIG. 6H or the gel application system 690 in in FIG. 6I). In other embodiments, other suitable opening configurations or arrangements may be employed, to provide a desired pattern or rate of flow of gel from the gel application system.

Figure 6I:
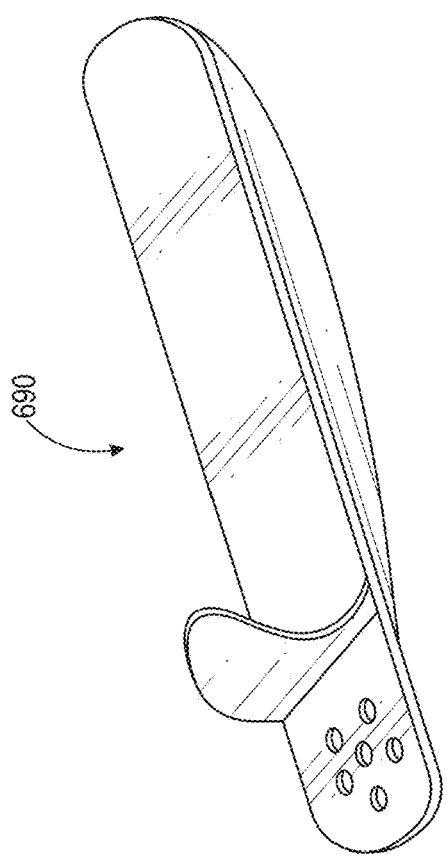
Figure 6H:
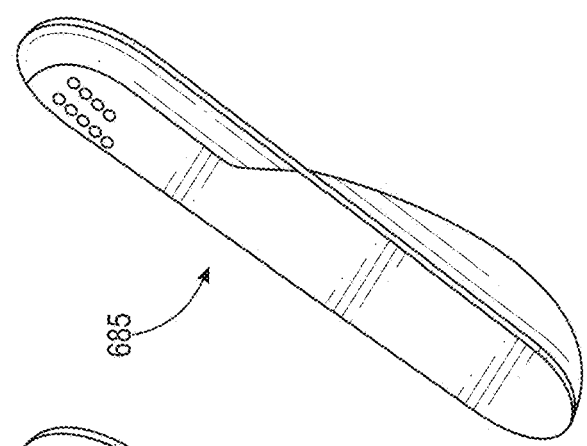
Figure 6G:
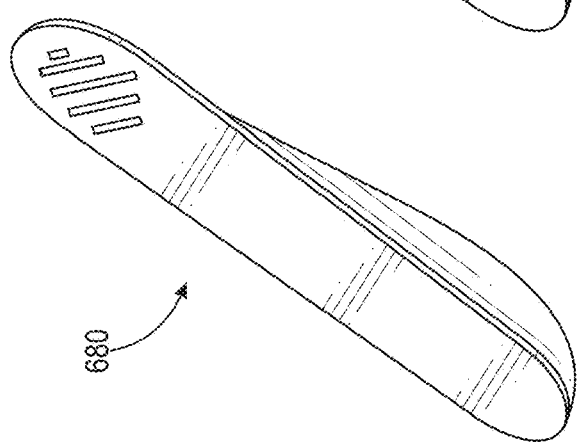

In further examples of any of the embodiments of FIGS. 5A-6I, the gel application system includes a peel away seal (such as described above with regard to seal 508) that is removably adhered to the second surface of the applicator and covers the one or more openings in the applicator, to inhibit the flow of gel from the gel application system until or unless the seal is peeled away. In other embodiments, the gel application system includes a pivotal, rotatable or sliding panel or door, cork or stopper for selectively closing and opening the gel slot (such as described above). In some embodiments, a peel away seal may cover the one or more openings and a limited area of the applicator around the one or more openings (but not cover the entire second surface of the applicator). In other embodiments, the peel away seal may cover substantially the entire second surface of the applicator, as shown in FIG. 6I. The peel away seal may include a surface (facing outward) that provides an area for printed information including, but not limited to, directions for use, product or manufacturer name or information, date of manufacture or of expiration, other date information, or the like.

In further examples of any of the embodiments of FIGS. 5A-6I, the applicator is transparent such that a user can view gel in the gel packet or view can the flow of gel along the applicator. Alternatively or in addition, any of the embodiments of FIGS. 5A-6I may include a gel spreading mechanism 602, a scraper 652, a string or lanyard 656, or any combination thereof.

Figure 7B:
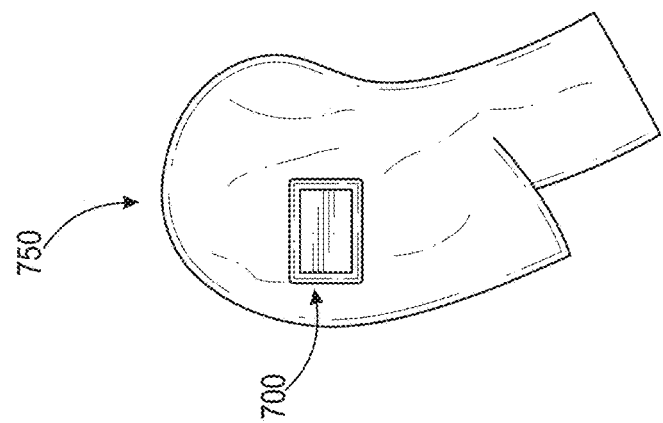
FIG. 7B illustrates a side view of a head of a subject and the gel application system shown in FIG. 7A attached thereto according to various embodiments.
Figure 7A:
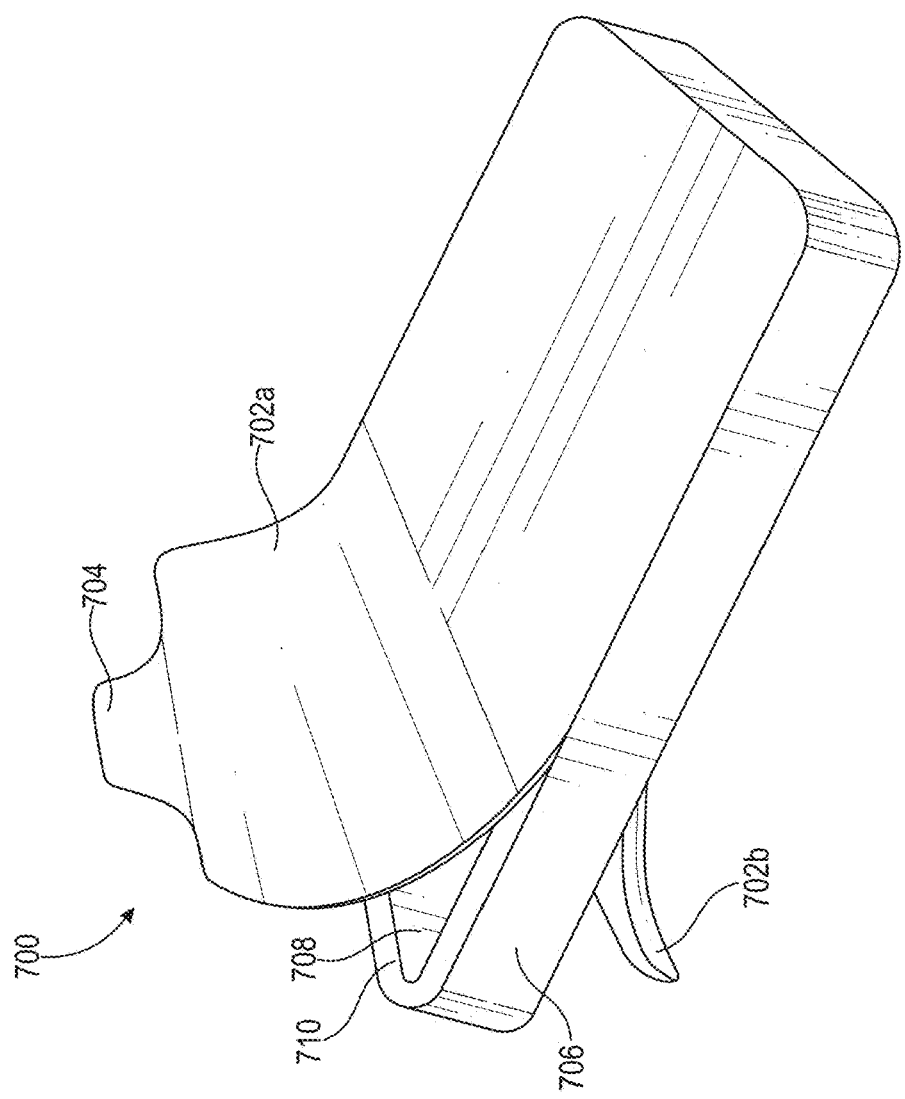
FIG. 7A illustrates a perspective view of a gel application system according to various embodiments.

FIG. 7A illustrates a perspective view of a gel application system 700 according to various embodiments. FIG. 7B illustrates a side view of a head of a subject 750 and the gel application system 700 shown in FIG. 7A attached thereto according to various embodiments.

In some embodiments, the gel application system 700 includes a barrier 706 and a cover 702a or 702b at each side of the barrier 706. In some embodiments, the covers 702a and 702b are configured to seal with the barrier and form an interior volume for containing a gel 708 within the barrier 706 and between the two covers 702a and 702b. In some embodiments, each of the top surface and the bottom surface of the edges of the barrier 706 includes an adhesive layer 710 thereon such that the two respective covers 702a and 702b are releasably affixed to the two respective sides of the barrier 706. More specifically, the cover 702a is releasably affixed to a first side of the barrier 706, while the cover 702b is releasably affixed to a second side of the barrier 706 (opposite to the first side). In other embodiments, each of the covers 702a and 702b includes the adhesive layer 710, or both the barrier 706 and each of the covers 702a and 702b include adhesive layers 710. In some embodiments, each of the covers 702a and 702b includes a tab 704 for allowing a user to easily grip the cover 702a or 702b, for peeling back one or both covers 702a and 702b and exposing the gel 708 enclosed by the barrier 706.

In some embodiments, a user peels a first cover 702a from the first side of the barrier 706 using the tab 704, to expose one side of the volume of gel 708 that is contained by the barrier 706 and the second cover 702b. In some embodiments, at least some adhesive material remains on the first side of the body of the barrier 706, after removal of the first cover. Then, the side of the barrier 706 from which the first cover 702a was removed is affixed to the patient or subject (for example, to a defined location on the patient's or subject's head 750), for example, by employing the adhesive material that remains on the first side of the body of the barrier 706. Then, the second cover 702b is removed from the second side of the barrier 706 such that a second side of the volume of gel 708 contained by the barrier 706 is exposed, while the barrier (and a volume of gel contained within the barrier) is held on the patient or subject (for example, on the head 750 of the patient or subject). The barrier 706, thus, forms a reservoir of gel 708 that defines an area that a medical device (such as, but not limited to, a TCD device) can scan. In some examples, a film or sheet of plastic or other suitable material may be provided across one side of the barrier 706 (i.e., the side facing outward from the subject or patient's head, when the barrier 706 is secured to the patient or subject), to help retain gel within the barrier 706. Alternatively or in addition, the gel can be held within an envelope or membrane secured to the barrier 706, to help retain gel within the barrier 706. In such embodiments, the film, sheet, envelope or membrane may be configured of material that is sufficiently flexible or pliable to allow the gel to be depressed within the barrier 706, when the film, sheet, envelope or membrane are contacted or pressed by an image device probe.

In some embodiments, the barrier 706 is an annular body made from a rigid or partially flexible (non-rigid) material suitable for containing a volume of gel 708 and holding the volume of gel on the patient or subject (such as, but not limited to on a patient's or subject's head 750), such as, but not limited to, plastic, rubber, metal, ceramic, wood, paper, cardboard, cardstock, composite material and the like. In some embodiments, the barrier 706 has a generally rectangular, annular shape. In other embodiments, the barrier 706 may have a round or rounded annular shape, a square annular shape or other suitable annular shapes. Each cover 702a and 702b may be made of any suitable material such as, but not limited to plastic, metal sheet or foil, paper, composite material, or the like.

Figure 8:
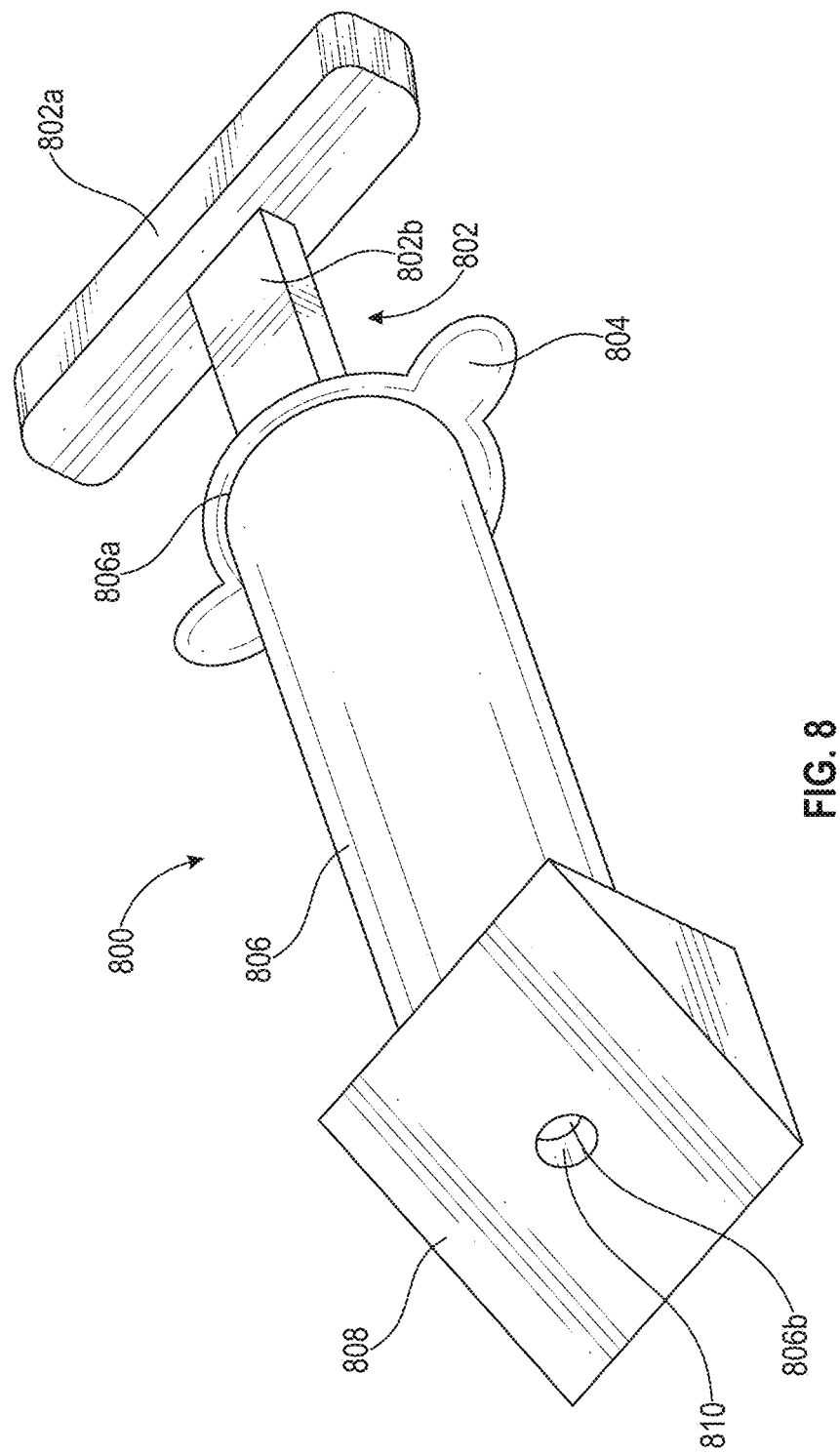
FIG. 8 illustrates a perspective view of a gel application system according to various embodiments.

FIG. 8 illustrates a perspective view of a gel application system 800 according to various embodiments. In some embodiments, the gel application system 800 includes a syringe-type system.

The gel application system 800 includes a plunger 802, a container or barrel 806, and an applicator 808. In some embodiments, the barrel 806 is pre-filled with gel, or with a pre-defined quantity of gel. The barrel 806 in FIG. 8 comprises a generally cylindrical shaped container having an enclosed interior volume for containing gel, an opening on a first end 806a for receiving the plunger 802, and an opening on a second end 806b through which gel from the interior volume of the container may be dispensed. In other embodiments, the barrel 806 has other suitable shapes for containing and retaining a quantity of gel. The barrel 806 may be made of any suitable material having sufficient rigidity to operate as described herein, including, but not limited to plastic, metal, ceramic, composite material or the like. In some embodiments, the barrel 806 is made of a transparent or partially transparent material that allows a user to view contents within the interior volume of the barrel 806, for example, to view the amount of gel contained within the barrel 806. In some embodiments, the barrel 806 includes one or more markings along a length dimension, to define one or more volume levels (or amounts) of gel or other material contained in the interior volume of the barrel 806. In some embodiments, a flange 804 is provided on or adjacent the first end 806a of the barrel 806. The flange 804 can provide a surface against which a user's fingers my press to provide leverage, while pushing the plunger 802 with a thumb.

In some embodiments, the applicator 808 is the same or similar to any of the applicators described herein, including, but not limited to a soft, flexible, or resilient material, such as, but not limited to, closed cell foam, open cell foam, self-skinning open or closed cell foams, cast, aerated, or extruded silicone or urethane, polyurethane, or the like. For example, in some embodiments, the applicator 808 is made of the same or similar material as described herein with regard to the applicator 108, such as, but not limited to a foam material. The applicator 808 is affixed to the second end 806b of the barrel 806 by any suitable attachment mechanism including, but not limited to those described herein for attaching the applicator 108 to the container 102. The applicator 808 may have any suitable shape or configuration, including, but not limited to those described herein with regard to the applicators 108 and 202. However, in some embodiments, the applicator 808 has a wedge shape to enable effective adjustment of gel on a subject. The applicator 808 has a first end and a second end of different widths. In some embodiments, the second end of the applicator 808 is thicker than the first end of the applicator 808, and is affixed to the second end 806b of the barrel 806 as described above. The first end of the applicator 808 (e.g., a thinner end of the wedge-shaped applicator 808 in FIG. 8) defines a free or distal end for contacting gel on a patient or subject during use. In other embodiments, the applicator 808 has any other suitable shape, such as, but not limited to, a triangle, a curve, a rectangle, or the like.

The plunger 802 is moveably received within the barrel 806 and extends partially out from the first end 806a of the barrel 806. In some embodiments, the plunger 802 includes a head portion (not in view) located within the interior volume of the barrel 806, a handle portion 802a located outside of the barrel 806, and a length portion 806b extending from the handle portion 802a to the head portion. In some embodiments, the plunger 802 is formed as a single, unitary structure of a single, uniform material. In other embodiments, the plunger 802 is made of multiple materials and/or components formed or coupled together. The plunger 802 may be made of any suitable material having sufficient rigidity to operate as described herein, including, but not limited to a plastic, metal, ceramic, composite material or the like.

A user imparts a pushing force on the handle portion 802a of the plunger 802, towards the first end 806a of the barrel 806. The pushing force on the plunger 802 causes the plunger 802 to move within the barrel 806, toward the second end 806b of the barrel 806, and imparts a force and increases pressure on the gel contained within the barrel 806. Once sufficient force or pressure is imparted on the gel, some or all of the gel is pushed through the opening in the first end 806a of the barrel 806, to the applicator 808 or to the environment outside of the gel application system 800. In some embodiments, the applicator 808 defines a hole 810 that is in fluid (or gel) flow communication with opening in the second end 806b of the barrel 806, such that gel is expelled onto the applicator 808 or through the applicator 808 and onto a subject via the hole 810, in response to the pushing force of the plunger 802. In some embodiments, the flange 804 may provide the user with additional support and leverage for application of the pushing force on the plunger 802, as described herein.

Figure 9A:
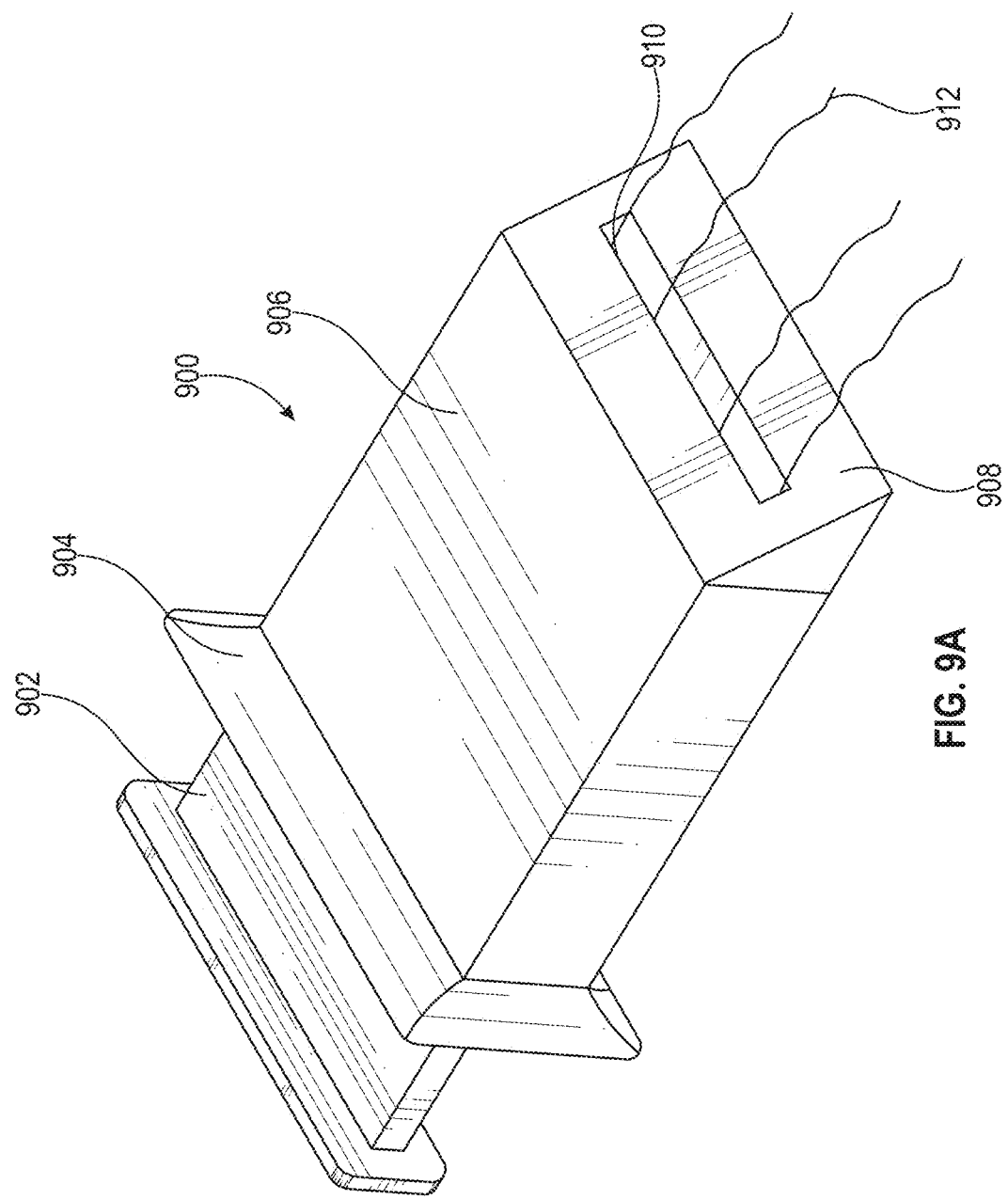
FIG. 9A illustrates a perspective view of a gel application system according to various embodiments.

FIG. 9A illustrates a perspective view of a gel application system 900 according to various embodiments.

In some embodiments, the gel application system 900 includes a plunger 902, a flange 904, a barrel 906, and an applicator 908, which may be similar to the plunger 802, the flange 804, the barrel 806 and the applicator 808 of the gel application system 800 described herein. However, the gel application system 900 a wider body and opening (or outlet port) for wider application of gel, as compared to the gel application system 800.

For example, in the embodiment of FIG. 9A, the barrel 906 has a wider and flatter configuration, with a generally rectangular cylinder shape (cylindrical shape with a generally rectangular cross-section), as compared to the rounded cylinder shape (cylinder shape with a generally round cross-section) of FIG. 8. The wider configuration can accommodate a wider, more elongated outlet opening or slot in the second end of the barrel 906, for a wider distribution of gel from the gel application system 900, as compared to gel application systems having a smaller outlet opening.

In some embodiments, the applicator 908 defines a gel opening or slot 910 that has a generally wide, flat configuration (having a greater width than height), that aligns with the opening in the second end of the barrel 906. A user may cause gel 912 to expel from barrel 906, through the slot 910 in the applicator 908, to the environment external to the gel application system 900 (for example, onto the patient or subject), in response to the plunger 902 imparting a force on the gel within the barrel 906 in a manner similar to the operation of the gel application system 800 described herein. However, because the gel application system 900 has a relatively wide structure, the gel 912 can be applied in layers relatively evenly, and can be easily and quickly applied over a relatively wide area of a patient or subject.

Figure 9B:
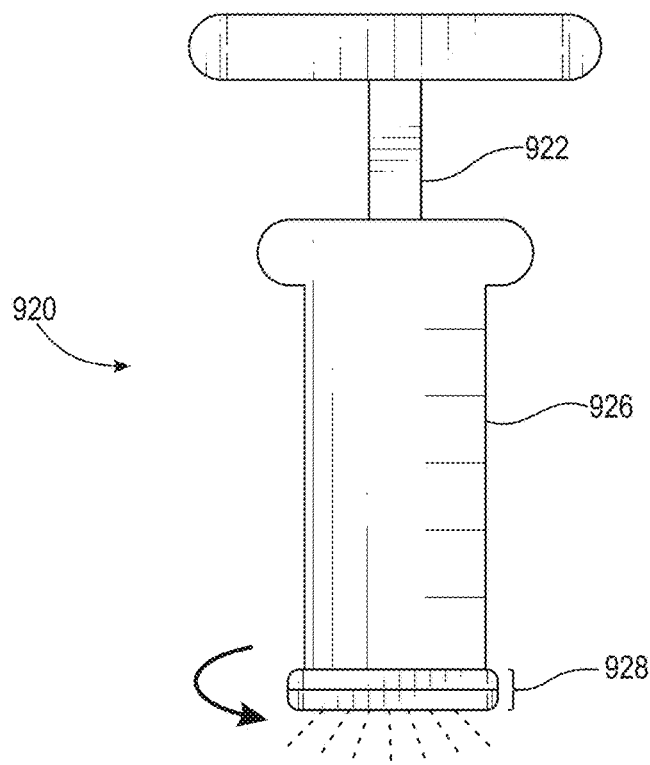
FIG. 9B illustrates a side view of a gel application system according to various embodiments.
Figure 9C:
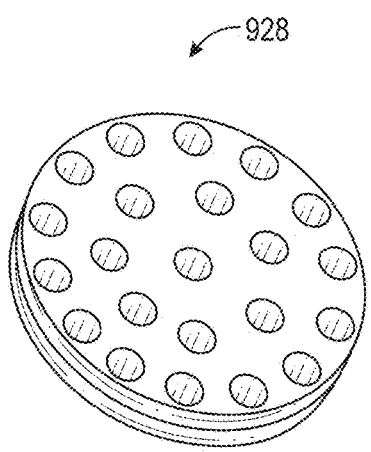
FIG. 9C illustrates an applicator of a gel application system shown in FIG. 9B in an open state for a gel application system according to various embodiments.
Figure 9D:
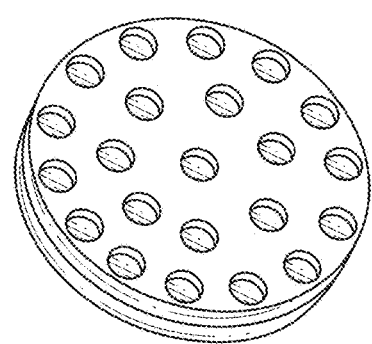
FIG. 9D illustrates an applicator in a closed state for a gel application system according to various embodiments.

In some embodiments, a gel application system having a barrel and plunger (or syringe-type) configuration, such as but not limited to the configurations of FIGS. 8 and 9A, may include other types of applicators. For example, FIGS. 9B-9D show a further embodiment of a gel application system 920 that include a plunger 922 moveable within a container or barrel 926, and to which an applicator 928 is affixed. For example, FIGS. 9E-9F show yet a further embodiment of a gel application system 940 that include a plunger 942 moveable within a container or barrel 946, and to which an applicator 948 is affixed. The applicator 928 or 948 may be affixed to a second end of the barrel 926 or 946 by any suitable attachment mechanism including, but not limited to those described herein for attaching the applicator 108 to the container 102. In some embodiments, the plunger and container or barrel of the gel application systems 920 and 940 may be configured and operated similar to the plunger 802 or 902 and the barrel 806 or 906 described with regard to the gel application system 800 or 900. In some embodiments, the barrel 926 or 946 is pre-filled with gel, or with a pre-defined quantity of gel.

Similar to the above-described operation of the gel application system 800 and 900, a user imparts a pushing force on a handle portion of the plunger 922 or 942, towards a first end of the barrel 926 or 946. The pushing force on the plunger 922 or 942 causes the plunger to move within the barrel 926 or 946, toward the second end of the barrel, and imparts a force and increases pressure on the gel contained within the barrel. Once sufficient force or pressure is imparted on the gel, some or all of the gel is pushed through an open end or opening in the first end of the barrel 926 or 946, to the applicator 928 or 948.

In some embodiments, the gel application system 920 includes an applicator 928 that is configured to provide a gel stamping or flattening mechanism. In some embodiments, the applicator 928 has a valve that has an open state and a closed state. When in the open state, the valve of the applicator 928 allows a portion of the volume of the gel within the barrel 924 to be expelled, for example, onto a surface of a patient or a subject (such as, but not limited to a surface of a patient's or subject's head). When in a closed state, the valve of the applicator 928 provides a surface for manually pressing against a volume portion of gel that has been expelled onto the surface. In some embodiments, the surface is configured sufficiently flat to provide a gel flattening or spreading operation to flatten or spread (or both) the volume portion of gel, when the surface is pressed against the volume portion of gel.

In some embodiments, the valve includes an outlet, such as, but not limited to an outlet plate, having a plurality of openings or an arrangement of one or more openings over a defined area (or surface area of the outlet plate). The one or more opening provide fluid (gel) flow outlet openings through which gel may be expelled from the barrel 926, when the valve of the applicator 928 is in an open state and the plunger 922 is operated (pushed toward the second end of the barrel 926). An example of an arrangement of a plurality of openings over an area of an outlet plate of a valve is shown in FIG. 9B. Other embodiments include other arrangements and shapes of openings. For example, other embodiments may include one or more slot-shaped openings, one or more openings that have a shape of a logo, a letter, a number or a word. In some embodiments, the arrangement or shape (or both) of openings provides a pattern of openings over a defined area (such as, but not limited to the area of an outlet plate), such that gel may be expelled from the outlet over an area of a surface (such as, a surface of a patient or subject) corresponding to the defined area. In some embodiments, the defined area over which gel may be expelled is configured to be sufficiently large to cover a relatively large surface area on a surface of the patient or subject, quickly and efficiently, but in a controlled manner, by operating the plunger as described herein.

In some embodiments, the valve of the applicator 928 includes a closed state in which the one or more openings of the outlet (or outlet plate) are covered or closed, to inhibit the passage of gel through the one or more openings. In some embodiments, the valve of the applicator 928 may be operated to transition from the open state to the closed state by rotating a portion of the valve. For example, in some embodiments, the valve of the applicator includes a second plate arranged against and parallel to the outlet plate, where one or both of the plates are rotatable relative to each other between at least a first relative rotary position and a second relative rotary position of the plates. The second plate has an arrangement of openings or other pattern of one or more openings that correspond to or otherwise align with the one or more openings in the outlet plate to allow the passage of gel through the plates when the second plate and the outlet plate are in the first rotational position relative to each other, but that are offset from the one or more openings in the outlet plate and inhibit the passage of gel through the plates when the second plate and the outlet plate are in the second rotary position relative to each other. In some embodiments, the outlet plate and the second plate may be held within an annular body that is affixed to the second end of the barrel 926, as described above, and that supports one or both of the plates for rotational motion relative to each other. In some embodiments, one or both of the plates are arranged on respective rotational sections of the annular body, for rotation relative to each other, upon a user gripping and rotating the respective rotational section of the annular body. In other embodiments, one or both of the plates supported for rotational motion include an outward extending tab (not shown) that can be engaged by a user to manually rotate the one plate relative to the other, or both plates relative to each other.

In some embodiments, when the outlet plate and the second plate are rotated to a first state (an open state of the valve), the one or more openings in the respective plates are sufficiently aligned to allow gel to be expelled from the barrel 926, when the plunger 922 is moved toward the second end of the barrel 928, to dispense a volume of gel over a relatively large area of a surface of a patient or subject. In some embodiments, when in the plates are then rotated to the second rotary position, the outward facing surface of the arrangement of plates is sufficiently flat and defines a relatively wide surface area. In that state the applicator 928 may be used as a gel stamping or flattening tool. In that state, a user may grip the barrel 926 and press the second end of the barrel downward onto the volume of gel that has been dispensed over the surface area of the patient or subject, for example, to spread or flatten the gel over that surface area, or to enlarge the gel covered surface area.

In some embodiments, the applicator 928 (including the valve) is removeably affixed to the second end of the barrel 926, and is selectively removable from the barrel 926. In such embodiments, the applicator 928 (and valve) may be removed and disposed of, after a desired time of use. In other embodiments, the entire gel application system 920 is configured to be disposed of, after a desired time of use.

In further embodiments, the applicator 948 of the gel application system 940 (in FIGS. 9E and 9F), is configured for gel dispensing and gel spreading. In some embodiments, the applicator 948 includes a generally flat or plate-like body of rigid or partially rigid material that has a first end 948*a* connected to the second end of the barrel 946. The applicator 948 has a second end (a distal end) 948*b* that defines a spreading edge or surface (or both). The first end 948*a* of the applicator 948 is thinner in a width dimension than the second end 948*b* of the applicator 948. In some embodiments, the applicator body has a tapered shape that tapers from the thinner first end 948*a*, toward the wider second end 948*b*. In some embodiments, the applicator 948 may have a spatula-like shape or configuration, with a suitable thickness dimension to include one or more interior channels as described below.

The applicator 948 may be made of any suitable rigid or partially rigid material such as, but not limited to plastic, rubber, silicon, metal, wood, ceramic, composite material, or the like. In some embodiments, the material of the applicator 948 is sufficiently rigid to hold its shape, but has some flexibility to allow the applicator 948 to bend slightly across its length dimension, when a user grips the barrel 948 and manually presses the second end (distal end) 948*b* against a surface. In other embodiments, the material of the applicator 948 is sufficiently rigid so as to inhibit bending during use.

In some embodiments, the wider, second end of the applicator 948 has an edge feature 950 configured to enhance the ability to spread gel. In some embodiments, the edge feature 950 is formed on and is unitary with the body of the applicator (at the second end 948*b* of the applicator 948). In other embodiments, the edge feature 950 is a separate element that is attached to the second end of the body of the applicator 948 by any suitable attachment mechanism including, but not limited to an adhesive, welding, thermal bonding, snap fitting, friction or press fitting, or the like. In some embodiments, the edge feature 950 is a separate element that is molded or co-molded onto the body of the applicator 948.

In some embodiments, the edge feature 950 includes one or more of an angled or a beveled edge, a stepped or a reduced width edge, or a blade or an edging strip made of silicon, plastic, rubber, metal, ceramic or the like. In some embodiments, the edge feature 950 includes a blade or an edging strip that is made of a material that is more flexible (and less rigid) than the material of the rest of the applicator 948.

In some embodiments, the applicator 948 has one or more interior channels (or a hollow interior) having a first end in fluid (gel) flow communication with the opening in the second end of the barrel 946. The one or more interior channels of the applicator 948 extend along at least a portion of the length dimension of the applicator 948, from the first end of the applicator 948, to one or more (or a plurality of) outlet openings 952. In some embodiments, such as shown in FIG. 9F, the one or more (or plurality of) outlet openings 952 are located on one side (a first surface) of the generally flat or plate-like body of the applicator 948. In some embodiments, the opposite side (a second surface facing opposite to the first surface) of the generally flat or plate-like body of the applicator 948 defines a generally flat surface that is devoid of outlet openings, and is suitable for contacting and spreading gel, such as shown in FIG. 9E.

In some embodiments, the one or more outlet openings 952 includes a plurality of outlet openings of different sizes or shapes (or both). In some embodiments, the one or more outlet openings 952 include one or more (or a plurality of) slot shaped openings. In some embodiments, the one or more outlet openings 952 include one or more (or a plurality of) round openings, or a combination of one or more slot-shaped openings and one or more round openings. In some embodiment, the one or more openings includes a plurality of openings arranged along a width dimension of the body of the applicator 948, so as to dispense gel over a relatively wide band or area. In some embodiments, the one or more outlet openings 952 are arranged adjacent to and along the wider second end 948b of the body of the applicator 948 (closer to the second end 948b than to the first end 948a). In some embodiments, the one or more outlet openings 952 are arranged adjacent to the second end 948b, but spaced a short distance (such as, but not limited to 0.1 to 100 mm) from the second end 948b of the body of the applicator 948.

In some embodiments, the barrel 946 includes a second flange or lip 954 at or near the second end of the barrel 946. The second flange or lip 954 provides a surface against which a user may press one or more (or a pair) of fingers of one hand, while pushing the plunger 942 toward the second end of the barrel 946 with a thumb or the palm of the same hand. The second flange or lip 954 can provide leverage to assist the user in pushing the plunger 942 toward the second end of the barrel 946 (or drawing/pulling the second end of the barrel 946 toward the handle end of the plunger). In some embodiments, a second flange or lip (such as the second flange or lip 954) may be included in any of the other embodiments employing a plunger and barrel configuration in FIGS. 8 and 9A-9F.

In some embodiments, the gel dispensing system 940 is gripped by a user and the applicator 948 is oriented and directed toward or adjacent a surface of a patient or subject, with the surface or side of the applicator body having the one or more openings 952 facing the surface. In that orientation, the plunger 942 is moved toward the second end of the barrel 948, to dispense a volume of gel from the one or more outlet openings 952, over a relatively wide or large area of a surface of a patient or subject. In some embodiments, the gel dispensing system 940 may be rotated so that the second side of the body of the applicator 948 is directed toward and faces the surface of the patient or subject. In that orientation, the flat surface of the body of the applicator 948 or the edge feature of the applicator may be applied to contact the volume of gel that has been dispensed on the surface of the patient or subject, to spread gel or enlarge the surface area covered by the gel. Alternatively or in addition, the gel dispensing system 940 may be held in an orientation in which the side (the first surface) having the one or more openings 952 is oriented upward while the plunger 942 is moved toward the second end of the barrel 948, such that a desired volume portion of the gel is dispensed from the one or more outlet openings 952 onto that side (first surface) and adjacent the second end 948b of the applicator 948. Then, the user may orient the gel application system 940 such that the side (first surface) of the applicator 948 is directed and moved toward a surface of the patient or subject to apply or spread (or both) the volume portion of gel onto the surface.

Figure 10:
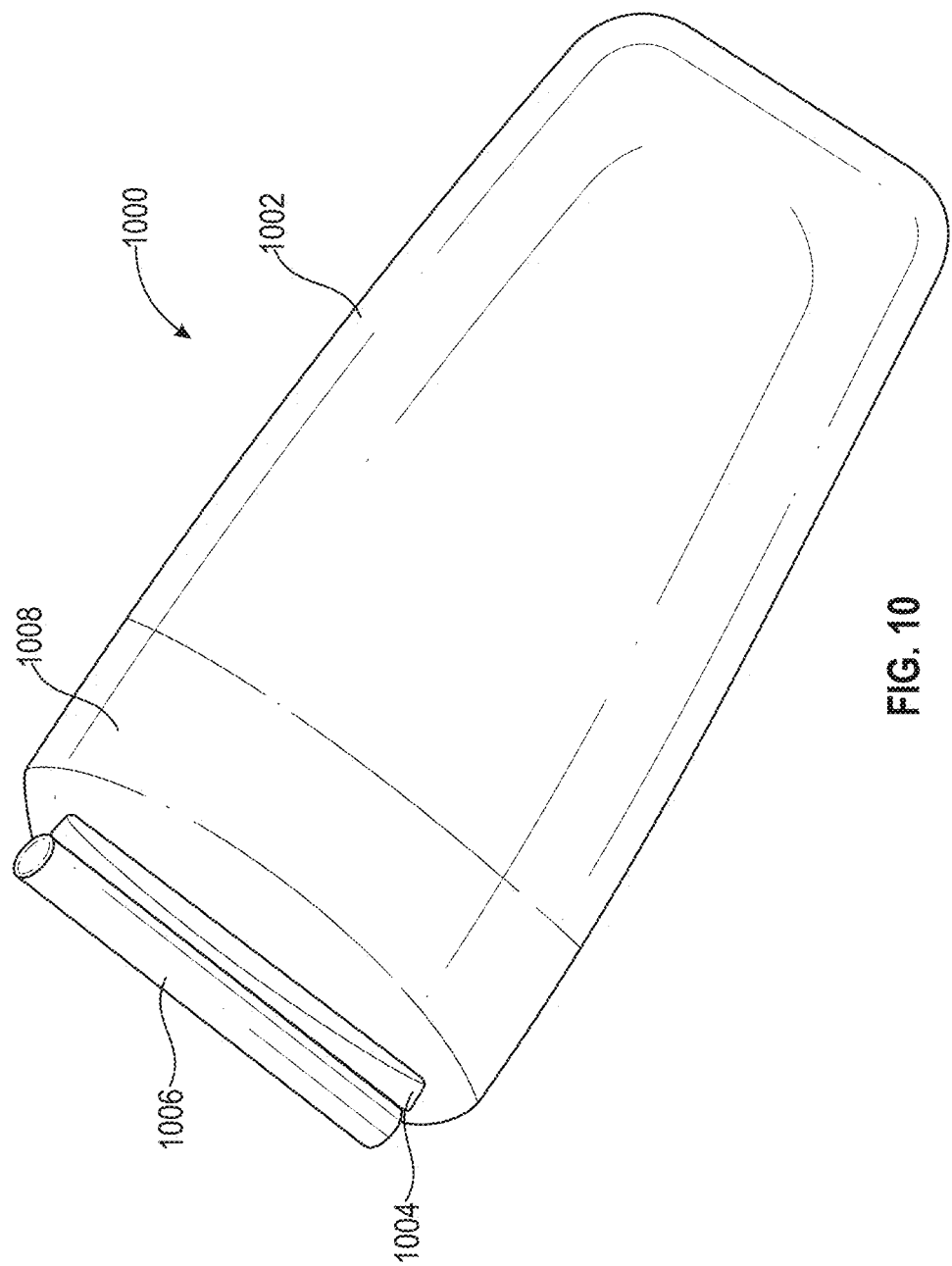
FIG. 10 illustrates a perspective view of a gel application system according to various embodiments.

FIG. 10 illustrates a perspective view of a gel application system 1000 according to various embodiments.

In some embodiments, the gel application system 1000 includes a bag 1002, a gel slot 1004, and a spreader or scraper 1006. The bag 1002 has an interior volume configured to contain an amount of gel therein. The bag 1002 is made of a material that is flexible and malleable to allow a user to squeeze and compress the bag 1002 to expel gel through the gel slot 1004. The bag 1002 is made from any suitable pliable material, such as, but not limited to, plastic, rubber, metal foil, and the like. In some embodiments, the gel in the bag 1002 is discharged from the gel application system 1000 via the gel slot 1004 (e.g., by a user squeezing the bag 1002) and directing the gel slot 104 toward a patient or subject.

In some embodiments, the spreader or scraper 1006 includes or is made from any suitable soft material, such as, but not limited to, rubber, closed cell foam, open cell foam, self-skinning open or closed cell foams, cast, aerated, or extruded silicone or urethane, polyurethane, or the like. In other embodiments, the spreader or scraper 1006 includes or is made from any suitable rigid material, such as, but not limited to, plastic, silicon, rubber, metal, ceramic, composite material, wood, cardboard, cardstock and the like. In some embodiments, the spreader or scraper 1006 includes a combination of such soft and rigid materials. In some embodiments, the spreader or scraper 1006 is the same or similar to the scraper 654, as described above. In some embodiments, the spreader or scraper 1006 is used to spread, adjust or remove gel that is discharged from the gel application system 1000 (e.g., on a patient or subject). In some embodiments, the spreader or scraper 1006 is similar to the scraper 654, as described above.

In some embodiments, the gel application system 1000 includes a head portion 1008, to which an open end of the bag 1002 is adhered, where the head portion 1008 include the gel slot 1004 in fluid (or gel) flow communication with the interior volume of the bag 1002. In such embodiments, the spreader or scraper 1006 may be secured to an end of the head portion 1008 opposite to the end of the head portion 1008 to which the bag 1002 is adhered. In such embodiments, the head portion 1008 may be made of any suitable material having sufficient rigidity to operate as described herein, including, but not limited to, plastic, rubber, metal, ceramic, composite material, and the like. In other embodiments, the head portion 1008 may be omitted, such that the gel slot 1004 is provided in an end portion of the bag 1002, and the spreader or scraper 1006 is adhered directly to the bag 1002.

FIG. 11A illustrates a side view of a gel application system 1100 before activation (in an inactivated state) according to various embodiments. FIG. 11B and FIG. 11C illustrate perspective views of the gel application system 1100 shown in FIG. 11A that is being activated (in an activated state) according to various embodiments.

In some embodiments, the gel application system 1100 includes one or more gel containers 1102 defining one or more (or a plurality of) gel packets or pouches, an applicator 1104, and a base 1106. In the embodiment of FIG. 11A, the one or more gel packets or pouches includes two gel packets or pouches 1102a and 1102b. In other embodiments, the gel container(s) 1102 may define a single gel packet or pouch (e.g. 1102a or 1102b), or more than two gel packet or pouches. In some embodiments, the one or more gel containers 1102 may be composed of one sheet (or a plurality of sheets) of flexible material, such as, but not limited to, plastic, rubber, metal foil, or the like, that is (are) sealed around a peripheral edge to the base 1106 to form a flexible wall around one or more internal volumes for containing gel between the sheet of flexible material and the base 1106. In other embodiments, the one or more gel containers 1102 may have other suitable forms including, but not limited to one or more envelopes or enclosed pouches of flexible material adhered to the base 1106. The flexible material of the one or more gel containers 1102 is more flexible and malleable than the material of the base 1106.

In some embodiments, the base 1106 includes a generally flat, plate-like or sheet-like support structure that has sufficient rigidity to provides a support for the one or more containers 1102 and the applicator 1104. In some embodiments, each of the one or more gel containers 1102 is disposed on a first surface of the base 1106. In some embodiments, each of the one or more gel containers 1102 (defining the one or more gel packets or pouches) is permanently affixed to the base 1106 by any suitable connection mechanism including, but not limited to adhesives, welding, bonding, one or more hooks and latches, press fittings, or the like. In some embodiments, the one or more gel containers 1102 are molded or co-molded with or on the base 1106.

In some embodiments, the one or more gel containers 1102 defines at least two gel packets or pouches 1102a and 1102b that are located at opposite end portions 1106a and 1106b of the base 1106 (on opposite sides of a center portion 1106c of the base), as shown in FIG. 11A. In other embodiments, the plurality of gel pouches includes more than two gel pouches 1102a or 1102b on one side portion 1106a or 1106b of the base 1106 (on one side of the center portion 1106c of the base 1106). In other embodiments, the plurality of gel pouches includes more than two gel pouches on each side portion 1106a and 1106b of the base 1106 (on each side of the center portion 1106c of the base 1106).

The base 1106 is made of any suitable material that provides sufficient rigidity to operate as described herein, including, but not limited to plastic, wood, metal, ceramic, cardboard, cardstock, composite material or the like. The base 1106 provides a surface (the first surface) for supporting the one or more gel pouches 1102a and 1102b on the side portions 1106a and 1106b, respectively, and is configured to bend or fold at the center portion 1106c to pivot the second surface of the base side portions 1106a and 1106b toward each other, with the gel pouches 1102a and 1102b located on outward facing surface (the first surface) of each of the base side portions 1106a and 1106b, as shown in FIGS. 11B and 11C. In the pivoted (or activated) state, a user may apply a sufficient amount of force to squeeze the one or more gel pouches 1102a and 1102b between the user's thumb and one or more fingers (to apply a compression pressure to the one or more gel pouches 1102a and 1102b), as shown in FIGS. 11B and 11C. In other embodiments, the base 1106 is configured to bend or fold at the center portion 1106c to move the first surface of each of those base side portions 1106a and 1106b toward each other a sufficient amount to squeeze the one or more gel pouches 1102a and 1102b between the two side portions 1106a and 1106b of the base 1106 (and apply a compression pressure to the one or more gel pouches 1102a and 1102b), as shown in FIGS. 11B and 11C. In such other embodiments, the applicator 1104 may be secured to the second surface of the base 1106, and the base 1106 may include one or more openings or passages that allow gel to flow through the base 1106 to the applicator 1104.

In some embodiments, the base 1106 is made of a material or configuration (or both) that allows bending or folding at the center portion 1106c, while the base side portions 1106a and 1106b remain relatively rigid. In some embodiments, the base 1106 is formed as a single, continuous, uniform sheet or plate of material that is foldable at the center portion 1106c. In such embodiments, the single sheet or plate of material may include a fold line across the center portion 1106c, defined by one or more of a marking, groove, indentation, series of perforations, or the like, to identify a desired folding orientation or to increase the flexibility of the center portion 1106c (or both). In other embodiments, the base side portions 1106a and 1106b are separate members that are connected together at the center portion 1106c by a hinge, seam or other connection structure that allows the base side portions 1106a and 1106b to be folded together, as described herein.

The base 1106 may have any suitable shape formed, for example, from a generally flat, plate-like or sheet-like material. In the embodiments of FIGS. 11A-C, the base 1106, before activation (in an inactivated state of FIG. 11A) has an hourglass-like shape or other shape that has two end portions 1106a and 1106b at opposite ends of its length dimension, where the two end portions 1106a and 1106b are wider (in a dimension perpendicular to the length dimension) than a narrower center portion 1106c located between the two end portions 1106a and 1106b. In some embodiments, the wider end portions of the base 1106 can support a container 1102 of greater volume, while the narrower center portion can enhance the ability of the base 1106 to bend or fold into an activated state.

The applicator 1104 is supported in the center portion 1106c of the base 1106. In some embodiments, the applicator 1104 is affixed directly to the first surface of the base 1106, for example, between the two gel pouches 1102a and 1102b. In other embodiments, the applicator 1104 is affixed to the one or more containers 1102 on the base 1106. The applicator 1104 may be affixed to the base (or to the container(s) 1102) by any suitable affixing mechanism including, but not limited to welding, bonding, adhesive, one or more hooks and latches, press fittings, or the like. In some embodiments, the applicator 1104 may be made of a material and configuration that is similar to any of the applicators described herein (including, but not limited to applicators 108, 202, 808, or 908). In some embodiments, the applicator 1104 includes a triangular or wedge-shaped body of foam material. In some embodiments, each of the gel pouches 1102a and 1102b has an opening or an end portion in fluid (gel) flow communication with the applicator 1104, through which gel may be expelled from each gel pouch into or onto the applicator 1104, when a sufficient compression pressure is applied to the gel pouches. In some embodiments, the applicator 1104 is sufficiently porous or includes one or more holes or slots through which gel expelled from the gel pouches 1102a and 1102b may pass to the exterior environment of the gel application system 1100.

In its inactivated state (e.g., as shown in FIG. 11A), the gel application system 1100 is arranged with the base 1106 in an unfolded or elongated and flat orientation. In the inactivated state, the gel pouches 1102a and 1102b may be in an uncompressed (or a low pressure) state, in which gel is not expelled from the gel pouches. The gel application system 1100 may be packaged, shipped, stored and transported to an environment of use, while in its inactivated state. In some embodiments, the gel application system 1100, when in the inactivated state, has a relatively flat, elongated configuration suitable for efficient packaging, shipping and storage.

To activate the gel application system and cause gel to be expelled from the gel pouches 1102 onto the applicator 1104 (or directly onto a patient or subject), a user folds the gel application system 1100 and imparts a sufficient squeezing force to cause a desired volume of gel to be expelled. In some embodiments, the gel application system 1100 is configured of a size and a shape to be gripped between a thumb and one or more fingers of a user's hand, and squeezed in the activated state, to expel gel in a one-handed operation. In such embodiments, the user's thumb and fingers may contact and apply the squeezing force onto the gel pouches 1102a and 1102b, as shown in FIG. 11C. In some embodiments, by controlling the squeezing force, the user can easily control the rate of flow of gel from the gel pouches 1102a and 1102b. A typical user may have relatively fine control of the squeezing forces that the user can apply between a thumb and one or more fingers and, thus, can provide a relatively fine control of the gel flow rate.

In some embodiments, the one or more containers 1102 includes one or more seals that retain and seal the gel within the one or more gel pouches (e.g., gel pouches 1102a and 1102b). The one or more seals may include any suitable seal material and configuration including, but not limited to those discussed herein for example, with respect to seal 106. In some embodiments, the one or more seal is configured to break (or otherwise open), to allow gel to be expelled out of the one or more gel pouches and onto the applicator 1104 (or directly onto the patient or subject) as described herein. In some embodiments, the one or more seals are configured to break (or otherwise open) automatically, upon the base 1106 being folded or bent in the center portion 1106c a sufficient amount. In some embodiments, the one or more seals are configured to break (or otherwise open) automatically, upon the user applying a squeezing force that increases the pressure of the gel within the one or more gel pouches 1102a and 1102b above a predefined amount. For example, the gel pressure may act directly on the one or more seals, to cause the one or more seals to rupture, upon the gel pressure exceeding the predefined amount or threshold. Accordingly, in some embodiments, a user can fold the base 1106 and squeeze the one or more gel pouches 1102a and 1102b to provide a sufficient force to break (or otherwise open) the seal and continue to squeeze, to expel a desired volume of gel from the one or more pouches 1102a and 1102b (e.g., onto the applicator 1104 or onto a patient or subject).

Figure 12A:
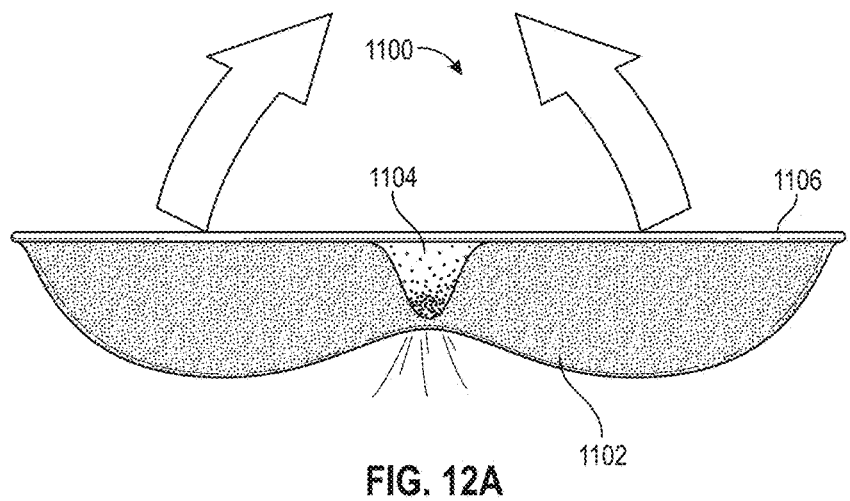
FIG. 12A, FIG. 12B, and FIG. 12C illustrate various views of the gel application system shown in FIGS. 11A-11C according to various embodiments.
Figure 12B:
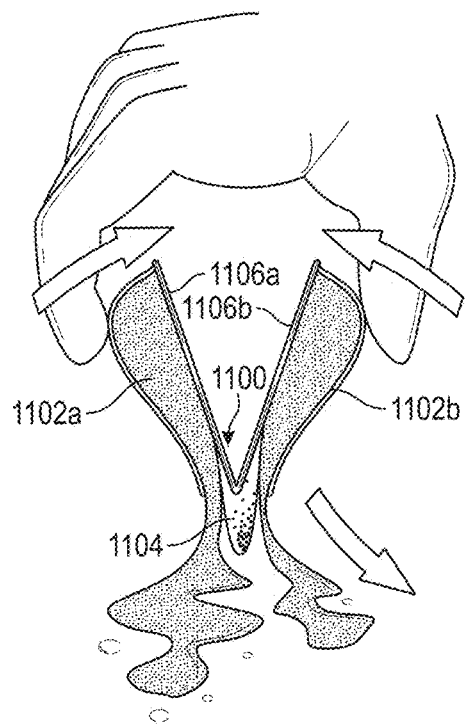
Figure 12C:
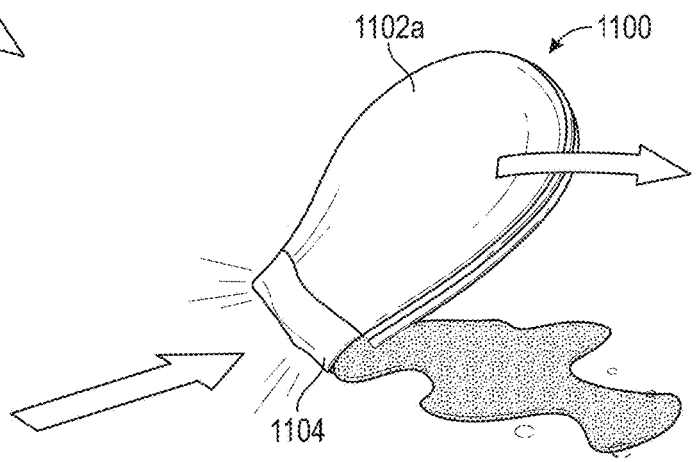

FIGS. 12A-12C illustrate various views of a gel application system 1100 according to further embodiments. In the embodiment of FIGS. 12A-12C, the material forming the wall of the container 1102 includes a central portion that extends along the applicator 1104 (and extends between the gel pouches 1102a and 1102b), where the central portion of the wall of the container 1102 is configured to rupture, tear or break (or otherwise open) when the base 1106 is folded toward the activation state by a sufficient amount. In some embodiments, the material of the container 1102 wall may be configured to have a thinner, weaker or breakable portion in the center portion of the container 1102 (adjacent the applicator 1104) as compared to other portions of the container 1102 wall. In such embodiments, the action of folding the base 1106 causes the wall of the container 1102 to be pulled or stretched over the applicator 1104 a sufficient amount to rupture, tear or break (or otherwise open) the central region of the wall of the container 1102, as shown in FIGS. 12A and 12B. In addition, the rupture, tear or break (or opening) of the central region of the wall of the container 1102 exposes at least a portion of the (or the entire) applicator 1104, as shown in FIGS. 12B and 12C.

Accordingly, in some embodiments, the wall of the container 1102 is configured to automatically open and allow the release of gel from one or more gel pouches formed by the container 1102 wall, and to automatically expose the applicator 1104, when the gel application system is folded or bent from an inactivated state to an activated state. In some embodiments, gel is expelled from the one or more gel pouches, only upon the user applying a squeezing force above a defined threshold needed to sufficiently compress the one or more gel pouches, once the gel application system has been folded into an activated state.

Figure 13A:
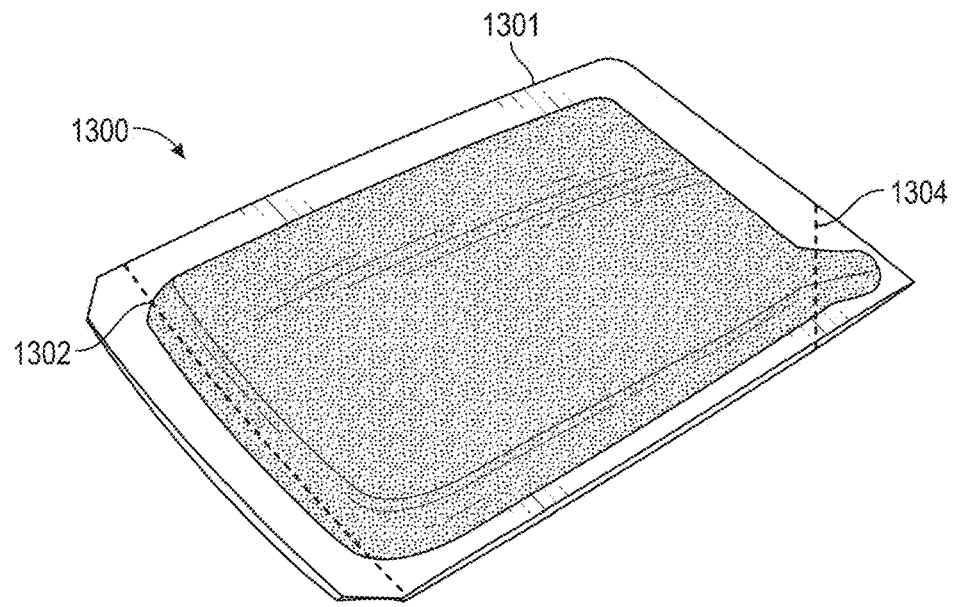
FIG. 13A and FIG. 13B illustrate views of a gel application system according to various embodiments.
Figure 13B:
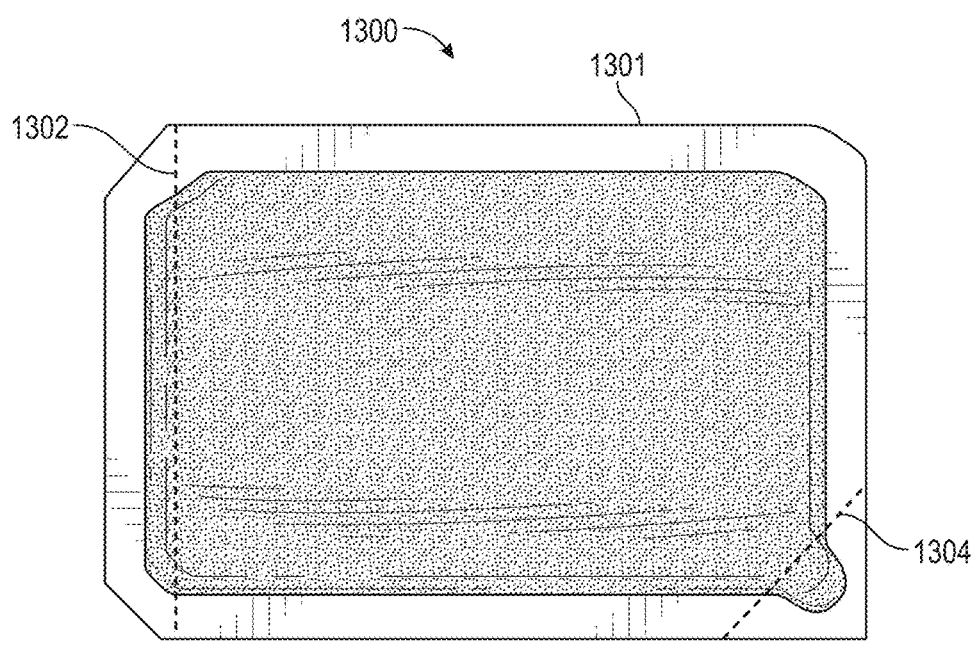

FIG. 13A and FIG. 13B illustrate views of a gel application system 1300 according to various embodiments.

In some embodiments, the gel application system 1300 includes a gel packet 1301 that contains a predetermined amount of gel (e.g., ultrasound gel or other gel as described herein). In some embodiments, the gel packet 1301 is made of one or more sheets of flexible material such as, but not limited to plastic, rubber, metal foil, or the like, that is folded or sealed (or both) at peripheral edges to form a pouch or pocket-like, enclosed interior volume for containing and retaining the gel. In some embodiments, the gel packet 1301 is flexible and malleable to allow a user to squeeze the gel packet 1301 to compress the interior volume of the gel packet and increase the gel pressure within the interior volume. In some embodiments, some or all of the material of the gel packet 1301 is transparent to allow a user to view the gel inside of the gel packet from outside of the gel packet. In some embodiments, the gel application system 1300 has one or more tear sections, each of which is configured to be torn away from the rest of the gel packet 1301, to form an opening into the interior volume of the gel packet, through which gel may be expelled from the gel packet. Each tear section may include one or more lines of perforations, indentations, thin regions or weaker regions on or in the flexible material forming the gel packet 1301, to enhance the user's ability to tear the tear section from the rest of the packet 1301. In some embodiments, the tear section is configured to be torn off of and fully removed from the rest of the gel packet 1301. In other embodiments, the tear section is configured to be torn partially off of the rest of the gel packet 1301, but also remain partially attached to the gel packet 1301.

In some embodiments, the gel application system 1300 has a first tear section 1302 along an entire width dimension of the gel packet 1301. For example, the gel packet 1301 may have a generally rectangular shape, where the first tear section 1302 extends from one lengthwise edge to an opposite lengthwise edge of the generally rectangular shape, adjacent and along a widthwise edge of the generally rectangular shape. Upon tearing away the first tear section from the rest of the gel packet 1301, the interior volume of the gel packet 1301 is opened along the entire width dimension of the gel packet 1301, which allows for a high rate of gel flow from the gel packet 1301.

In some embodiments, the gel application system 1300 has a second tear section 1304 along a corner of the gel packet 1301, in addition to or as an alternative to the first tear section 1302. The second tear section 1304 may have any suitable configuration for enhancing the ability of the user to tear the second tear section 1304 from the rest of the gel packet 1301 including, but not limited to, a configuration as described above for the first tear section 1304. Upon tearing away the second tear section 1304 from the corner of the gel packet 1301, an opening is formed to the interior of the gel packet 1301 that is smaller than the opening formed by removing the first tear section 1402. Accordingly, the opening formed by removing the second tear section 1305 allows for a lower rate of gel flow.

In some embodiments, the first tear section 1302 enables fast discharge of the gel from within the gel packet 1301, and the second tear section 1304 enable slower and more controlled discharge of the gel, as desired. In other embodiments, one or more additional or other tear sections are included at the gel packet (such as, but not limited to one or more of: a tear section along a portion or the entire length dimension of the gel packet 1301, a tear section across one or more other corners, or tear sections across other corners but at mutually different distances from the corners to form different size openings at different corners).

Figure 14A:
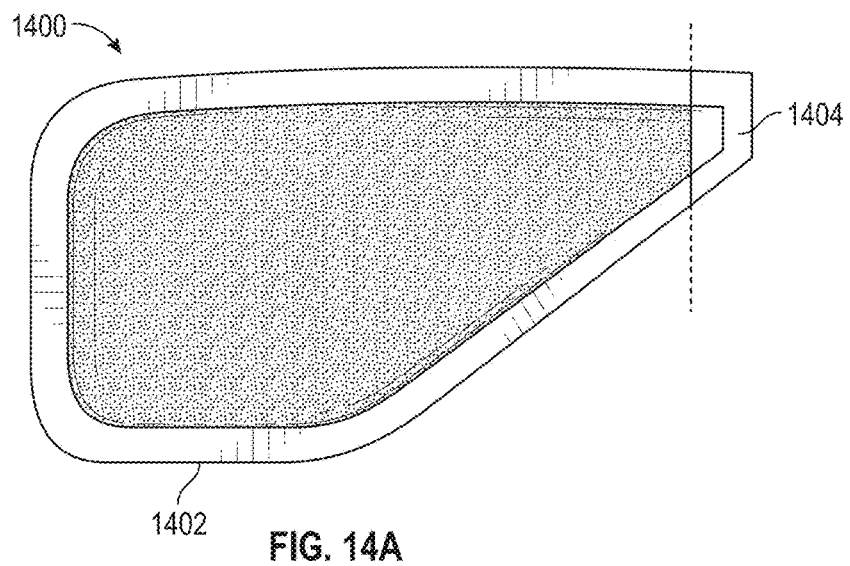
FIG. 14A illustrates a side view of a gel application system according to various embodiments.
Figure 14B:
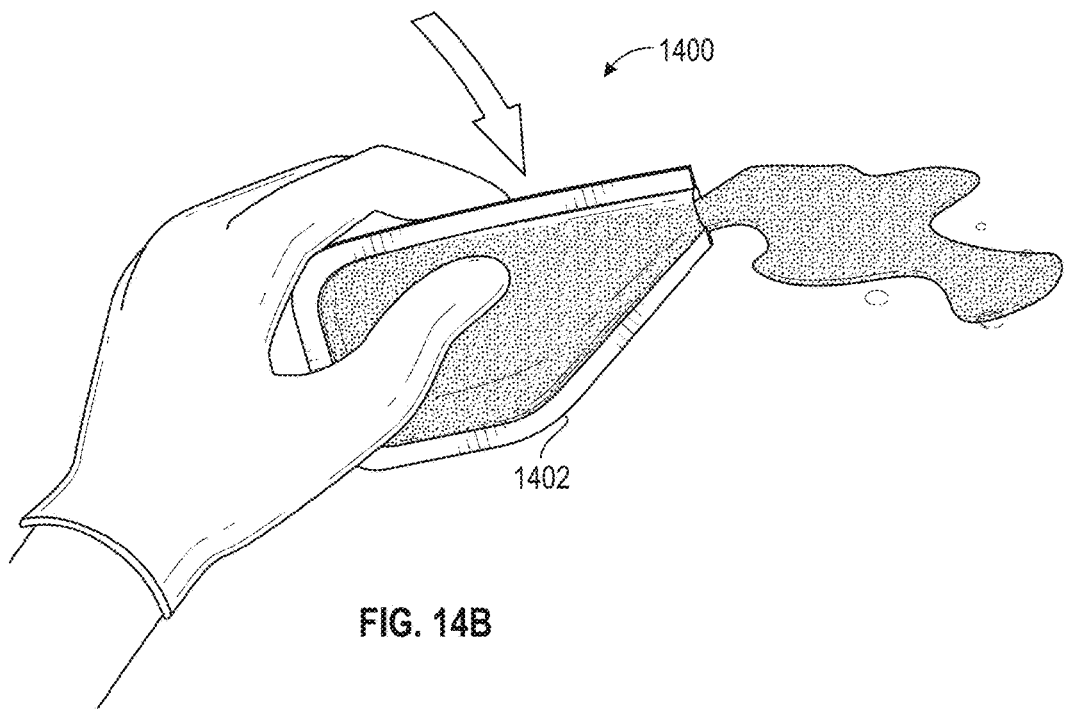
FIG. 14B illustrates a side view of a user utilizing the gel application system shown in FIG. 14A according to various embodiments.

FIG. 14A illustrates a side view of a gel application system 1400 according to various embodiments. FIG. 14B illustrates a side view of a user utilizing the gel application system 1400 shown in FIG. 14A according to various embodiments.

In some embodiments, the gel application system 1400 includes a gel packet 1402 that contains a predetermined amount of gel (e.g., ultrasound gel or other gel as described herein). In some embodiments, the gel packet is made of one or more sheets of flexible material such as, but not limited to plastic, rubber, metal foil, or the like, that is folded or sealed (or both) at peripheral edges to form a pouch or pocket-like, enclosed interior volume for containing and retaining the gel. In some embodiments, some or all of the material of the gel packet is transparent to allow a user to view the gel inside of the gel packet from outside of the gel packet.

The gel packet 1402 that has a shape that allows a user to easily grip or grab the gel packet for squeezing the gel therefrom (e.g., as shown in FIG. 14B). For example, the gel packet can have a handle shape, or a shape that has a wider end portion (for easily gripping and squeezing between a user's thumb and fingers) and a narrower end portion (for extending out from between the user's thumb and finger in a easily controllable direction).

In some embodiments, the gel application system 1400 includes a tear section 1404 at the narrower end of the gel packet. The tear section 1404 may have a configuration similar to the tear sections 1302 and 1304 described herein. After tearing away the tear section 1404, a user can squeeze gel from the gel application system 1400 by applying a squeezing pressure on the gel packet 1402 to discharge a desired amount of gel from the interior of the gel packet, through an opening formed by the removal of the tear section 1404. In some embodiments, to expel the gel from the gel packet, the user pinches the wider end of the gel packet 1402, or bends or folds the packet over.

In some embodiments, the gel application system 1400 is made from multiple materials that create an integrated, semi-rigid tip that aids in applying and controlling the application of gel from the gel packet 1402. For example, the gel application system 1400 can be manufactured using two separate sheets of material that are attached to each other along their edges (e.g., via vacuum sealing, heat sealing, and the like). In some embodiments, a first sheet is made from a flexible, non-rigid material, such as, but not limited to a flexible plastic, rubber, metal foil, or the like, and may be transparent for allowing a user to view the remaining gel in the packet. In some embodiments, the second sheet is made from a more rigid material material, such as, but not limited to, cardstock or cardboard, rigid plastic, metal, ceramic, composite material and the like, to provide a user more control when dispensing the gel.

FIG. 15A, FIG. 15B, FIG. 15C, FIG. 15D, FIG. 15E and FIG. 15F illustrate perspective views of various gel application systems 1500, 1502, 1504, 1506, and 1508 according to various embodiments.

Each of the gel application systems 1500, 1502, 1504, 1506, and 1508 includes a packet 1510, 1512, 1514, 1516, 1518, respectively, that contains a predetermined amount of gel therein. In some embodiments, the packet 1510, 1512, 1514, 1516 or 1518 may be composed of a material and configuration as described above with regard to the packet 1301 or the packet 1402. Each of the gel application systems 1500, 1502, 1504, 1506, and 1508 also includes a straw or tube 1520, 1522, 1524, 1526 and 1528, respectively, for affixing to a sealed opening of the gel packet for allowing flow of the gel from within the packet, through the tube, and to outside of the gel application system. In some embodiments, affixing of the tube to the packet breaks a seal in the packet to open a pathway for the gel. In some embodiments, the tube is affixed to the packet by a threaded section of the packet on which the tube is screwed on. In other embodiments, the tube is snapped into place within the opening of the packet. In other embodiments, the tube is inserted into the opening of the packet and held in place by friction or press fitting within the opening. In some embodiments, the tube has side flanges or protrusion attached thereon to allow a user to easily grip the tube (such as, but not limited to butterfly wing shaped grips). In some embodiments, the packet is made of a material that is transparent or partially transparent to allow a user to view the contents of the packet.

Referring to FIG. 15A, the tube 1520 is configured to connect and secure to the packet 1510 by placing an end of the tube 1520 into a tube receptacle of the packet 1510, and rotating the tube 1520 or packet 1510 relative to each other in a first direction about the longitudinal axis of the tube 1520, and to disconnect from the packet 1510 by rotating in the opposite direction. In such embodiments, the tube 1520 and the receptacle of the packet 1510 may be configured in any suitable interface for providing connection upon rotation, including but not limited to a screw threading interface, a slot and groove interface, or the like.

Referring to FIG. 15B, in some embodiments, the gel application system 1502 includes a packet 1520 and a straw 1522 extending from the packet 1520. In some embodiments, the packet 1520 is shaped like a handle (or shaped as described above with regard to the packet 1402), to fit inside a user's hand such that the user can easily squeeze the packet. In some embodiments, the straw 1522 has a relatively long lengthwise dimension, for allowing a user to reach locations on a patient or a subject that are, otherwise, hard to access (e.g., because a TCD device or other medical device may otherwise obstruct a path to the patient or the subject). In some embodiments, the tip of the straw has a wide and/or flat mouth (distal end) opposite to the end extending into the packet 1520.

Figure 15D:
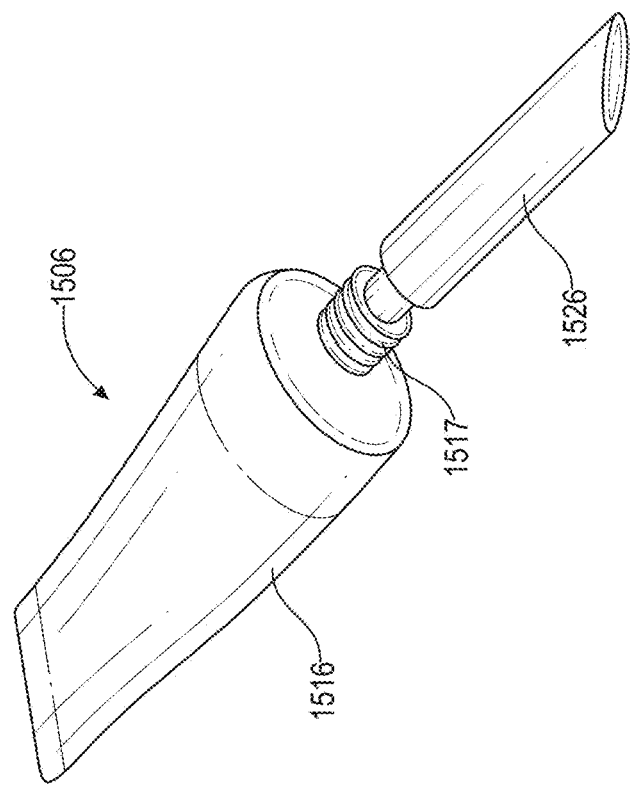
Figure 15C:
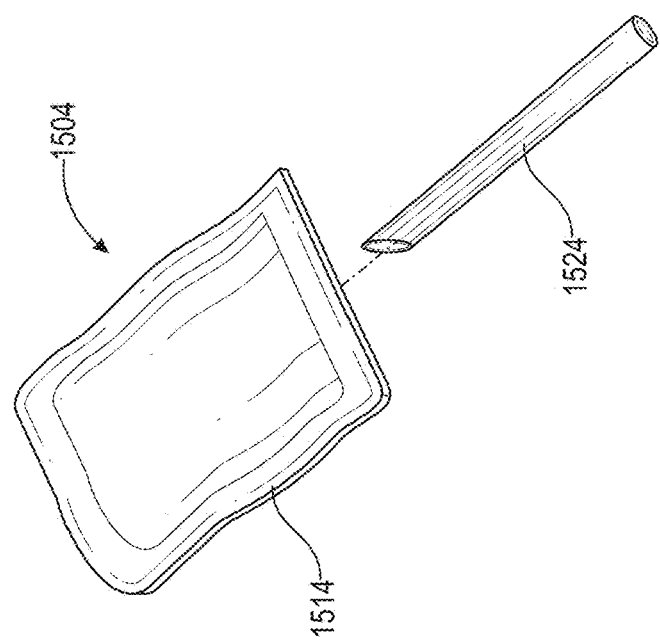

Referring to FIG. 15C, in some embodiments, the gel application system 1504 is similar to the gel application system 1500, except that the tube 1524 is configured to puncture the packet 1514 to enable flow therefrom and through the tube. In some embodiments, the tube 1524 has a sharpened end for puncturing the gel packet 1514.

Figure 15F:
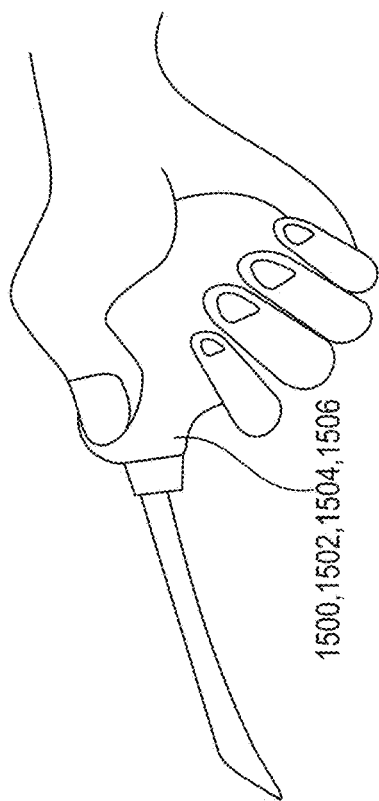
Figure 15E:
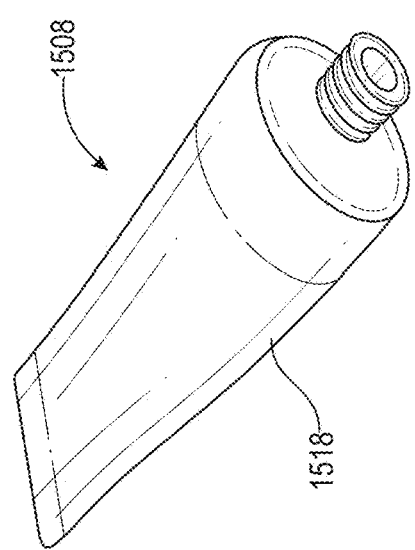

Referring to FIG. 15D, in some embodiments, the gel application system 1506 includes a compressible gel container 1516 that has a tube-like structure. The gel container 1516 has a threaded port 1517. The straw 1526 has a correspondingly threaded end that can be screwed onto the port 1517 of the gel container 1516. Referring to FIG. 15E, in some embodiments, the gel application system 1508 includes a large tube-like gel container 1518 that includes a sealed opening at the end of the container. The sealed opening is configured to be selectively opened, for example, by puncturing or otherwise, to allow the discharge of gel from the container 1518. The packet 1510, 1512, 1514, 1516, 1518 of each of the gel application systems 1500, 1502, 1504, 1506, and 1508 has a size and is made of a material that is sufficiently flexible to allow the packet to be gripped by a user in one hand, as shown in FIG. 15F, and squeezed to compress the interior volume of the packet and cause a volume portion of gel to be expelled through the straw or tube 1520, 1522, 1524, 1526 and 1528.

Figure 16C:
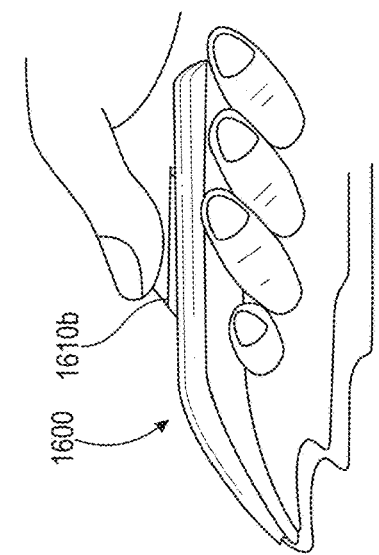
FIG. 16C illustrates a side view of the gel application system including the gel packet container and the gel packet therein according to various embodiments.
Figure 16B:
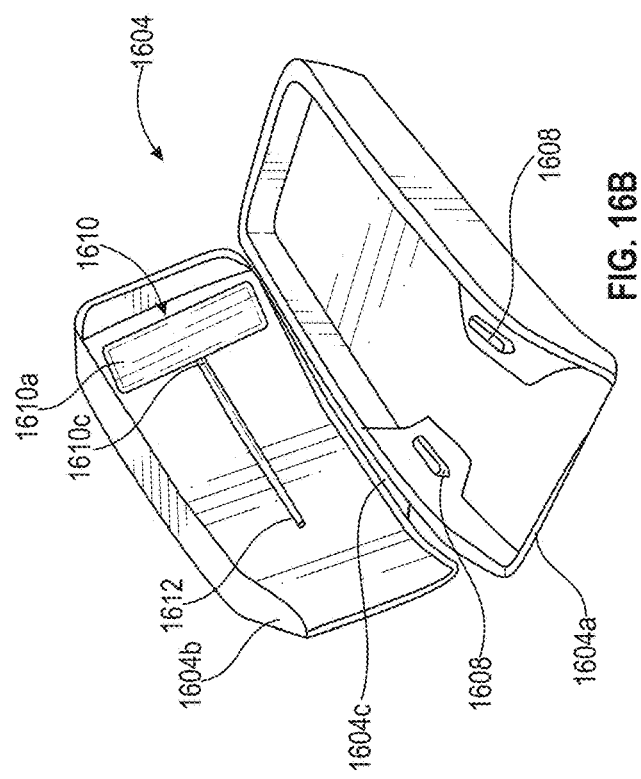
FIG. 16B illustrates a perspective view of a gel packet container of the gel application system according to various embodiments.
Figure 16A:
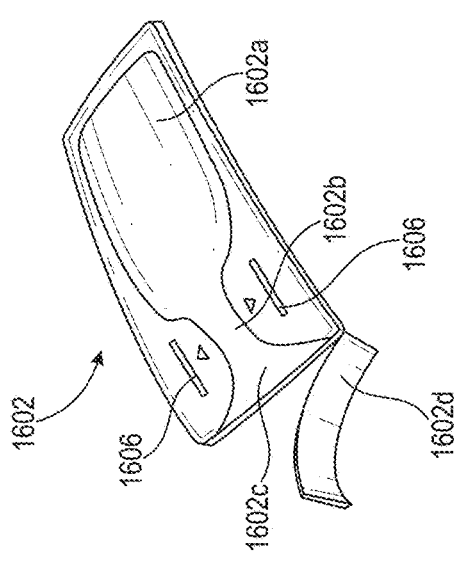
FIG. 16A illustrates a perspective view of a gel packet of a gel application system according to various embodiments.

FIG. 16A illustrates a perspective view of a gel packet 1602 of a gel application system 1600 according to various embodiments. FIG. 16B illustrates a perspective view of a gel packet container 1604 of the gel application system 1600 according to various embodiments. FIG. 16C illustrates a side view of the gel application system 1600 including the gel packet container 1604 having the gel packet 1602 therein, according to various embodiments.

In some embodiments, the gel packet container 1604 includes a base portion 1604a and a lid portion 1604b. The base portion 1604a and the lid portion 1604b are each made from a generally rigid material, such as, but not limited to plastic, metal, wood, cardboard, ceramic, composite material or the like. In some embodiments, the gel packet container 1604 is configured to be disposed of after use or after a predefined number of uses. The lid portion 1604b is coupled to the base portion 1604a through a hinge portion 1604c. In some embodiments, the hinge portion 1604c is a living hinge that is unitary with the base portion 1604a and the lid portion 1604b. In other embodiments, the hinge portion 1604c includes any suitable hinge structure that connects the lid portion 1604b with the base portion 1604a and allows the lid portion 1604b to pivot between an open and a closed position relative to the base portion 1604.

The base portion 1604a of the gel packet container 1604 includes a receptacle region in which the gel packet 1602 may be received. In some embodiments, the base portion 1604a includes one or more (or a plurality) of registration features 1606 for alignment of the gel packet 1602 within the receptacle region. In some embodiments, the gel packet 1602 includes one or more (or a plurality of) registration features 1608 for alignment of the gel packet 1602 within the receptacle region of the base portion 1604a. In some embodiments, each of the gel packet 1602 and the base portion 1604a include one or more (or a plurality of) registration features 1606 and 1608 for alignment of the gel packet 1602.

In the embodiment of FIGS. 16A and 16B, the registration features 1608 on the gel packet 1602 are a pair of slot-shaped holes or slits. In the embodiment of FIGS. 16A and 16B, the registration features 1606 on the base portion 1604a are a pair of elongated protrusions configured to fit within the slot-shaped openings. In other embodiments, the registration features 1608 may include holes, openings, indentations or the like, of any suitable shape and arrangement, and the registration features 1606 may include shapes that correspond with or otherwise mate with the shape and arrangement of registration features 1608. In other embodiments, the registration features 1606 may include one or more slits, holes, openings, indentations or the like, while the registration features 1608 include one or more protrusions configured to engage (or mate with) the registration features 1606. The registration features are configured or arranged (or both) such that when the gel packet container 1604 is properly received within the receptacle region of the base portion 1604a, the registration features 1606 and the registration features 1608 mate. However, if the gel packet container 1604 is not properly aligned within the receptacle region of the base portion 1604a, then the registration features 1606 and 1608 do not mate. In some embodiments, once the gel packet 1602 is properly placed and aligned within the gel packet container 1604, the lid portion 1604b of the container 1604 can be closed shut over the base portion 1604a, to enclose (or partially enclose) the gel packet 1602 within the container 1604.

The gel packet 1602 may be composed of a material and configuration as described above with regard to any one or more of the packets 1301, 1402, 1510, 1512, 1514, 1516 or 1518. In some embodiments, the gel packet 1602 includes an interior volume 1602a for containing gel, where the interior volume includes a narrowed neck portion 1602b and an outlet portion 1602c. In some embodiments, the gel packet 1602 includes a tear section 1602d located across the outlet portion 1602c, to seal the outlet portion (and inhibit gel from flowing from the interior volume of the gel packet 1602, but that is removable (by tearing) to open the outlet portion 1602c and allow gel to be expelled from the gel packet 1602. In some embodiments, the tear section 1602d on the gel packet 1602 is configured the same or similar to other tear sections described herein, such as tear sections 102a, 1302, 1304 and 1404. The tear section 1602d may include one or more lines of perforations, indentations, thin regions or weaker regions on or in the flexible material forming the gel packet 1602, to enhance the user's ability to tear the tear section, as described above. In some embodiments, the registration features 1606 on the gel packet 1602 are arranged adjacent, and on both sides of the narrowed or neck portion 1602b of the interior volume of the gel packet 1602. In that manner, the registration features 1606, when engaged with the registration features 1608, ensure proper lateral alignment of the gel packet 1602 within the container 1604, such that the outlet portion 1602c is properly aligned with an outlet opening of the container 1604. In addition, the registration features 1606 and 1608, when engaged, help retain the gel packet 1602 within the container 1604 and inhibit movement of the gel packet 1602, during operation.

The lid portion 1604b of the container 1604 includes a force applicator (or squeezing) feature 1610, that allows a user to apply a squeezing (or compression) force on the gel packet 1602 within the container 1604, in a controlled manner. The force applicator feature 1610 includes a squeezing member 1610a located on the interior-facing side of the lid portion 1604b, a trigger or handle 1610b located on the exterior-facing side of the lid portion 1604b, and a central section 1610c connecting the squeezing member and the trigger or handle together. The central section 1610c of the force applicator feature 1610 extends through a slot-shaped opening 1612 in the lid portion 1604b and allows the force applicator feature 1610 to move (or slide) along the length of the slot-shaped opening 1612, relative to the lid portion 1604b. The slot-shaped opening 1612 extends along at least a portion of the length dimension of the lid portion 1604b (and of the container 1604). In some embodiments, the slot-shaped opening 1612 extends along at least a portion of the length extending from a location adjacent one end of the lid portion 1604b to a location adjacent the position of the registration members 1608 in the base portion 1604a. The squeezing member 1610a and the trigger or handle 1610b are larger in width than the width of the slot-shaped opening 1612 and, thus, retain the force applicator feature 1610 on the lid portion 1604b.

In some embodiments, the force applicator feature 1610, including the squeezing member 1610a, the trigger or handle 1610b and the central section 1610c are formed in multiple parts that are connected together. In other embodiments, the force applicator feature 1610 may be formed as a single, unitary structure. The force applicator feature 1610 may be made of one or more of any suitable materials having sufficient rigidity to operate in the manner described herein including, but not limited to plastic, rubber, metal, wood, ceramic, composite material or the like. The squeezing member 1610a is formed of a body having sufficient size and rigidity to impart a squeezing or compression force on gel packet 1602 located within the container 1604, to increase the fluid (or gel) pressure in the interior volume of the gel packet 1602 to cause gel to be expelled from the gel packet 1602 when the outlet portion 1602c is open. In some embodiments, the squeezing member 1610a is moveable relative to the lid portion 1604b, in the direction of the slot-shaped opening 1612, between a first position in which the squeezing member 1610a is located adjacent one end of the container (and one end of the slot-shaped opening 1612)

to a second position in which the squeezing member 1610*a* is located adjacent the location of the registration members 1608 (and the second end of the slot-shaped opening 1612).

In operation, a gel packet 1602 as described herein is opened (outlet portion 1602*c* opened) and placed within the container 1604. Then the lid portion 1604*b* is closed over the base portion 1604*a* of the container 1604 while the squeezing member 1610*a* is in the first position. In that position, the squeezing member 1610*a* aligns with one end of the gel packet 1602 (the end opposite to end having the outlet portion 1602*c*) and imparts a compression force onto the gel packet 1602. From that first position, the squeezing member 1610*a* is moveable toward the outlet portion 1602*c* end of the gel packet 1602, along the direction of the slot-shaped opening 1612 in the lid portion 1604*b*. In some embodiments, the squeezing member 1610*a* is moved by a user, upon a user imparting a sufficient force on the trigger or handle 1610*b* to move the trigger or handle 1610*b* in the direction of the outlet portion 1602*c* end of the gel packet 1602, as shown in FIG. 16C. As the trigger or handle 1610*b* (and, thus, the squeezing member 1610*a*) is moved toward the outlet portion 1602*c* end of the gel packet 1602, the squeezing member 1610*a* imparts a force onto the gel packet 1602 to cause gel to be expelled from the open outlet portion 1602*c* of the gel packet 1602. The user may control the amount and rate of flow of gel from the gel packet 1602, by controlling the amount and rate of movement of the trigger or handle 1610*b*.

In some embodiments, the container 1604 includes an outlet opening through which gel expelled from the gel packet 1602 is expelled from the container 1604, for example, onto patient or subject, or onto an applicator or the like. In some embodiments, the outlet opening of the container 1604 may be formed as a gap or open space between the base portion 1604*a* and the lid portion 1604*b*, when the lid portion 1604*b* is closed over the base portion 1604*a*. In other embodiments, the outlet opening of the container 1604 may be provided in the base portion 1604*a* or in the lid portion 1604*b*. In some embodiments, the outlet opening of the container 1604 may form a relatively wide slot for dispensing a relatively wide band of gel or dispensing gel at a relatively fast dispensing rate. In other embodiments, the outlet opening of the container 1604 may be formed narrower, to provide a narrower dispensing band or a lower dispensing rate.

In some embodiments, the outlet opening of the container 1604 receives a portion of the outlet opening 1602*c* end of the gel packet 1602, when the gel packet 1602 is properly received and registered within the container 1604. The engagement of the registration members 1606 and 1608 as described herein can help hold the gel packet 1602 in place, such that the outlet opening 1602*c* of the gel packet 1602 remains properly aligned with the outlet opening of the container 1604, while the squeezing member 1610*a* moves to impart a compression force on the gel packet 1602.

Accordingly, the container 1604 and one or more gel packets 1602 provide a gel application system that allows a user to control the dispensing of gel from one or more gel packets 1602 in a controlled manner. In some embodiments, the gel packet container 1604 is configured to be reusable with respect to a single patient, and a user can replace gel packets 1602 within the gel packet container 1604 during use.

Figure 17B:
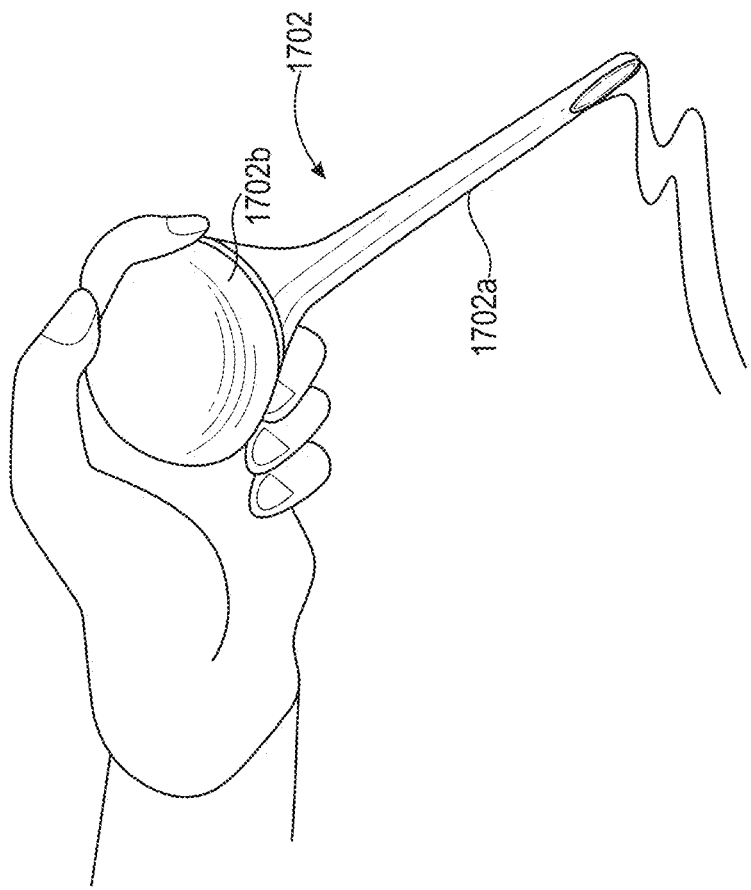
FIG. 17B illustrates a side view of a user utilizing the gel application system shown in FIG. 17A according to various embodiments.
Figure 17A:
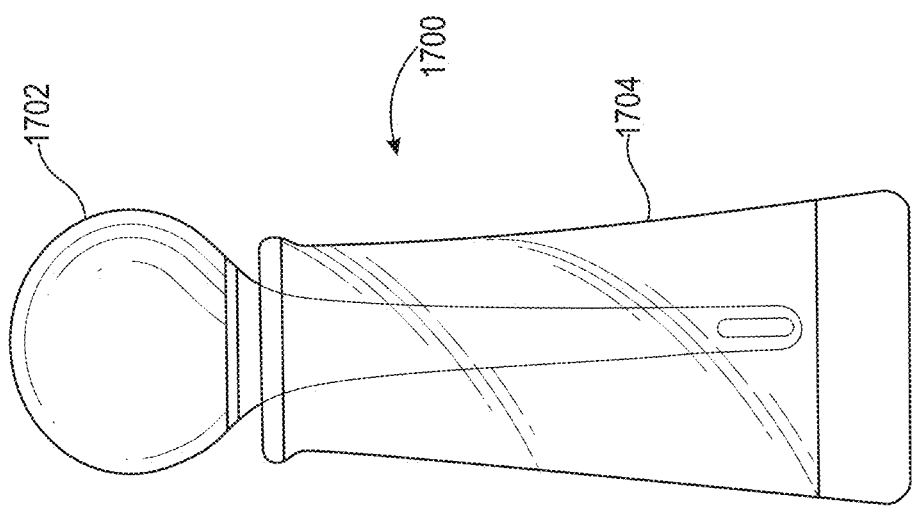
FIG. 17A illustrates a side view of a gel application system according to various embodiments.

FIG. 17A illustrates a side view of a gel application system 1700 according to various embodiments. FIG. 17B illustrates a side view of a user utilizing the gel application system 1700 shown in FIG. 17A according to various embodiments.

In some embodiments, the gel application system 1700 includes a syphon device 1702 and a gel container 1704. In some embodiments, the syphon device includes an elongated tube or straw section 1702*a* and a squeezable (compressible) section 1702*b*. The squeezable section 1702*b* has an enclosed, hollow interior volume that is in fluid flow communication one end of the straw section 1702*a*. The squeezable section 1702*b* is made of any suitable material that is sufficiently flexible and resilient to operate as described herein, such as, but not limited to rubber, plastic or the like. In some embodiments, the squeezable section 1702*b* is made of a material that is sufficiently flexible and resilient to be squeezed and compressed by the squeezing force of a user's hand, and to return to its pre-squeezed shape when the squeezing force is removed. In some embodiments, the squeezable section 1702*b* has a partially spherical or ball-shaped portion that easily fits within a user's hand.

The tube or straw section 1702*a* may be made of the same material as the squeezable section 1702*b*, or may be made of a different material, such as a more rigid material including, but not limited to plastic, rubber, metal, ceramic, cardstock, composite material, or the like. In some embodiments, the tube or straw section 1702*a* is made of a material that is transparent or partially transparent to allow a user to view a volume of gel within the tube or straw section. In some embodiments, the tube or straw section 1702*a* also includes markings along its length dimension to identify one or more (or a plurality of) levels corresponding to amounts or volume measures of gel within the tube or straw section. The tube or straw section 1702*a* has an open end or tip through which gel contained in the tube or straw section 1702*a* may be dispensed. The open end or tip is opposite to the end connected in fluid flow communication with the interior volume of the squeezable section 1702*b*. The open end or tip of the tube or straw section may include an angled or beveled edge. The angled or beveled end can provide an enlarged opening relative to a perpendicular end, for increased flow rate. Alternatively or in addition, the angled or beveled end can allow a user to apply a relatively wide band of gel from the tip of the tube or straw section 1702*a*.

The squeezable section 1702*b* is configured to be squeezed by a user to force air or fluid from the interior volume of the squeezable section 1702*b* into the tube or straw section 1702*a*, to increase the fluid pressure within the tube or straw section. Release of a squeezing force on the squeezable section 1702*b* allows the squeezable section 1702*b* to return to its un-squeezed state (and allows the interior volume of the squeezable section 1702*b* to expand), and apply a suction force on fluid within the tube or straw section.

The gel container 1704 includes one or more container walls and a base portion that define and surround an interior volume containing gel. The gel contained by the container 1802 may be any suitable gel used in conjunction with healthcare, including, but not limited to, ultrasound gel used in connection with ultrasound emitting devices (e.g., Transcranial Doppler (TCD) devices) and other gel as described herein with regard to gel 104. The container (including the one or more walls and base portion) may be made as a single, unitary structure or may be made from multiple components connected together, and may be made of any suitable material or materials including, but not limited to, plastic, metal, ceramic, composite material, and the like. The container 1704 has an opening at one end (the top end in FIG. 17A), opposite to an end (the bottom end in FIG. 17A) at which the base portion is located. The base portion may have a flat or sufficiently horizontal surface configuration to allow the container to rest on a horizontal surface (such as, but not limited to a table top surface, a tray surface, or the like), with the open end of the container 1704 facing upward. The open end of the container has a size and a shape to receive the tube or straw section 1702*a* of the syphon device 1700, for example, as shown in FIG. 17A. In some embodiments, the container wall defines a container volume have a depth large enough to receive a sufficiently length of the tube or straw section 1702*a* to allow the syphon device 1700 to be supported by the container 1704 in an orientation in which the squeezable section 1702*b* is located outside of the container 1704 and can be easily gripped by a user.

In some embodiments, the elongated tube or straw section 1702*a* of the syphon device 1702 is submerged into the gel container such that the gel can flow from the container into the syphon device. A user may create suction to draw gel into the syphon device 1702, by squeezing and compressing the squeezable section 1702*b* and then releasing the squeezing (compression) force from the squeezable section 1702*b* while the tip end of the tube or straw section 1702*a* is submerged in gel within the container 1704. In some embodiments, the gel flows into the tube or straw section 1702*a*, but not into the squeezable section 1702*b*. In other embodiments, the gel flows into the tube or straw section 1702*a* and into the squeezable section 1702*b*. Then, the user can squeeze the squeezable section 1702*b* to selectively discharge gel from the syphon device 1702 onto a patient or subject (e.g., as shown in FIG. 17B).

Figure 18B:
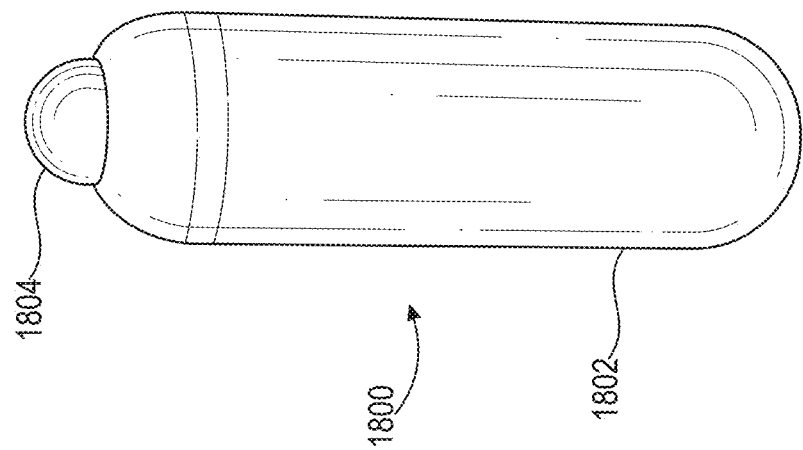
FIG. 18A and FIG. 18B illustrate various views of a gel application system according to various embodiments.
Figure 18A:
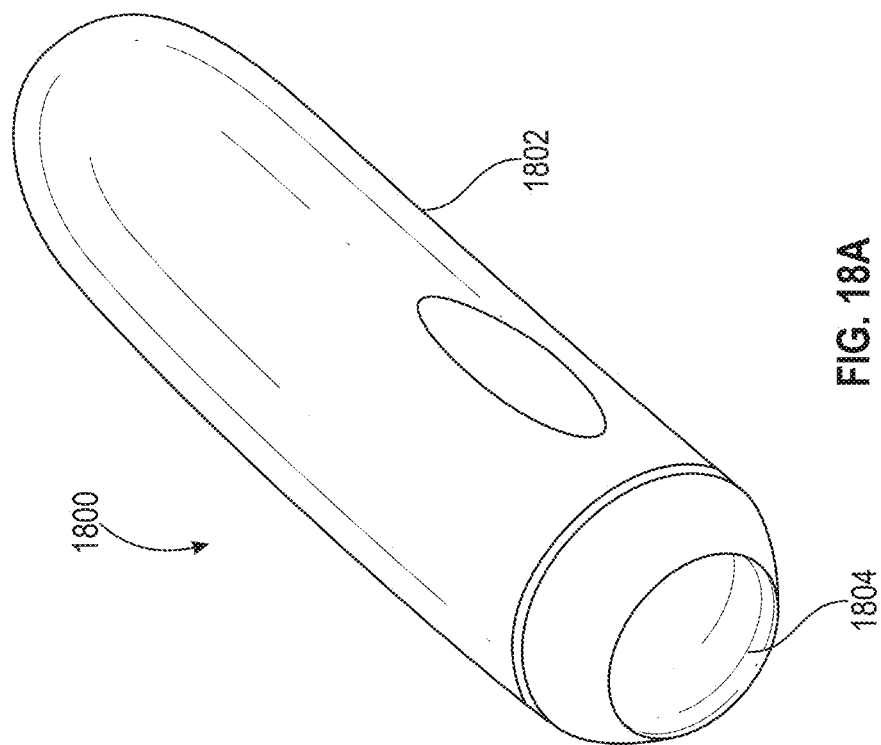

FIG. 18A and FIG. 18B illustrate various views of a gel application system 1800 according to various embodiments.

In some embodiments, the gel application system 1800 includes a roller applicator assembly. For example, the gel application system 1800 includes a container 1802 having an interior volume for containing a gel. The gel contained by the container 1802 may be any suitable gel used in conjunction with healthcare, including, but not limited to, ultrasound gel used in connection with ultrasound emitting devices (e.g., Transcranial Doppler (TCD) devices) and other gel as described herein with regard to gel 104. The gel application system 1800 also includes a roller applicator 1804, such as a roller ball attached to an end of the container and in contact with (on an interior facing portion of its surface) gel contained within the container 1802. The roller ball of the roller applicator 1804 may fit within a socket that allows the roller ball to rotate or roll within the socket. The roller boll and socket of the roller applicator 1804 may be made of any suitable material or materials having sufficient rigidity to operate as described herein, including, but not limited to plastic, rubber, metal, ceramic, composite material, or the like.

The container 1802 may be made of any suitable material having sufficient flexibility and rigidity to operate as described herein, including, but not limited to plastic, rubber, metal, ceramic, composite material, or the like. In some embodiments, the container 1802 is made of a material having sufficient flexibility and resilience to be squeezed and compressed by a user's hand, and then return to its unsqueezed shape upon removal of the squeezing force. In such embodiments, a user may squeeze the container 1802 to compress and increase the fluid (or gel) pressure of the interior volume of the container 1802, to force gel out of the container 1802 and around the roller applicator 1804.

In some embodiments, the gel application system 1800 is configured such that a user may hold the container 1802 in one hand and press the roller ball of the roller applicator 1804 against a surface (e.g., a side of a patient's or subject's head) such that the roller ball becomes recessed within its socket on the container a sufficient amount to form (or enlarge) one or more openings or a circular slit along the outer surface of the roller ball, to allow gel to seep through the openings and onto the roller ball of the roller applicator 1804. In some embodiments, the user squeezes the container to increase the fluid (or gel) pressure within the container, to push gel onto and around the roller ball of the roller applicator 1804. As such, the user can control the release of gel onto a patient or subject via the roller applicator 1804.

Figure 19:
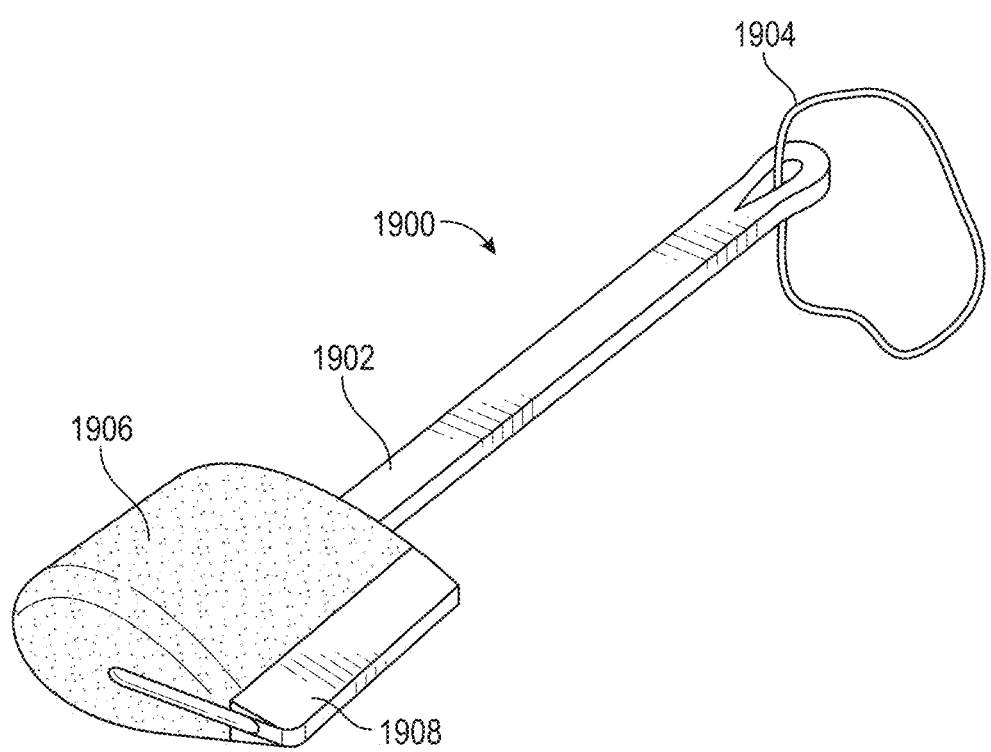
FIG. 19 illustrates a perspective view of a gel applicator according to various embodiments.

FIG. 19 illustrates a perspective view of a gel applicator 1900 according to various embodiments.

In some embodiments, the gel applicator 1900 is configured to apply gel onto a patient or subject (for example, but not limited to a patient's or subject's head) or adjust positioning of gel that is already applied. In some embodiments, the gel applicator 1900 includes a handle 1902, a lanyard 1904, a sponge 1906, and an edge member 1908. In some embodiments, the handle 1902 has a first end to which the sponge 1906 is attached and a second end (opposite the first end) to which the lanyard 1904 is attached. The edge member 1908 is attached to an edge of the sponge 1906 or is formed on an edge of the sponge 1906.

In some embodiments, the edge member 1908 is made of a silicone material to define a silicone edge or tip for allowing a user to control the spreading or adjustment of gel. In other embodiments, the edge member 1908 may be made of other suitable material including, but not limited to plastic, rubber, metal, ceramic, cardstock, cardboard, composite material or the like. In some embodiments, the edge member 1908 has a generally wedge or beveled shape to form a small width distal edge.

The sponge 1906 may be made of any suitable material, for example, a soft, flexible, or resilient material, such as, but not limited to, closed cell foam, open cell foam, self-skinning open or closed cell foams, cast, aerated, or extruded silicone or urethane, polyurethane, or the like. The sponge 1906 may be attached to the handle 1902 in any suitable manner including, but not limited to welding, adhesives, friction or press fittings, or the like. In some embodiments, the sponge 1906 is attached to the handle 1902 by heat sealing or other mechanisms that do not require additional materials, to minimize potential contaminants.

The lanyard 1904 may have a string or rope-like configuration and may be made of any suitable material such as, but not limited to, nylon, plastic, fabric, cotton, metal, or the like. The lanyard 1904 may be attached to the handle 1902 in any suitable manner including, but not limited to tying, adhesives, or the like. In some embodiments, the second end of the handle 1902 has an opening through which the lanyard 1904 extends in a loop.

The handle 1902 may be made of any suitable material having sufficient rigidity to support the sponge 1906 and operate as described herein, including, but not limited to plastic, rubber, metal, wood, ceramic, composite material, or the like. The handle 1902 may have a length dimension of sufficient length to allow a user to grip the handle 1902 and move the sponge 1906 and the edge member 1908 along a surface of a patient or subject (e.g., along a surface of the patient's or subject's head) to apply, spread or scrape gel on the surface of the patient or subject.

Figure 20A:
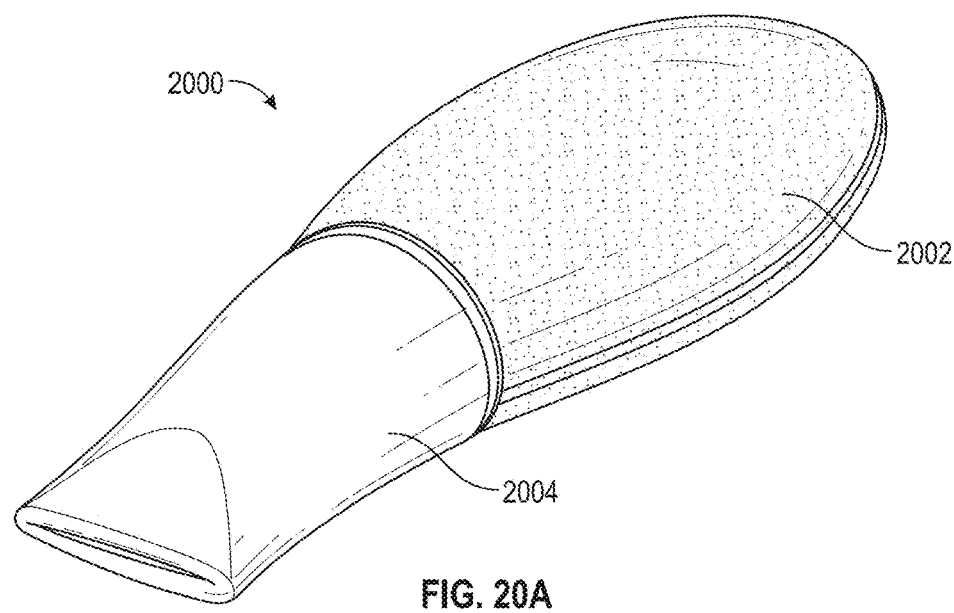
FIG. 20A, FIG. 20B, and FIG. 20C illustrate various views of a gel application system according to various embodiments.
Figure 20B:
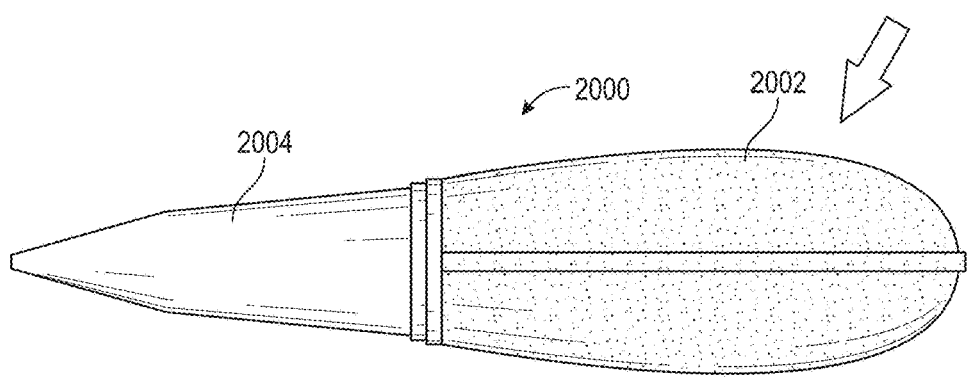
Figure 20C:
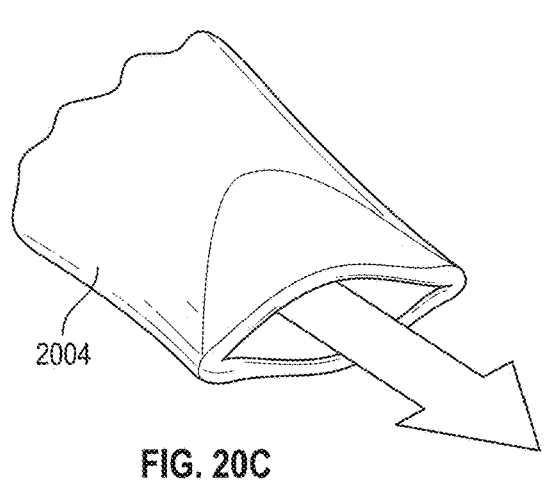

FIG. 20A, FIG. 20B, and FIG. 20C illustrate various views of a gel application system 2000 according to various embodiments.

In some embodiments, the gel application system 2000 includes a gel container 2002 and a flexible tip member 2004. The gel container 2002 may be made from any suitable material for retaining gel as described herein such as, but not limited to, polymer, plastic, rubber, and the like. In some embodiments, the gel container 2002 may be made of one or more materials and a configuration that is the same or similar to that of other gel containers described herein, including gel container 102, 806, 809, 1002, 1301, 1402, 1510, 1512, 1514, 1516, 1518 or 1602. The gel container 2002 has an interior volume containing gel.

In other embodiments, the container 2002 is made of one or more materials connected and sealed at one or more seams to form an enclosed, hollow interior volume. In some embodiments, the gel container 2002 is made of one sheet of flexible material that is folded and sealed at its peripheral edge to form an enclosed interior volume for containing the gel. In other embodiments, the gel container 2002 is made of two sheets of flexible material that are sealed together at their peripheral edges to form an enclosed interior volume for containing the gel. The container 2002 may be sealed along its edge or edges by any suitable mechanism including, but not limited to vacuum sealing, heat sealing, adhesives and the like. In some embodiments, the container 2002 is made of a material that is sufficiently flexible to allow a user to squeeze the container 2002 with manual force (such as by hand), to compress the pocket-like hollow interior and apply or increase the pressure of the fluid (or gel) in the interior volume of the gel container 2002.

The gel contained by the container 2002 may be any suitable gel used in conjunction with healthcare, including, but not limited to, ultrasound gel used in connection with ultrasound emitting devices (e.g., Transcranial Doppler (TCD) devices) and other gel as described herein with regard to gel 104. The gel container 2002 has an end through which gel may be expelled from the interior volume, and that is connected to flexible tip member 2004 such that the interior volume of the container 2002 is in fluid (or gel) flow communication with the tip member 2004.

The flexible tip member 2004 has a first end connected to the container 2002, in flow communication with the interior volume of the container 2002, a second end that defines an outlet tip, and a central passage through which gel may pass from the first end to the second end and be expelled through the outlet tip. The flexible tip member 2004 may be attached to the gel container 2002 in any suitable manner including, but not limited to adhesive, welding, thermal bonding, threaded connector, snap connector, friction or press fit connection, or the like. The flexible tip member 2004 may be made of any suitable material having sufficient flexibility and resilience to operate as described herein, including, but not limited to silicon, rubber, plastic, or the like.

In some embodiments, the outlet tip of the flexible tip member 2004 includes a self-closing flexible tip (such as, but not limited to a flexible silicon tip) that is flexible and is configured to remain in a closed (or sealed) state with sufficient force that gel is not able to pass through the outlet tip unless an external force above a threshold is applied to the gel container 2002. In such embodiments, the material of the flexible tip member 2004 may have a natural resilience or may be configured to provide or enhance its resilience to be in a closed (or sealed) state, unless the external force above the threshold is applied. In some embodiments, the external force is provided by a user squeezing the gel container 2002 with a sufficient force to increase the fluid (or gel) pressure within the gel container 2002 and the flexible tip member 2004, which causes the outlet tip of the flexible tip member 2004 to open and allow gel to flow out of the outlet tip, as shown in FIG. 20C. However, once the external force is removed, the outlet tip of the flexible tip member 2004 closes under its own resilience as shown in FIG. 20A and FIG. 20B. In some embodiments, the outlet tip of the flexible tip member 2004 has a slot-shaped opening that is elongated in one direction (e.g., a width dimension) relative to another direction (e.g., a height dimension). In some embodiments, the elongated shape of the slot-shaped opening and the flexible material of the outlet tip enhances the ability of the outlet tip to automatically close with sufficient force and inhibit flow of gel out of the slot shaped opening, once the external force is removed.

In some embodiments, the gel application system 2000 is configured such that a user may hold the container 2002 in one hand and direct the flexible tip member 2004 toward or against a surface (e.g., a side of a patient's or subject's head). In some embodiments, the user applies a force (by squeezing) the container 2002 to increase the fluid (or gel) pressure within the container, to push gel out of the container 2002 and through the central channel of the flexible tip member 2004 to, and through the outlet tip of the flexible tip member 2004. The user may remove the applied force, to cause the outlet tip to close and reseal itself, once a suitable volume of gel has been expelled. Accordingly, the user can control the release of gel onto a patient or subject and easily stop the flow of gel by simply removing or reducing the squeezing force on the container 2002 sufficient to allow the flexible tip member 2004 to close and seal itself.

FIG. 21A, FIG. 21B, FIG. 21C, and FIG. 21D illustrate gel applicators 2100, 2102, 2104, and 2106 according to various embodiments.

In some embodiments, the gel applicator 2100 includes a scoop, shell or cup-shaped body 2100*a* that is made from any suitable rigid, but partially flexible material, such as, but not limited to, plastic, silicon, rubber, cardstock, cardboard, ceramic, composite material, or the like. In some embodiments, the body 2100*a* of the gel applicator 2100 includes a ridge 2100*b* such that a user can easily grip the gel applicator 2100. In some embodiments, the ridge 2100*b* is located on one edge and forms a handle that allows a user to grip the gel applicator 2100 and move the shell or cup-shaped body of the gel applicator 2100 as a scoop to scoop up or hold a volume of gel. In some embodiments, the ridge or handle portion 2100*b* of the gel applicator 2100 is formed thicker than other portions of the body forming the scoop, to provide greater stability and control on the handle portion. In some embodiments, the body of the gel applicator includes an edge 2100*c* that is formed relatively thin, compared to other portions of the body, for assisting with guiding, spreading or scraping gel.

Figure 21A:
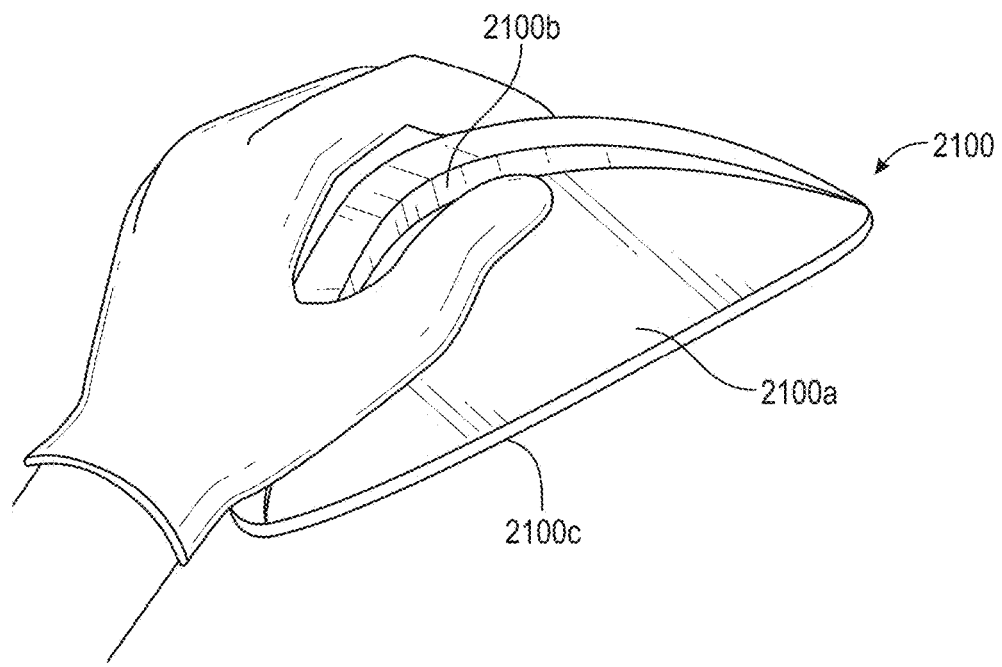
FIG. 21A, FIG. 21B, FIG. 21C, and FIG. 21D illustrate various gel applicators according to various embodiments.
Figure 21B:
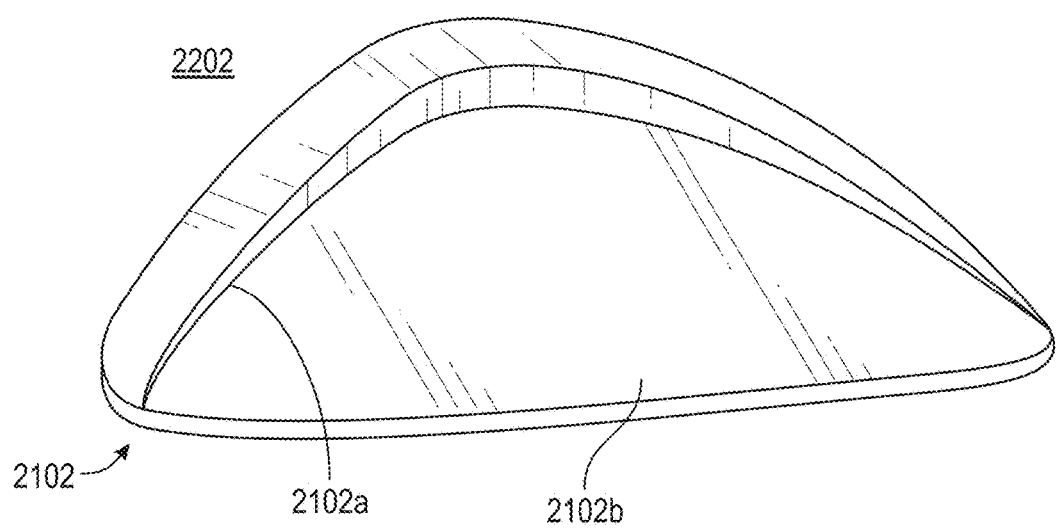
Figure 21C:
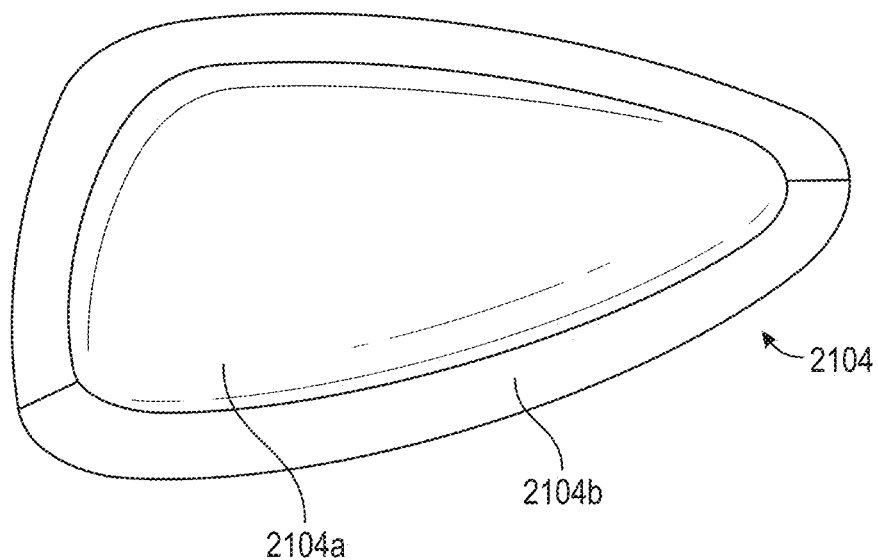
Figure 21D:
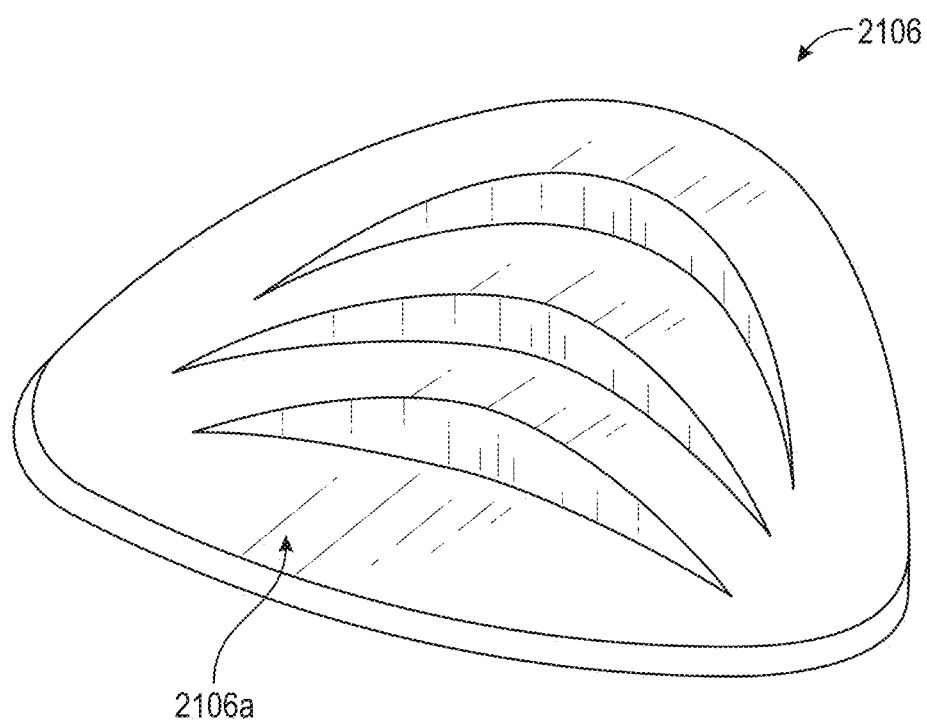

In some embodiments, as shown in the example of the gel applicator 2102 of FIG. 21B, the body 2102*a* of the gel applicator may have a generally symmetrical shape (symmetrical about a center axis 2102*b* of the body). In some embodiments, as shown in the example of FIG. 21C, the body 2104*a* of the gel applicator may have a gel controlling mechanism along its edge. For example, the gel applicator 2104 has a thin, silicone edge 2104*b* for aiding in guiding the gel. In other embodiments, the gel controlling mechanism may include other edge configurations or materials or other features attached to the edge to allow the user to spread, layer, scrape or otherwise control the application of gel on a surface of a patient or subject.

In any of the embodiments of FIG. 21A, FIG. 21B, FIG. 21C, and FIG. 21D, gel can be scooped into, poured, or otherwise directly applied onto the shell or cup-shaped body of the gel applicator, for then applying to a patient or subject from the gel applicator. In some embodiments, gel may be applied to the patient or the subject from the gel applicator, by spreading and guiding gel from the gel applicator onto the patient or subject. In any of those or other embodiments, the body of the gel applicator may have one or more grooves or ribs 2106a forming a ribbed pattern, as shown in the example of the gel applicator 2106 of FIG. 22D. In such embodiments, gel that is applied to the body of the gel applicator is held within the grooves or between ribs and less likely to inadvertently spill from the gel applicator (e.g., when transporting the gel to the subject with the gel applicator).

FIG. 22A, FIG. 22B, FIG. 22C, and FIG. 22D illustrate various views of a gel applicator 2200 according to various embodiments.

In some embodiments, the gel applicator 2200 includes a handle 2202 and an application section 2204. The handle 2202 has a length dimension, and the application section 2204 is provided on or near one end of the length dimension of the handle. The application section 2204 may be secured to the handle 2202 in any suitable manner including, but not limited to adhesive, welding, thermal boding, friction or press fit, or the like. In some embodiments, the application section 2204 is molded onto or co-molded with the handle 2202. In some embodiments, the application section 2204 is formed integral with the handle 2202, as a unitary body.

The handle 2202 may be made of any suitable material having sufficient rigidity to operate as described herein such as, but not limited to plastic, metal, wood, ceramic, composite material, cardboard, or the like. In some embodiments, the application section 2204 includes a plurality of bristles. In some embodiments, the bristles are made from any suitable material for guiding and spreading gel, such as, but not limited to, silicone, plastic, rubber, or the like. The bristles are configured and arranged to retain a volume of gel. Accordingly, when a volume of gel that is applied to the gel applicator 2200, the gel is held within the bristles. The handle 2202 and application section 2204 are configured to provide the user with improved guiding capabilities, for controlling and guiding the application of the gel onto a surface of a patient or a subject.

Figure 22C:
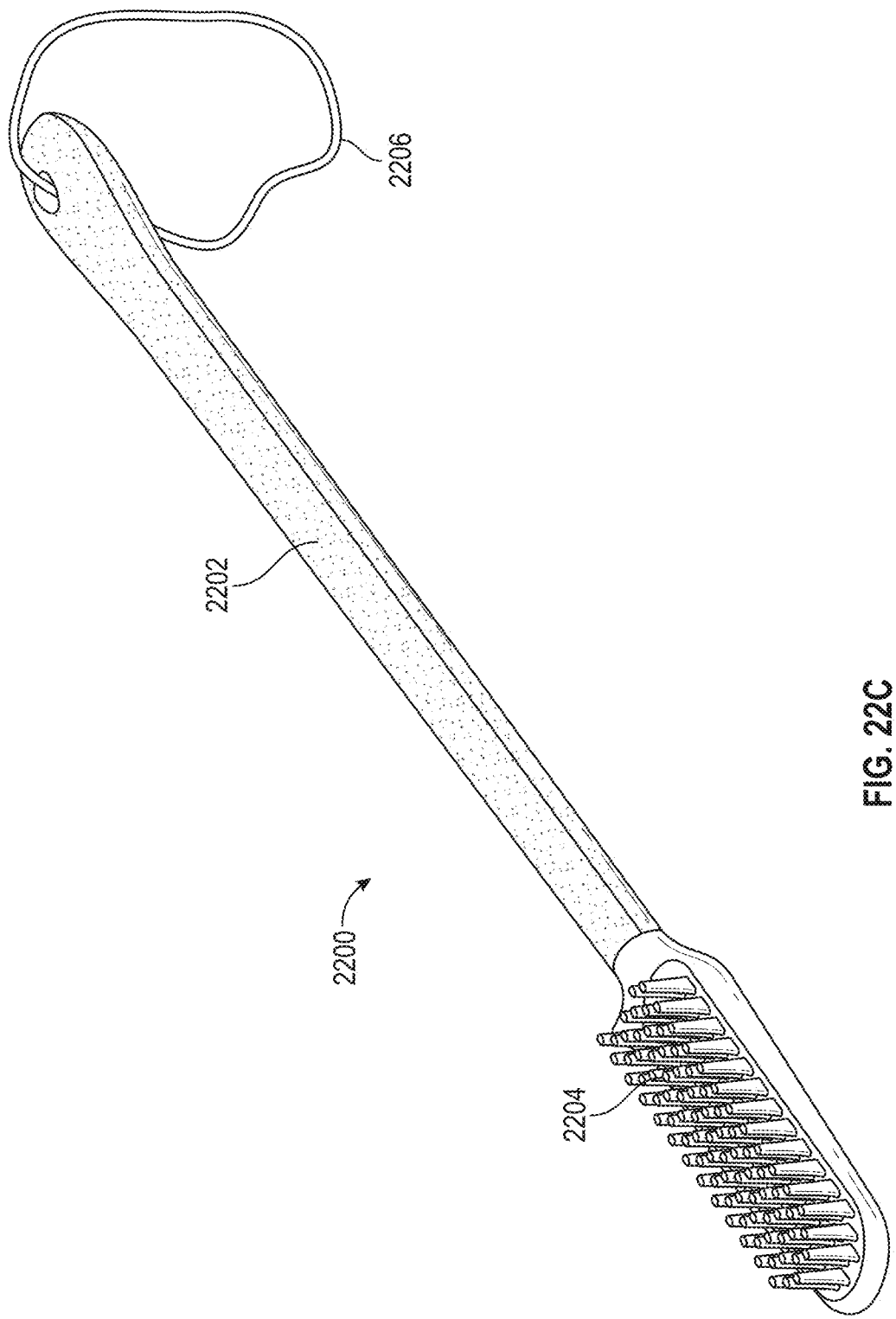

In some embodiments, a lanyard 2206 (such as described above with regard to the lanyard 656) is attached to the handle 2202. The lanyard 2206 may be attached to the handle 2202 in any suitable manner including, but not limited to the manners described above for lanyard 656, as well as by looping the lanyard 2206 through a hole in the handle (such as, but not limited to, a hole near the second end of the handle, opposite to the end to which the application section 2204 is attached, as shown in FIG. 22C).

Figure 22D:
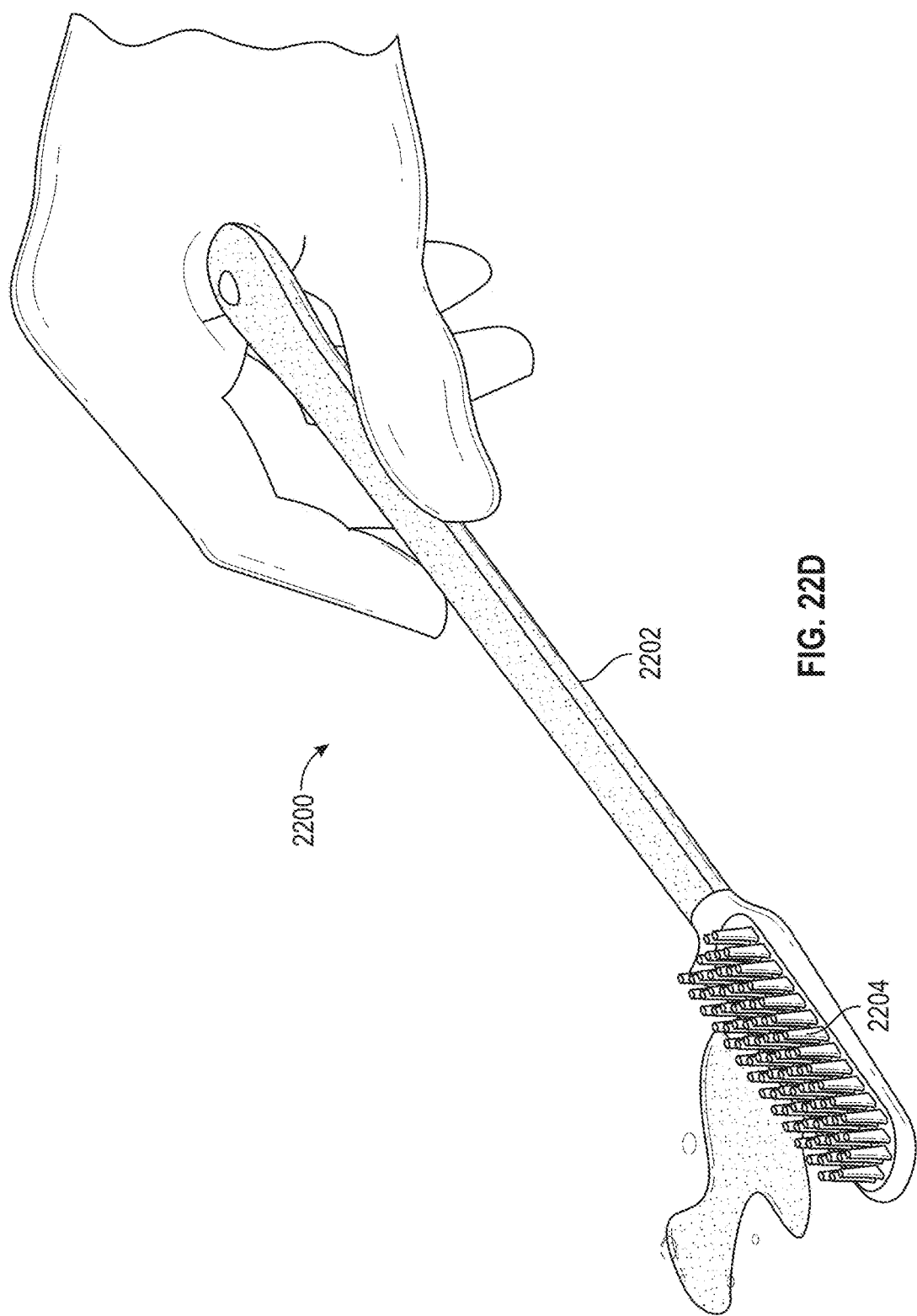

In some embodiments, the handle 2202 is configured to be gripped and held by a hand of a user along its length dimension, with the application section 2204 extending out from the user's hand, for example, as shown in FIG. 22D. The user may apply gel to a surface of a patient or subject by contacting the surface with the application section 2204, or with gel retained by the application section 2204 and move or swipe the surface to spread the gel along the surface in a controlled manner.

FIG. 23A, FIG. 23B, FIG. 23C and FIG. 23D illustrate various gel applicators 2300, 2310, and 2320 according to various embodiments. Each of the gel applicators 2300, 2310, and 2320 includes a handle and a gel controlling mechanism on the handle. The handle has a length dimension, and the gel controlling mechanism is provided on or near one end of the length dimension of the handle. The gel controlling mechanism may be secured to the handle in any suitable manner including, but not limited to adhesive, welding, thermal boding, friction or press fit, or the like. In some embodiments, the gel controlling mechanism is molded onto or co-molded with the handle. In some embodiments, the gel controlling mechanism is formed integral with the handle, as a unitary body.

The handle may be made of any suitable material having sufficient rigidity to operate as described herein such as, but not limited to plastic, metal, wood, ceramic, composite material, cardboard, or the like. In some embodiments, the gel controlling mechanism is made from silicone (or other suitable material as described with regard to the gel spreading mechanisms 602 and 652 and the scraper 654) and is raised and has a scooped edge for guiding gel. In some embodiments, the gel controlling mechanism may have a configuration and operates as described herein with regard to the gel spreading mechanism 602 or 652, or the scraper 654. In other embodiments, the gel controlling mechanism may have other suitable configurations for controlling the application of gel.

Figure 23A:
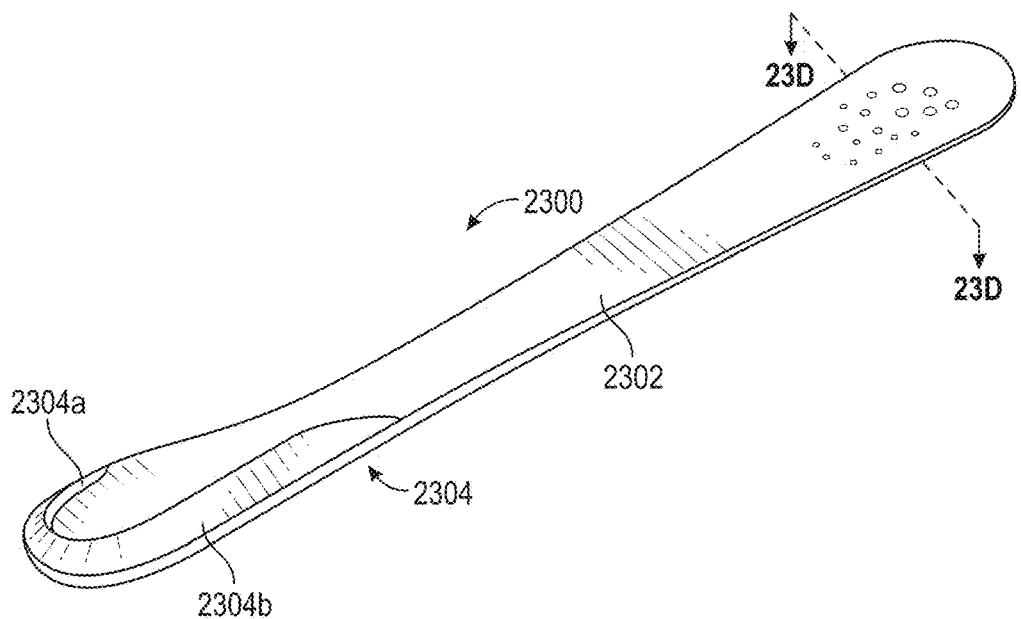
FIG. 23A, FIG. 23B, and FIG. 23C illustrate various perspective views of gel applicators according to various embodiments

In some embodiments, as shown in FIG. 23A, the gel applicator 2300 includes a handle 2302 and a gel controlling mechanism 2304 that extends around one end of the handle 2302 and has a first length portion 2304a that extends along a first length of one side edge of the handle 2304 and a second length portion 2304b that extends along a second length of a second side (opposite to the first side) of the handle 2302. The second length is shorter than the first length. Accordingly, the gel applicator 2300 provides the user with a controlling mechanism 2304 having two different side edges, for different levels of control of application or spreading of gel.

Figure 23B:
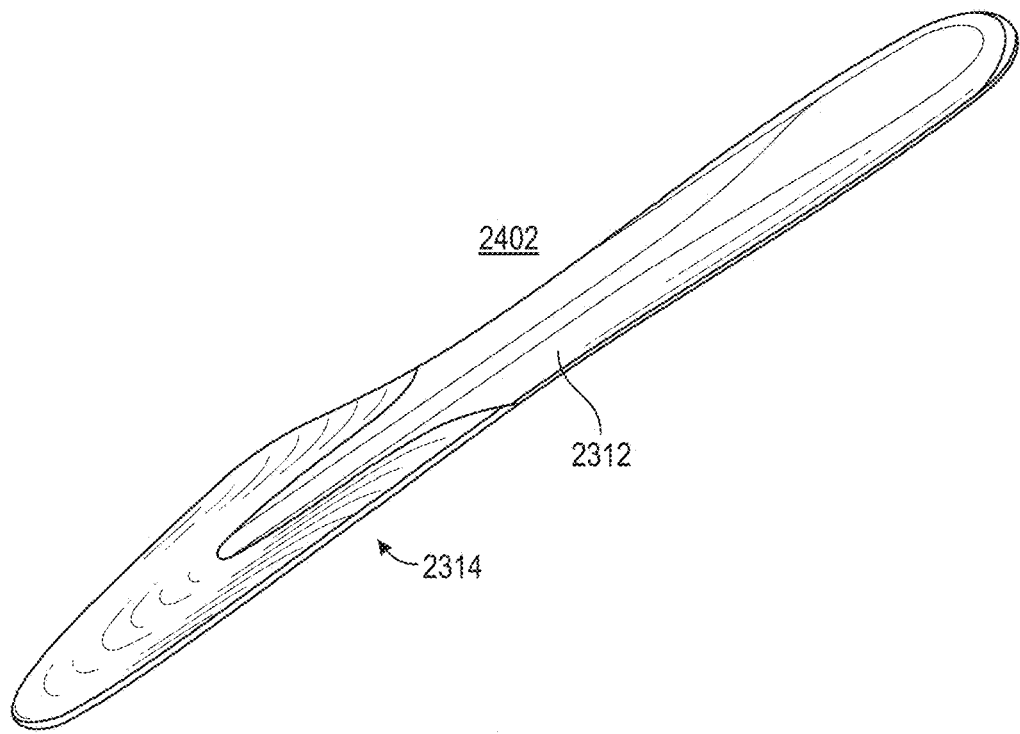

In some embodiments, as shown in FIG. 23B, the gel applicator 2310 has handle 2312 and a gel controlling mechanism 2314 that extends around one end and about equal distances along each of both sides edges of the handle 2312. In some embodiments, as shown in FIG. 23C, the gel applicator 2404 has a gel controlling mechanism that is along one edge of the handle but not along the opposite edge of the handle.

Figure 23C:
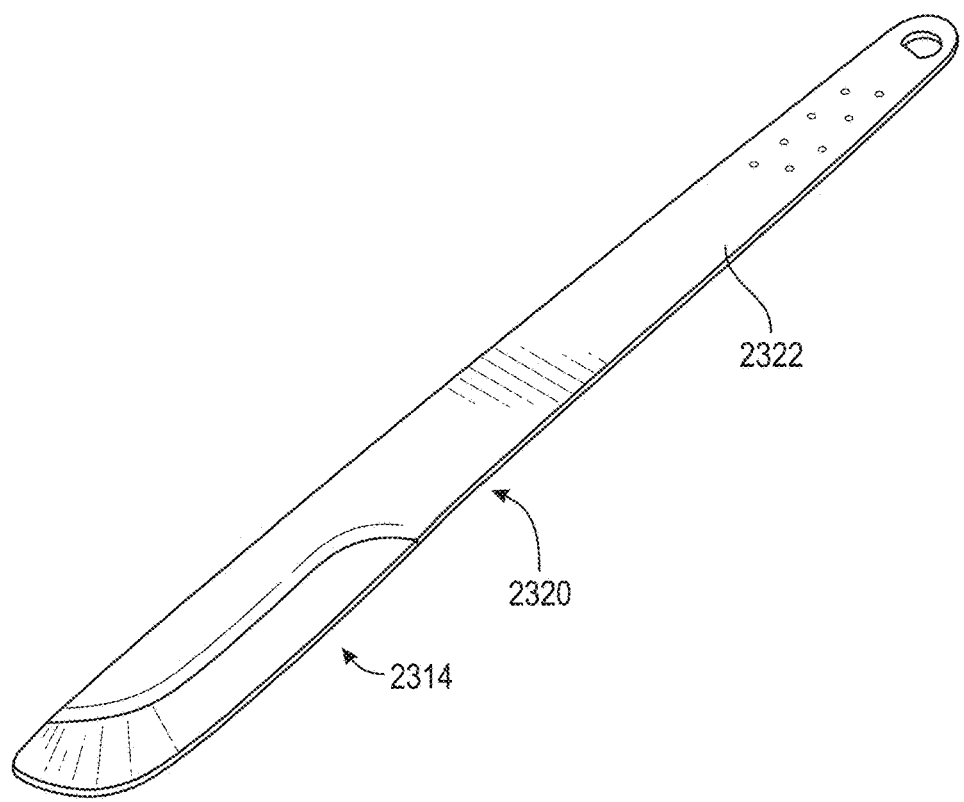
Figure 23D:
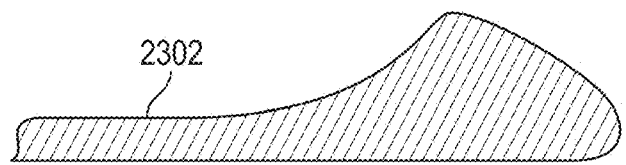
FIG. 23D illustrates a cross-section view of a portion of the gel applicator of FIG. 21A.

In any of the embodiments of FIG. 23A, FIG. 23B, and FIG. 23C, the second end of the handle (the end opposite the end to which the gel controlling mechanism is attached) may include one or more features for enhancing a user's grip including, but not limited to a textured surface (having ribs, grooves, protrusions or the like), a shaped surface. For example, as shown in FIG. 23A and FIG. 23D, the handle 2302 may include a recessed or indented surface 2302a having a shape for receiving a user's thumb at or near the second end of the handle, for enhancing the ability of a user to grip the handle by pinching the handle between a thumb and one or more fingers of one hand. In some embodiments, the handle may include one or more textured features within the recessed or indented surface for further enhancing the user's grip. Alternatively or in addition, the handle may include a raised peripheral lip round its outer edge, as shown in FIG. 23B. Alternatively or in addition, the handle may include one or more protrusions or raised elements forming a textured surface adjacent the second end of the handle, as shown in FIG. 23C.

In any of the embodiments of FIG. 23A, FIG. 23B, and FIG. 23C, a lanyard (such as described above with regard to the lanyard 656 or lanyard 2206) may be attached to the handle in any suitable manner including, but not limited to the manners described above for lanyard 656 and lanyard 2206. For example, the handle in any of the embodiments of FIG. 23A, FIG. 23B, and FIG. 23C may include an hole (such as a hole adjacent the second end of the handle as shown in FIG. 23C) through which a lanyard may be looped as described above with regard to the lanyard 2206.

Figure 24A:
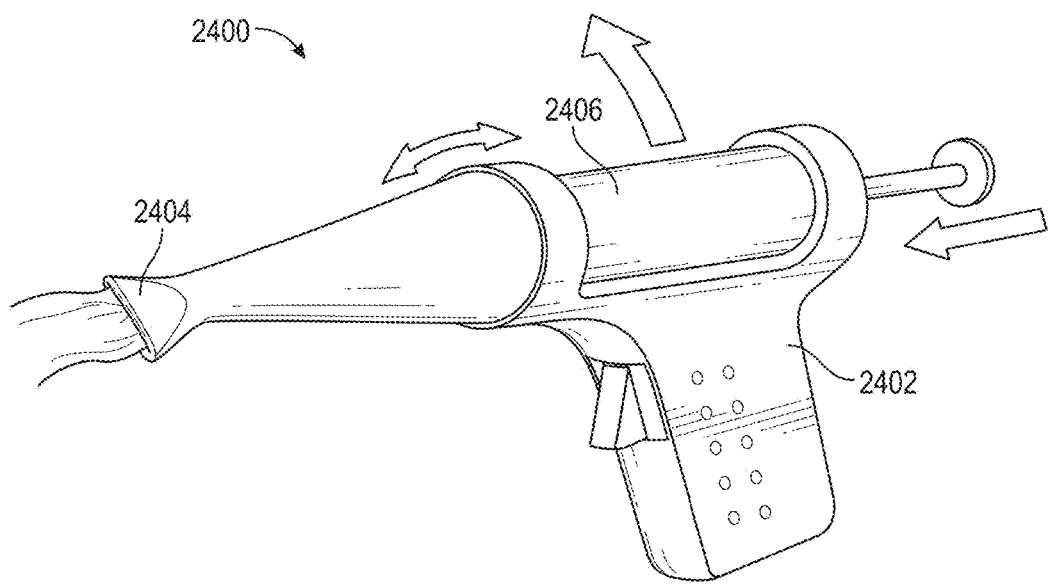
FIG. 24A and FIG. 24B illustrate various views of a gel application system according to various embodiments.
Figure 24B:
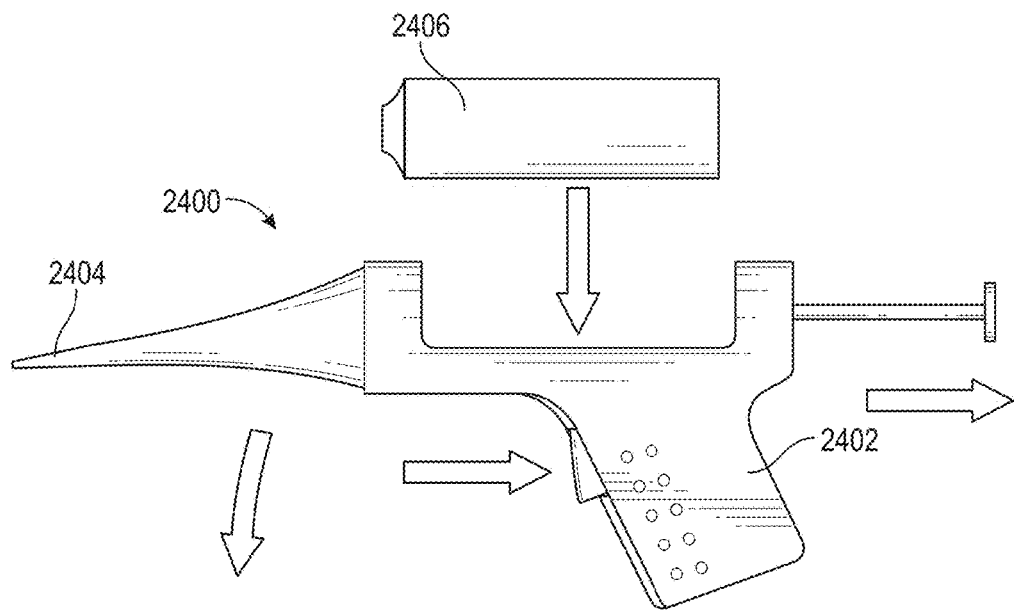

FIG. 24A and FIG. 24B illustrate various views of a gel application system 2400 according to various embodiments.

In some embodiments, the gel application system 2400 includes a dispenser body 2402, a tip 2404, and a gel cartridge 2406. In some embodiments, the dispenser body 2402 includes a slot for receiving the gel cartridge 2406. The dispenser body further includes a handle 2402 for allowing a user to grip the gel application system 2400, a plunger for pushing the gel out of the gel application system 2400, and a trigger for actuating the plunger and controlling discharge of the gel. The plunger may be spring loaded or biased to provide a pushing force on the gel cartridge 2406, after the plunger has been pulled back against the spring or bias force and the trigger is actuated. In some embodiments, the tip 2404 is configured to be attached to the dispenser body 2402 (e.g., by screwing or snapping thereto), and the tip 2404 is tapered to focus the gel out of the narrow opening at the end of the tip 2504. In some embodiments, the tip 2404 and the gel cartridge 2406 are disposable. In some embodiments, the tip 2404 has a configuration and is made of a material the same or similar to the tip 2004 described herein. In some embodiments, a user loads the gel cartridge 2406 into the dispenser body 2402 and pulls back the plunger. The user then pulls the trigger to actuate the plunger and excrete gel from the tip 2404 via the pushing force exerted onto the gel by the plunger.

Although the above description refers to gel, any suitable substance for dispensing out of the gel application systems described herein can be used. For example, any type of gel, liquid, paste, and the like can be housed within the gel application systems described herein, such as, but not limited to, medical-related substances (e.g., ultrasound gel, ointment, cream, and the like), non-medical device substances (e.g., cosmetic products, lotions, and the like), culinary products (e.g., condiments, seasoning, sauces, and the like), and so on. In some embodiments, the substance housed in the gel application systems described herein includes gel used in conjunction with ultrasound medical devices, such as, but not limited to, ultrasound scanners, ultrasound imaging, ultrasound sonography, TCD, and the like.

In some embodiments, the amount or volume of gel housed in the gel packets, packets, or gel application systems described herein is a predetermined amount, and the amount can vary depending on application of the systems described herein. For example, a first amount of gel can be housed within a system described herein when used for a TCD scan, while a second amount different from the first amount of gel can be housed within a system described herein when used for ultrasound sonography. In some embodiments, the gel housed within the systems described herein is color-coded based on particular purposes. For example, gel used for ultrasound sonography can have a particular color (e.g., red), gel used for TCD scanning can have a different color (e.g., purple), gel that is hypoallergenic can have another color (e.g., green), and so on.

The above used terms, including "held fast," "mount," "attached," "coupled," "affixed," "connected," "secured," and the like are used interchangeably. In addition, while certain embodiments have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. In addition, features described and included in any one embodiment may be readily incorporated into any of the other embodiments, including, but not limited to a gel applicator, a gel spreader, a gel scraper, a lanyard, a self-closing nozzle, bristles, tube or straw, tear section or the like. Thus, the previous description is not intended to be limited to the implementations shown herein but is to be accorded the widest scope consistent with the principles and novel features disclosed herein.

What is claimed is:

1. A gel application system comprising:
    an applicator body having a first surface, a second surface and at least one opening extending through the applicator body from the first surface to the second surface;
    a gel scraper located along an outer edge of the applicator body and
    at least one gel packet attached to the first surface of the applicator body and defining an interior volume containing gel, the interior volume of the gel packet being in fluid flow communication with the at least one opening,
    wherein the at least one gel packet is made of a material that has sufficient flexibility to allow a user to squeeze and compress the interior volume and expel gel through the at least one opening, by applying a compression force on the gel packet, and wherein the applicator body is a substantially rigid body having an elongated shape.

2. The gel application system as recited in claim 1, wherein the elongated shape of the applicator body defines a lengthwise dimension with a first end and a second end, and wherein the at least one opening is located closer to the first end than to the second end.

3. The gel application system as recited in claim 2, wherein the at least one opening comprises a slot-shaped opening having an elongated shape with a lengthwise dimension extending along the lengthwise dimension of the applicator body.

4. The gel application system as recited in claim 2, wherein the gel packet includes a large volume end and a small volume end located opposite to the large volume end, wherein the large volume end of the gel packet is configured to retain a larger volume of gel relative to the small volume end of the gel packet.

5. The gel application system as recited in claim 4, wherein the large volume end of the gel packet is located adjacent to the second end of the applicator body, and the small volume end of the gel packet is located adjacent to the first end of the applicator body.

6. The gel application system as recited in claim 5, wherein the first surface of the applicator body includes a passage or groove extending along at least a portion of the length dimension of the applicator body, forming a channel for enhancing a flow of the gel from the large volume end of the gel packet to the at least one opening in the applicator body.

7. The gel application system as recited in claim 1, wherein the gel packet comprises at least one sheet of flexible material sealed around a peripheral edge to the applicator body to form a flexible wall around one or more internal volumes that contain the gel between the sheet of flexible material and the applicator body.

8. The gel application system as recited in claim 7, wherein the at least one sheet of flexible material of the gel packet comprises plastic, rubber or metal foil.

9. The gel application system as recited in claim 1, wherein the at least one opening comprises a plurality of slot-shaped openings, each having an elongated shape.

10. The gel application system as recited in claim 1, wherein the applicator body defines a lengthwise dimension with a first end and a second end, and wherein the at least one opening comprises a plurality of openings located closer to the first end than to the second end.

11. The gel application system as recited in claim 1, further comprising a peel-off cover attached to the applicator body to cover and seal the at least one opening to inhibit expulsion of gel from the at least one opening.

12. The gel application system as recited in claim 1, wherein the applicator body is transparent or partially transparent such that gel is viewable along at least a portion of the applicator body.

13. The gel application system as recited in claim 1, wherein the gel scraper adjusts a placement and thickness of expelled gel or scrapes expelled gel.

14. The gel application system as recited in claim 13, wherein the gel scraper extends along an entire edge curvature of the first end of the applicator body.

15. The gel application system as recited in claim 13, wherein the gel scraper: (a) is affixed to or formed on the first surface of the applicator body, or (b) protrudes outward relative to the first surface of the applicator body.

16. The gel application system as recited in claim 13, wherein the gel scraper: (a) is affixed to or formed on the second surface of the applicator body, or (b) protrudes outward relative to the second surface of the applicator body.

17. The gel application system as recited in claim 13, wherein the gel scraper comprises a soft material including at least one of rubber, closed cell foam, open cell foam, self-skinning open or closed cell foams, cast, aerated, or extruded silicone or urethane, or polyurethane.

18. The gel application system as recited in claim 13, wherein the gel scraper protrudes outward relative to the second surface of the applicator body, or the scraper protrudes outward relative to the first surface of the applicator body.

19. The gel application system as recited in claim 18, wherein the gel scraper comprises a soft material including at least one of rubber, closed cell foam, open cell foam, self-skinning open or closed cell foams, cast, aerated, or extruded silicone or urethane, or polyurethane; or wherein the scraper comprises a rigid material including at least one of plastic, rubber, silicon, metal, ceramic, composite material, wood, cardboard, or cardstock.

20. A method of making a gel application system comprising:
providing an applicator body having a first surface, a second surface and at least one opening extending through the applicator body from the first surface to the second surface; providing a gel scraper along an outer edge of the applicator body
attaching at least one gel packet to the first surface of the applicator and defining an interior volume containing gel, the interior volume of the gel packet being in fluid flow communication with the at least one opening;
wherein the at least one gel packet is made of a material that has sufficient flexibility to allow a user to squeeze and compress the interior volume and expel gel through the at least one opening, by applying a compression force on the gel packet; and
wherein the applicator body is a substantially rigid body having an elongated shape.

21. The method as recited in claim 20, wherein the applicator body defines a lengthwise dimension with a first end and a second end, and wherein the at least one opening is located closer to the first end than to the second end.

22. The method as recited in claim 21, wherein the gel packet includes a large volume end and a small volume end located opposite to the large volume end, wherein the large volume end of the gel packet is configured to retain a larger volume of gel relative to the small volume end of the gel packet.

23. The method as recited in claim 22, wherein the large volume end of the gel packet is located adjacent to the second end of the applicator body, and the small volume end of the gel packet is located adjacent to the first end of the applicator body.

24. The method as recited in claim 23, further comprising providing a passage or groove in the first surface of the applicator body, the passage or groove extending along at least a portion of the length dimension of the applicator body to form a channel for enhancing a flow of the gel from the large volume end of the gel packet to the at least one opening in the applicator body.

25. The method as recited in claim 20, wherein attaching at least one gel packet comprises sealing at least one sheet of flexible material to the applicator body to form a flexible wall around one or more internal volumes that contain the gel between the sheet of flexible material and the applicator body.

26. The method as recited in claim 20, further comprising attaching a peel-off cover to the applicator body to cover and seal the at least one opening to inhibit expulsion of gel from the at least one opening.

27. The method as recited in claim 20, wherein the gel scraper is provided for adjusting a placement and thickness of expelled gel or scraping expelled gel.

28. The method as recited in claim 27, wherein the gel scraper is located along an outer edge of the applicator body.

29. The method as recited in claim 27, wherein the applicator body defines a lengthwise dimension with a first end and a second end, wherein the at least one opening is located closer to the first end than to the second end, and wherein the gel scraper extends along an entire edge curvature of the first end of the applicator body.

* * * * *